US007358055B2

(12) United States Patent
Valkirs et al.

(10) Patent No.: US 7,358,055 B2
(45) Date of Patent: Apr. 15, 2008

(54) DIAGNOSTIC MARKERS OF ACUTE CORONARY SYNDROME AND METHODS OF USE THEREOF

(75) Inventors: Gunars Valkirs, Escondido, CA (US); Jeffrey Dahlen, San Diego, CA (US); Howard Kirchick, San Diego, CA (US); Kenneth F. Buechler, San Diego, CA (US)

(73) Assignee: Biosite, Inc., San Diego, CA (US)

( * ) Notice: Subject to any disclaimer, the term of this patent is extended or adjusted under 35 U.S.C. 154(b) by 0 days.

(21) Appl. No.: 11/205,571

(22) Filed: Aug. 17, 2005

(65) Prior Publication Data

US 2006/0063204 A1 Mar. 23, 2006

Related U.S. Application Data

(62) Division of application No. 10/139,086, filed on May 4, 2002.

(60) Provisional application No. 60/315,642, filed on Aug. 28, 2001, provisional application No. 60/288,871, filed on May 4, 2001.

(51) Int. Cl.
*G01N 33/53* (2006.01)

(52) U.S. Cl. .................................... 435/7.1

(58) Field of Classification Search ................ 435/7.1, 435/4, 7.8, 7.91–7.95, 287.1–289.1, 973; 436/514–548; 422/50–73

See application file for complete search history.

(56) References Cited

U.S. PATENT DOCUMENTS

| | | | |
|---|---|---|---|
| 5,114,923 A | 5/1992 | Seilhamer et al. | |
| 5,206,140 A | 4/1993 | Marder et al. | |
| 5,290,678 A * | 3/1994 | Jackowski | 435/7.4 |
| 5,352,587 A | 10/1994 | Chang et al. | |
| 5,422,393 A | 6/1995 | Bricker et al. | |
| 5,453,359 A | 9/1995 | Gargan et al. | |
| 5,480,792 A | 1/1996 | Buechler et al. | |
| 5,525,524 A | 6/1996 | Buechler et al. | |
| 5,631,171 A | 5/1997 | Sandstrom et al. | |
| 5,679,526 A | 10/1997 | Buechler et al. | |
| 5,786,163 A | 7/1998 | Hall | |
| 5,795,725 A | 8/1998 | Buechler et al. | |
| 5,824,799 A | 10/1998 | Buechler et al. | |
| 5,843,690 A | 12/1998 | Gargan | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,028,055 A | 2/2000 | Lowe et al. | 514/12 |
| 6,057,098 A | 5/2000 | Buechler et al. | |
| 6,113,855 A | 9/2000 | Buechler | |
| 6,117,644 A | 9/2000 | DeBold | 435/7.1 |
| 6,124,430 A | 9/2000 | Mischak et al. | |
| 6,143,576 A | 11/2000 | Buechler | |
| 6,147,688 A | 11/2000 | Clair | |
| 6,156,521 A | 12/2000 | Buechler et al. | |
| 6,171,870 B1 * | 1/2001 | Freitag | 436/518 |
| 6,235,489 B1 | 5/2001 | Jackowski | |
| 6,309,888 B1 | 10/2001 | Holvoet et al. | |
| 6,461,828 B1 | 10/2002 | Stanton et al. | |
| 6,627,457 B2 | 9/2003 | Pandian et al. | |
| 6,670,138 B2 | 12/2003 | Gonzalez-Zulueta et al. | |
| 2003/0022235 A1 * | 1/2003 | Dahlen et al. | 435/7.1 |
| 2004/0167341 A1 | 8/2004 | Haffner et al. | |

FOREIGN PATENT DOCUMENTS

| | | |
|---|---|---|
| EP | 0999447 A1 | 5/2000 |
| WO | WO 00/018801 | 4/2000 |
| WO | WO 00/052476 | 9/2000 |
| WO | WO 01/014885 | 3/2001 |
| WO | WO 02/083913 | 10/2002 |
| WO | WO 02/08967 | 11/2002 |

OTHER PUBLICATIONS

Newby et al., "Bedside Multimarker Testing for Risk Stratification in Chest Pain Units; The Chest Pain Evaluation by Creatine Kinase-MB, Myoglobin, and Troponin I (Checkmate) Study" Circulation, (Apr. 10, 2001); 103: pp. 1832-1837.*

Antman et al., "Cardiac-specific Troponin I Levels to Predict the Risk of Mortality in Patients with Acute Coronary Syndromes", The New England Journal of Medicine, (1996), pp. 1342-1349, vol. 335, No. 18.*

Arakawa et al., "Plasma Brain Natriuretic Peptide Concentrations Predict Survival After Acute Myocardial Infarction", JACC, vol. 27, No. 7, (Jun. 1996), pp. 1656-1661.*

Richards et al., "Neuroendocrine prediction of the left ventricular function and heart failure after acute myocardial infarction", Heart, (1999); 81: 114-120.*

Singh et al., Clinical Profile of Q-Wave and Non-Q Wave Myocardial Infarction, Journal of Indian Academy of Clinical Medicine, vol. 5, No. 1.*

(Continued)

*Primary Examiner*—Ann Y. Lam
(74) *Attorney, Agent, or Firm*—Foley & Lardner, LLP

(57) ABSTRACT

The present invention relates to methods for the diagnosis and evaluation of acute coronary syndromes. In particular, patient test samples are analyzed for the presence and amount of members of a panel of markers comprising one or more specific markers for myocardial injury and one or more non-specific markers for myocardial injury. A variety of markers are disclosed for assembling a panel of markers for such diagnosis and evaluation. In various aspects, the invention provides methods for the early detection and differentiation of stable angina, unstable angina, and myocardial infarction. Invention methods provide rapid, sensitive and specific assays that can greatly increase the number of patients that can receive beneficial treatment and therapy, reduce the costs associated with incorrect diagnosis, and provide important information about the prognosis of the patient.

10 Claims, No Drawings

OTHER PUBLICATIONS

Theroux et al., "Acute Coronary Syndromes", Circulation, 1998; 97; 1195-1206.*

Katus et al., "Diagnostic Efficiency of Troponin T Measurements in Acute Myocardial Infarction", Circulation, vol. 83, No. 3, Mar. 1991, pp. 902-912.*

University of Pennsylvania Health System, Glossary, "Acute myocardial infarction", [online], [retrieved on Jan. 30, 2007], [retrieved from http://pennhealth.com/cardiac/pcc_glossary.html].*

Stedman's Medical Dictionary, 26th Edition, (1995), definition on "infarct".*

Fonarow et al., "Combining Natriuretic Peptides and Necrosis Markers in Determining Prognosis in Heart Failure," Reviews in Cardiovascular Medicine, 2003, Suppl. 4, vol. 4.

Richards et al., "Neuroendocrine prediction of left ventricular function and heart failure after acute myocardial infarction," Heart, 1999, pp. 114-120, vol. 81.

Saady et al., "Left appendage: structure function, and role in thromboembolism," Heart, 1999, pp. 547-555, vol. 82.

Cassin et al., *E realizzablie una strategie operative piu efficace per la gestions in urgenza del paziente con dolore toracico acuto,*? Italian Heart Journal Supplement, Feb. 2000, pp. 186-201, vol. 1, No. 2.

Sonel et al., *Prospective Study Correlating Fibrinopeptide A, Troponin I, Myoglobin, and Myosin Light Chain Levels with Early and Late Ischemic Events in Consecutive Patients Presenting to the Emergency Department With Chest Pain*, Circulation, Sep. 5, 2000, pp. 1107-1113.

Hunt et al., *Immunoreactive amino-terminal pro-brain natriuretic peptide (NT-PROBNP): a new marker of cardiac impairment*, Clinical Endocrinology, 1997, pp. 287-296, vol. 47.

Futterman et al., *Novel Markers in the Acute Coronary Syndrome: BLP, IL-6, PAPP-A*, American Journal of Critical Care, Mar. 2002, pp. 168-172, vol. 11, No. 2.

Harter et al., Caspase-3 activity is present in cerebrospinal fluid from patients with traumatic brain injury. Journal of Neuroimmunology, 121:76-78, 2001.

Huttunen et al., Coregulation of neurite outgrowth and cell survival by amphoterin and S100 protiens through receptor for advanced glycation end products (RAGE) activation. The Journal of Biological Chemistry, 275:40096-40105, 2000.

Mussack et al., Early cellular brain damage and systemic inflammatory response after cardiopulmonary resusicitation or isolated severe head trauma: a comparative pilot study on common pathomechanisma. Resuscitation, 49:193-199, 2001.

Yakoviev et al., Activation of CPP32-Like caspases contributes to neuronal apoptosis and neurological dysfunction after traumatic brain injury. The Journal of Neuroscience, 17(19): 7415-724, 1997.

International Search Report for international application No. PCT/US04/26984.

Notice of References Cited PTO-892, Part of Paper No. 20041202 from U.S. Appl. No. 10/225,082, filed Aug. 20, 2002.

International Search Report and the Written Opinion of the International Searching Authority from PCT Application No. PCT/US04/12024.

Ando et al., "Plasma Concentrations of Atrial, Brain, and C-type Natriuretic Peptides and Endothelin-1 in Patients With Chronic Respiratory Diseases," CHEST, 110:463-68, (1996).

Arakawa et al, Plasma brain natriuretic peptide concentrations predict survival after cute myocardial infarction, JACC, 27:1656-61, (1996).

Belforini et al., "Interest of BNP and troponin in the management of cardiologic emergency." Abstract No. P2829.

Bruccoleri et al., "Brain Natriuretic Peptide in Patients With Acute Myocardian Infarction and Hypertension." Abstract No. H058, Clinical Chemistry and Laboratory Medicine, Poster Abstracts, IFCC WorldLab 1999, Firenze, Jun. 6-11, 1999.

Clerico and Emdin, "Diagnostic accuracy and prognostic relevance of the measurement of cardiac natriuretic peptides: A Review." Clinical Chemistry, 50:33-50, (2004).

Clerico et al., "Pathophysiologic Relevance of Measuring the Plasma Levels of Cardiac Natriuretic Peptide Hormones in Humans." Horm Metab Res, 31:487-498; (1999).

Clerico et al., "Circulating levels of cardiac natriuretic peptides (ANP and BNP) measured by highly sensitive and specific immunoradiometrio assays in normal subjects and in patients with different degrees of heart failure." J. Endocrinol. Invest., 21:170-179 (1998).

Croal et al., Cardiac troponin i and brain natriuretic peptide as markers of doxorubicin cardiotoxicity. Clinical Chemistry, 47 (6) Supp., Abstract No. 490, p. A149, (2001).

Croal et al., Brain natriuretic peptide and caradiac troponin I of markers of doxorubicin cardiotoxicity. Abstract 4769. Blood, Lymphoma: Therapy, Excluding Transplantation, p. 239b.

Darbar et al., Diagnostic value of B-type natriuretic peptide concentrations in patients with acute myocardial infarction. Am. J. Cardiol., 78:284-287, (1998).

Davidson et al., "C-type natriuretic Peptide An Endogenous Inhibitor of Vascular Angiotensin-converting Enzyme Activity." Circulation, 93:1166-1159, (1996).

DeLemos et al., The prognostic value of B-type natriuretic peptide in patients with acute coronary syndromes. N.Eng.Journal of Medicine, 345:1014-1021, (2001).

Fonarow and Horwich, "Combining Natriuretic Peptides and Necrosis Markers in Determining Prognosis in Heart Failure." Rev Cardiovasc Med., 4:(Suppl 4)S20-S28, (2003).

Hammerer-Lercher et al., "Head-to-head comparison of N-terminal pro-brain natriuretic peptide, brain natriuretic peptide and N-terminal pro-atrial natriuretic peptide in diagnosing left ventricular dysfunction," Clinica Chimica Acta, 310:193-197, (2001).

Hammerer-Lercher et al., "Cardiac Natriuretic Peptides: New Laboratory Parameters In Heart Failure Patients." Clin,Lab., 47:265-277, (2001).

Horio et al., "Serial changes in atrial and brain natriuretic peptides in patients with acute myocardial infarction treated with early coronary angioplasty." Am Heart J, 128:293-299, (1993).

Ishii et al., "Risk stratification using serum concentrations of cardiac troponin T in patients with end-stage renal disease on chronic maintenance dialysis." Clinica Chemica Acta, 312:69-79, (2001).

Ishii et al., "Risk Stratification Using a Combination of Cardiac Troponin T and Brain Natriuretic Peptide in Patients Hospitalized for Worsening Chronic Heart Failure." Am.J Cardiol, 89-691-695, (2002).

Ishii et al., "Risk Stratification Using Cardiac Troponin T in Patients with End-Stage Renal Disease." CVR&R, 22: (No. 4)i-177 #923. (2001).

Ishii et al., Early risk stratification . . . , Abstracts from the 72$^{nd}$ Scientific Sessions, Abstract No. 3579, Clinical Chemisrty and Laboratory Medicine.

Kikuta et al., "Increased plasma levels of B-type natriuretic peptide in patients with unstable angina." American Heart Journal, 132:101-107, 1996.

Klinger et al., "C-type natriuretic peptide expression and pulmonary vasodilation in hypoxia-adapted rats." Am. J. Physiol. 275:L645-L652, (1998).

Maeda et al., High levels of Plasma Brain Natriuretic Peptide and Interleukin-6 After Optimized Treatment for Heart Failure Are Independent Risk Factors for Morbidity and Mortality In Patients With Congestive Heart Failure. J Am Coll Cardiol, 36:1587-93 (2000).

Maisel, "Cardiac Biomarkers Aid in Diagnosing Ischemia and Heart Failure." CVR&R, 22:217-222, (2001).

Marumoto et al., "Increased secretion of atrial and brain natriuretic peptides during acute myocardial ischaemia induced by dynamic exercise in patients with angina pectoris." Clinical Science, 88:551-556, 1995.

Nagaya et al., "Plasma Brain Natriuretic Peptide as a Prognostic Indicator in Patients With Primary Pulmonary Hypertension." Circulation, 102:865-870, (2000).

Ornlund et al., N-terminal pro-brain natriuretic peptide is an independent predictor of survival in patients with non-ST-segment elevation acute coronary syndromes: a TIM1 11B substudy. Abstract No. 3324, Biochemical markers in acute coronary syndromes. p. 608 (2001).

Ornlund et al., Plasma brain natriuretic peptide as an indicator of left ventricular systolic function and long-term survival after acute myocardial infarction. Circulation, 93:1969-1969, (1996).

Richards et al., "Plasma N-terminal pro-brain natriuretic peptide and adrenomedullin." Circulation, 97:1921-1929, (1998).

Richards et al., Neoroendocrine prediction of the left ventricular function and heart failure after cute myocardial infarction. Heart, 81:114-120, (1999).

Selvais et al., Direct comparison between Endothelin-1, N-Terminal Proatrial Natriuretic Factor, and Brain Natriuretic Peptide as Prognostic Markers of Survival in Congestive Heart Failure, Journal of Cardiac Failure 5:201-207, (2000).

Selvais et al., "Cardiac natriuretic peptides for diagnosis and risk stratification in heart failure: influences of left ventricular dysfunction and coronary artery disease on cardiac hormonal activation." Eur J Clin Invest 28(8):636-642, (1998).

Takase et al., "Myocardial micro-damage in Acute Heart Failure." XIth International Vascular Biology Meeting, Geneva, Switzerland, Sep. 5-9, A161, (2000).

Talwar et al., "Plasma N terminal pro-brain natriuretic peptide and cardiotrophin 1 are raised in unstable angina." Heart, 84:421-424, (2000).

Talwar et al., Profile of plasma N-terminal proBNP following acute myocardial infarction. European Heart Journal, 21:1514-1521, (2000).

Tsutamoto et al., "Plasma brain natriuretic peptide level as a biochemical marker of morbidity and mortality in patients with asymptomatic or minimally symptomatic left ventricular dysfunction—Comparison with plasma angiotensin II and endothelin-1." Eur Heart J, 20:1799-1807, (1999).

Wu, "Analytical and clinical evaluation of new diagnostic tests for myocardial damage." Clinica Chimica Acta 272:11-21, (1998).

Yoshimura et al., Interaction on metabolic clearance between A-type and B-type natriuretic peptides in patients with heart failure. Metabolism, 49:128-1233, (2000).

Yoshimura et al., "Response of plasma concentrations of A type natriuretic peptide and B type natriuretic peptide to alacepril, an angiotensin-converting enzyme inhibitor, in patients with congestive heart failure." Br Heart J, 72:528-533, (1994).

Yu and Sanderson, "Plasma brain natriuretic peptide—an independent predictor of cardiovascular mortality in acute heart failure." Eur J of Heart Failure, 1:59-65, (1999).

Zoccali et al., "Cardiac Natriuretic Peptides Are Related to Left Ventricular Mass and Function and Predict Mortality in Dialysis Patients." J Am Soc Nephrol, 12:1508-1515, (2001).

Akiama, K. et al., "Changes in serum concentrations of matrix metalloproteinases, tissue inhibitors of metallo-proteinases and type IV collagen in patients with various types of glomerulonephritis." Res. Commun. Mol. Pathol. Pharmacol. 95:115-128, 1997.

Amaro, A. et al., "Plasma leukocyte elastase concentration in augiographically diagnosed coronary artery disease." Eur. Heart J. 16:615-622, 1995.

Antman et al., Enoxaparin prevents death and cardiac ischemic events in unstable angina/non-Q- wave myocardial infarction: Results of the thrombolysis in myocardial infarction (TIMI) IIB trial, Circulation 100:593-601 (1999).

Antman et al., "Cardiac-specific troponin 1 levels to predict the risk of mortality in patients with acute coronary syndromes." N. Eng. J. Med., 335:1342-9, 19996.

Ardissino, D. et al., "Tissue factor antigen and activity in human coronary atherosclerotic plaques." Lancet 349:769-771, 1997.

Austgulen, R. et al., "Increased maternal plasma levels of soluble adhesion molecules (ICAM-1, VCAM-1, E-selectin) in preeclampsia." Eur. J. Obstet. Gynecol. Reprod. Biol. 71:53-58, 1997.

Baker, T. et al., "Serum metalloproteinases and their inhibitors; markers for malignant potential." Br. J. Cancer 70:506-5 12, 1994.

Balagopalakrishna, C. et al., "Modification of low density lipoproteins by erythrocytes and hemoglobin under hypoxic conditions." Adv. Exp. Med. Boil. 411:337-345, 1997.

Banks, R.E. et al., "Circulating intercellular adhesion molecule-1 (ICAM-1), E-selectin and vascular cell adhessioon molecule-1 (VCAM-1) in human malignancies." Br. J. Cancer 68:122-124, 1993.

Bayes-Genis, A. et al., "Elevated levels of plasmin-α2 antiplasmin complexes in unstable angina." Thromb. Haemost. 81:865-868, 1999.

Bazzan, M. et al., "No evidence of plateley activation during atrial pacing in subjects with stable angina." Cardiologia 34:217-220, 1989.

Benamer et al., "Comparison of the prognostic value of c-reactive protein and troponin 1 in patients with unstable angina pectoris." Am. J.Cardiol., 82:845-850, 1998.

Bertinchant, et al., "Release kinetics of serum cardiac troponin 1 in ischemic myocardial injury." Clin. Biochem., 29:587-597, 1996.

Bialik, S. et al., "Myocyte apoptosis during acute myocardial infarction in the mouse localizes to hypoxic regions but occurs independently of p53." J. Clin. Invest. 100:1363-1372, 1997.

Biasucci, L.M. et al, "Elevated levels of interleukin-6 unstable angina." Circulation 94:874-877, 1996.

Biasucci, L.M. et al., "Increasing levels of interleukin (IL)-1Ra and IL-6 during the first 2 days of hospitalization in unstable angina are associated with increased risk of in-hospital coronary events." Circulation 99:2079-2084, 1999.

Bitsch, A. et al., "A longitudinal prospective study of soluble adhesion molecules in acute stroke." Stroke 29:2129-2135, 1998.

Blankaert, D. et al., "Constitutive release of metalloproteinase-9 (92-kd Type IV Collagenase) by Kaposl's sarcoma cells." J. Acquir. Immune Defic. Syndr. Hum. Retrovirol. 18:203-209, 1998.

Blann, A. et al., "Soluble intercellular adhesion molecule-1, E-selectin, vascular cell adhesion molecule-1 and von Willebrand factor in stroke." Blood Coagul. Fibrinolysis 10:277-284, 1999.

Blann, A.D. et al., "Evidence of platelet activation in hypertension." J. Hum. Hypertens. 11:607-609, 1997.

Blann, A.D. et al., "Soluble P-selectin in atherosclerosis: A comparison with endothelial cell and platlet markers." Thromb. Haemost. 77:1077-1080, 1997.

Bonfrer et al., "The luminescence immunoassay S-100: a sensitive test to measure circulating S-100B: its prognostic value in malignant melanoma." Br. J. Cancer, 77:2210-2217, 1998.

Bonomini, M. et al., "Serum levels of soluble adhesion molecules in chronic renal failure and dialysis patients." Nephron 79:399-407, 1998.

Bonow, R.O., "New insights into the cardiac natriuretic peptides." Circulation, 93:1946-1950, 1996.

Bossink. A.W. et al., "Plasma levels of the chemokines monocyte chemotactic proteins-1 and -2 are elevated in human sepsis." Blood 86:3841-3847, 1995.

Bowen-Pope, D.F. et al., "Platelet-derived growth factor in vivo: levels, activity and rate of clearance." Blood 64:45 8-469, 1984.

Brown, D.L. et al., "Identification of 92-kD gelatinase in human coronary atherosclarotic lesions." Circulation 91:2125-2131, 1995.

Caligiuri, G. et al., "Immune system activation follows inflammation in unstable angina: pathogenetic implications." J. Am. Coll. Cardiol. 32:1295-1304, 1998.

Cannon et al., "Oral glycoprotein IIb/IIIa inhibition with orbofiban in patients with unstable coronary syndromes (OPUS-TIMI 16) trial." Circualtion 102:149-56 (2000).

Carlstedt, F. et al, "Proinflammatory cytokines, measured in a mixed population on arrival in the emergency department, are related to mortality and severity of disease." J. Intern. Med. 242:361-365, 1997.

Carraro, U. and Franceschi, C., "Apoptosis of skeletal and cardiac muscles and physical exercise." Aging Clin. Exp. Res. 9:19-34, 1997.

Carter, A.M. et al., "Platelet GP IIIa PIA and GP lb variable number tandem repeat polymorphisms and markers of platelet activation in acute stroke." Arterioscler. Thromb. Vasc. Biol. 18:1124-1131, 1998.

Carter, D.B. et al., "Purification, cloning, expression and biological characterization of an interleukin-1 receptor antagonist protein." Nature 344:633-638, 1990.

Carville, D.G. et al., "Thrombus precursor protein (TpT™): marker of thrombosis early in the pathogenesis of myocardial infarction." Clin. Chem. 42;1537-1541, 1998.

Catto, A.J. et al., "von Willebrand factor and factor VIII: C in acute cerebrovascular disease." Thromb. Hemost. 77:1104-1 108, 1997.

Chong, B.H. et al., "Plasma P-selectin is increased in thrombotic consumptive platelet disorders." Blood 83:1535-1541, 1994.

Cohen, A.M. et al., "Plasma clearance and tissue distribution of recombinant human platelet-derived growth factor (B-chain homodimer) in rats." J. Surg. Res. 49:447-452, 1990.

Curzen, N.P. et al., "Can C reactive protein or troponins T and I predict outcome in patients with intractable unstable angina?" heart 80:23-27, 1998.

Dangas, G. et al., "Correlation of serum lipoprotein(a) with the angiographic and clinical presentation of coronary artery disease." Am. J. Cardiol. 83:583-5, A7, 1999.

Davi, G. et al., "Increased levels of soluble P-selectin in hypercholesterolemic patients." Circulation 97:953-957, 1998.

De Caterina, R. et al., "Platelet activation in angina at reat. Evidence by paired measurement of plasma beta-thromboglobulin and platelet factor 4." Eur. Heart J. 9:913-922, 1988.

de Lemos et al., "The prognostic value of B-type natriuretic peptide in patients with acute coronary syndromes." N Engl J Med 345:1014-2 1 (2001).

Depre, C. et al., "Expression of inducible nitric oxide synthase in human coronary atherosclerotic plaque." Cardiovasc. Res. 41:465-472, 1999.

Dinerman, J.L. et al., "Increased neutrophii elastase release in unstable angina pectoris and acute myocardial infarction." J. Am. Coll. Cardiol. 15:1559-1563, 1990.

Doubell, et al., "Identification and immunolocalisation of annexins V and VI, the major cardiac annexins, in rat heart." Cardiovasc. Res., 27:1359-1367, 1993.

Dunlop, L.C. et al., "Characterization of GMP-140 (P-selectin) as a circulating plasma protein." J. Exp. Med. 175:1147-1150, 1992.

Durany and Carreras, "Distribution of phosphoglycerate mutase isozymes in rat, rabbit and human tissues." Comp. Biochem. Physiol. B. Biochem. Mol. Biol., 114:217-233, 1996.

Eisenberg, S.P. et al., "Interleukin 1 receptor antagonist is a member of the interleukin 1 gene family: evolution of a cytokine control mechanism."Proc. Natl. Acad. Sci. U S A. 88:5232-5236, 1991.

Emsley, J. et al., "Crystal structure of the von Willebrand factor A1 domain and implications for the binding of platelet glycoprotein lb." J. Biol. Chem. 273:10396-10401, 1998.

Endo, K. et al., "Elevated levels of serum and plasma metalloproteinases in patients with gastric cancer." Anticancer Res. 17:2253-2258, 1997.

Endo, S. et al., "Plasma interleukin 8 and polymorphonuclear leukocyte elastase concentrations in patients with septic shock."J. Inflamm. 45:136-142, 1995.

Eriksson, S. et al., "Leucocyte elastase as a marker in the diagnosis of acute appendicitis." Eur. J. Surg. 161:901-905, 1995.

Ertenli, I. et al., "P-Selectin as a circulating molecule marker in rheumatoid arthritis with thrombocytosis." J. Rheumatol. 25:1054-1058, 1998.

Etoch et al., "Differential hormonal profiles of adrenomedulin and proadrenomedulin N-terminal 20 peptide in patients with heart failure and effect of treatment on their plasma levels." Clin. Cardiol., 22:113-17, 1999.

Falciani, M. et al., "Elevated tissue factor and tissue factor pathway inhibitor circulating levels in ischaemic heart disease patients." Thromb. Haemost. 79:495-499, 1998.

Fernandes-Alnemri, T. et al., "CPP32, a novel human apoptotic protein with homology to caenorhabditis elegans cell death protein Ced-3 and mammalian interleukin-1β-converting enzyme." J. Biol. Chem. 369:30761-30764, 1994.

Fisher, N.C. et al., "Serum concentrations and peripheral secretion of the beta chemokines monocyte chemoattractant protein 1 and macrophage inflammatory protein 1α in alcoholic liver disease." Gut 45:416-420, 1999.

Fox, J.E. "Shedding of adhesion receptors from the surface of activated platelets." Blood Coagul. Fibrinolysis 5:291-304, 1994.

Frijns C.J. et al., "Soluble adhesion molecules reflect endothelial cell activation in ischemic stroke and in carotid atherosclerosis." Stroke 28:2214-2218, 1997.

Gabay, C. et al., "Interleukin 1 receptor antagonist (IL-1Ra) is an acute-phase protein." J. Clin. Invest 99:2930-2940, 1997.

Gallino, A. et al., "Fibrin formation and platelet aggregation in patients with acute myocardial Infarction: effects of intravenous and subcutaneous low-dose heparin." Am. Heart J. 112:285-290, 1986.

Gamble, J.R. et al., "Prevention of activated neutrophil adhesion to endothelium bu soluble adhesion protein GMP140." Science 249:414-417, 1990.

Gando, S. et al., "Increased neutrophil elastase, persistent intravascular coagulation, and decreased fibrinolytic activity in patients with posttraumatic acute respiratory distress syndrome." J. Trauma 42:1068-1072, 1997.

Garbisa, S. et al., "Correlation of serum metalloproteinase levels with lung cancer metastasis and response to therapy." Cancer Res. 52:4548-4549, 1992.

Genereau, T. et al., "Human neutrophil elastase in temporal (Giant Cell) arteritis: plasma and immunohistochemical studies." J. Rheumatol. 25:710-713, 1998.

Gensini, G.F. et al., "Increased protein C and fibrinopeptide A concentration in patients with angina." Thromb. Res. 50:517-525, 1988.

George, D.K. et al., "Evidence for altered hepatic matrix degradation in genetic haemochromatosis." Gut. 42:715-720, 1998.

Ghaisas, N.K. et al., "Elevated levels of circulating soluble adhesion molecules in peripheral blood of patients with unstable angina." Am. J. Cardiol. 80:617-619, 1997.

Ghanem, H. et al., "Increased low density lipoprotein oxidation in stable kidney transplant recipients." Kidney Int. 49:488-493, 1996.

Giambanco, I. et al., "Immunohistochemical localization of Annexin V (CaBP33) in rat organs." J.Histochem. Cytochem., 39:1189-1198, 1991.

Glatz et al., "Fatty-acid-binding protein as a plasma marker for the estimation of myocardial infant size in humans." Br. Heart J., 71:135-140, 1994.

Gleeson, M. et al., "The effect of severe eccentric exercise-induced muscle damage of plasma elastase, glutamine and zinc concentrations." Eur. J. Appl.Physiol. 77:543-546, 1998.

Gohji, K. et al., "Elevation of serum levels of matrix metalloproteinase-2 and -3 as new predictors of recurrence in patients with urothelial carcinoma." Cancer 78:2379-2387, 1996.

Goto, S. et al., "Enhanced shear-induced platelet aggregation in acute myocardial infarction." Circulation 99:608-613, 1999.

Grisolia et al., "Influence of size, protein concentration, protein synthesis inhibitors, and carbon on clearance of enzymes and proteins from blood." Physiol. Chem. Phys., 8:37-52, 1976.

Gruber, B.L. et al., "Markedly elevated serum MMP-9 (gelatinase B) levels in rheumatoid arthritis: A potentially useful laboratory marker." Clin. Immonol. Immunopathol. 78:161-171, 1996.

Gurfinkel, F. et al., "Importnace of thrombosis and thrombolysis in silent ischaemia: comparison of patients with acute myocardial infarction and unstable angina." Br. Heart J. 71:151-155, 1994.

Hammerman, S.I. et al., "Endothelial cell nitrate oxide production in acute chest syndrome." Am. J. Physiol. 277:H1579-H1592, 1999.

Hasegawa et al., "S100a0 protein as a marker for tissue damage related to extracorporeal shock wave lithotripsy." Eur, Urol., 24:393-396, 1993.

Hayasaka, A. et al., "Elevated plasma levels of matrix metalloproteinase-9 (92-kd type IV collagenase/gelatinase B) in hepatocellular carcinoma." Hepatology 24:1058-1062, 1996.

Haznedaroglu, I.C. et al., "Selectins and IL-6 during the clinical course of idiopathic thrombocytopenic purpura." Acta Haematol. 101:16-20, 1999.

Herraez-Dominguez, et al., "Immunological determination of muscle-type enolase in the serum as a diagnostic test for myocardial infarction." Clin. Chim. Acta, 64:307-315, 1975.

Hirashima; Y. et al., "Cerebrospinal fluid tissue factor and thrombin-Antithrombin III complex as indicators of tissue injury after subarachniod hemmorage," Stroke 28:166-1670, 1997.

Hirashima, Y. et al., "Elevation of platelet activating factor, inflammatory cytokines, and coagulation factors in the internal jugular vein of patients with subarachnoid hemorrhage." Neurochem Res. 22:1249-1255, 1997.

Hoffmeister, H.M. et al., "Correlation between coronary morphology and molecular markers of fibrinolysis in unstable angina pertoris." Atherosclerosis 144:151-157, 1999.

Hoffmeister, H.M. et al., "Alterations of coagulation and fibrinolytic and kallikrein-kinin systems in the acute and postacute phases in patients with unstable angina pectoris." Circulation 91:2520-2527, 1995.

Hollander, J.E. et al., "Risk stratification of emergency department patients with acute corooonary syndromes using P-selectin." J. Am. Coll. Cardiol. 34:95-105, 1999.

Holvost, P. et al., "Oxidized LDL and malondialdehyde-modified LDL in patients with acute coronary syndromes and stable coronary artery disease." Circulation 98:1487-1494, 1998.

Holvoet, P. et al., "Malondialdehyde-modified LDL as a marker of acute coronary syndromes." JAMA, 281:1718-1721, 1999.

Holvoet, P., "Oxidative modification of low-density lipoproteins in atherothrombosis." Acta Cardiol 53:253-260, 1998.

Hunt et al., "The amino-terminal portion of pro-brain natriuretic peptide (Pro-BNP) circulates in human plasma." Biochem. Biophys. Res. Commun., 214:1175-83, 1995.

Iiyama, K. et al., "Patterns of vascular cell adhesion molecule-1 and intercellular adhesion molecule-1 expression in rabbit and mouse atherosclerotic lesions and at sites predisposed to lesion formation." Circ. Res. 85:199-207, 1999.

Iizasa, T. et al., "Elevated levels of circulating plasma matrix metalloproteinase 9 in non-small cell lung cancer patients." Clin., Cancer Res. 5:149-153, 1999.

Ikeda, H. et al., "Increased soluble form of P-selectin in patients with unstable angina." Circulation 92:1693-1696, 1995.

Ikeda, H. et al., "Soluble form of P-selectin in patients with acute myocardial infarction." Coron. Artery Dis. 5:515-518, 1994.

Ishii et al., "Serum concentrations of myoglobin vs human heart-type cytoplasmic fatty acid-burning protein in early detection of acute myocardial infarction." Clin. Chem., 43:1372-1378, 1997.

James, T.N., "The variable morphological coexistence of apoptosis and necrosis in human myocardial infarction: significance for understanding its pathogenesis, clinical course, diagnosis and prognosis." Coron. Artery Dis. 9:291-307, 1998.

Janoff, A., "Elastase in tissue injury." Annu Rev Med 36:207-216, 1985.

Jimenez, W. et al., "Nitric oxide production and inducible nitric oxide synthase expression in peritoneal macrophages of cirrhotic patients." Hepatology 30:670-676, 1999.

Johnson, J.L. et al., "Activation of matrix-degrading metalloproteinases by mast cell proteases in atherosclerotic plaques." Arterioscler. Thromb. Vasc. Boil. 18:1707-17 15, 1998.

Johnston, G.I. et al., "Structure of the human gene encoding granule membrane protein-140, a member of the selectin family of adhesion receptors for leukocytes." J. Biol. Chem. 265:21381-21385, 1990.

Journal of the American College of Cardiology, "Myocardial Infarction redefined—A consensus document of the Joint European Society of Cardiology/American College of Cardiology Committee for the redefinition of myocardial infarction." 36:959-969, 2000.

Kai, H. et al., "Peripheral blood levels of matrix metalloproteases-2 and -9 are elevated in patients with acute coronary syndromes." J. Am. Coll. Cardiol. 32:368-372, 1998.

Kaikita, K. et al., "Tissue factor expression on macrophages in coronary plaques in patients with unstable angina." Arterioscler. Thromb. Vasc. Biol. 17:2232-2237, 1997.

Kaikita, K. et al., "Soluble P-selectin is released into the coronary circulation after coronary spasm." Circulation 92:1726-1730, 1995.

Kaneko et al., "Measurement of plasma annexin V by ELISA in the early detection of acute myocardial infarction." Clin. Chim. Acta, 251:65-80, 1996.

Kaneko, H. et al., "Circulating levels of β-chemokines in systemic lupus erythematosus." J. Rheumatol. 26:568-573, 1999.

Katayama, M. et al., "Soluble P-selectin is present in normal circulation and its plasma level is elevated in patients with thrombotic thrombocytopenic purpura and haemolytic uraemic syndrome." Br. J. Haematol. 84:702-710, 1993.

Kato and Kimura, "S100a0 (αα) protein is mainly located in the heart and striated muscles." Biochim. Biophys. Acta, 842:146-150, 1985.

Kato et al., "Immunoassay of human muscle enolase subunit in serum: a novel marker antigen for muscle diseases." Clin. Chim. Acta, 131:75-85, 1983.

Kaye, D.M. et al., "The failing human heart does not release nitrogen oxides," Life Sci 62:883-887, 1998.

Keyszer, G. et al., "Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers." J. Rheumatol. 36:25 1-258, 1999.

Keyszer, G. et al., "Matrix metalloproteinases, but not cathepsins B, H, and L or their inhibitors in peripheral blood of patients with rheumatoid arthritis are potentially useful markers of disease activity." Z Rheumatol 57:392-398, 1998.

Khan, et al., "Elevation of serum cardiac troponin in noncardiac and cardiac diseases other than acute coronary syndromes." Am. J. Emerg. Med., 17:225-229, 1999.

Kienast, J. et al., "Prothrombin activation fragment 1+2 and thrombin antithrombin III complexes in patients with angina pectoris: relation to the presence and severity of coronary atherosclerosis." Thromb. Haemost, 70:550-553, 1993.

Kikuchi et al., "Clinical evaluation of serum S100ao protein in patients with urogenital diseases and healthy volunteers." Acta Urologica Japonica, 36:1117-1123, 1990.

Kim, D.C. et al, "Kidney as a major clearance organ for recombinant human interleukin-1 receptor antagonist." J. Pharm. Sci. 84:575-580, 1995.

Kim, J.S., "Cytokines and adhesion molecules in stroke and related diseases." J. Neurol. Sci. 137:69-78, 1996.

Kosar, F. et al.; "Plasma leukocyte elastase concentration and coronary artery disease." Angiology 49:193-201, 1998.

Koukkunen, et al., "Troponin T and creatinine kinase isoenzyme MB mass in the diagnosis of myocardial infarction." Ann. Med., 30:488-496, 1998.

Koyama, T. et al., "Determination of plasma tissue factor antigen and its clinical significance." Br. J. Haematol. 87:343-347, 1994.

Krause, et al., "Glycogen phosphorylase isoenzyme BB in diagnosis of myocardial ischaemic injury and infarction." Mol. Cell. Biochem., 160-161:289-295, 1996.

Kruskal, J.B. et al., "Fibrin and fibrinogen-related antigens in patients with stable and unstable coronary artery disease." N. Engl. J. Med. 317:1361-1365, 1987.

Kudo, S. et al., "Clearance and tissue distribution of recombinant human interleukin 1β in rats." Cancer Res. 50:5751-5755, 1990.

Kurimoto, M. et al., "Plasma platelet-derived growth factor-B chain is elevated in patients with extensively large brain tumors." Acta Neorochir. (Wlen) 137:182-187, 1995.

Landi, G. et al., "Hypercoagulability in acute stroke: prognostic significance." Neurology 37:1667-1671, 1987.

Laskowitz, D.T. et al., "Serum markers of cerebral ischemia." Stroke Cerebrovasc. Dis. 7:234-24 1, 1998.

Latini, R. et al., "Cytokines in acute myocardial infarction: Selective increase in circulating tumor necrosis factor, its soluble receptor, and interleukin-1 receptor antagonist." J. Cardiovasc. Pharmacol. 23:1-6, 1994.

Laurino, J.P. et al., "Thrombus precursor protein™ and the measurement of thrombosis in patients with acute chest pain syndrome." Ann. Clin. Lab. Sd. 27:338-345, 1997.

Lein, M. et al, "Analytical aspects regarding the measurement of metalloproteinases and their inhibitors in blood." Clin. Biochem. 30:491-496, 1997.

Lein, M. et al., "Metalloproteinasen (MMP-1, MMP-3) und ihre inhibitoren (TIMP) im Blutplasma bei patienten mit prostatakarzinom." Urologe A 37:377-381, 1998.

Li, D. et al., "Acute Ischemic heart disease." Am. Heart J. 137:1145-1152, 1999.

Li. Y.S. et al., "The expression of monocyte chemotactic protein (MCP-1) in human vascular endothelium in vitro and in vivo." Mol. Cell. Biochem. 126:61-68, 1993.

Ling, W. et al., "Oxidized or acetylated low density lipoproteins are rapidly cleared by the liver in mice with disruption of the scavenger receptor class A type I/II gene." J. Clin. Invest. 100:244-252, 1997.

Liras, G. et al., "Utilidad pronostica de un ensayo automatizado de elastasa granulocitica en pancreatitis aguda." Rev. Esp. Enfem. Dig. 87:641-652, 1995.

Liu, X. et al., "Purification and characterization of an interleukin-1β-converting enzyme family protease that activates cysteine protease P32 (CPP32)." J. Biol. Chem. 271:13371-13376, 1996.

Liuzzo, G. et al., "Plasma protein acute-phase response in unstable angina is not induced by ischemic injury." Circulation 94:2373-23 80, 1998.

Livrea, M.A. et al., "Oxidative modification of low-density lipoprotein and atherogenetic risk in β-thalassemia." Blood 92:3936-3942, 1998.

Long, X. et al., "p53 and the hypoxia-induced apoptosis of cultured neonatal rat cardiac myocytes." J. Clin. Invest. 99:2635-2643, 1997.

MacManus, J.P. et al., "Cerebral ischemia produces laddered DNA fragments distinct from cardiac ischemia and archetypal apoptosis." J. Cereb. Blood Flow Metab. 19:502-5 10, 1999.

Mahadevan, D. et al., "Structural role of extracellular domain 1 of a α-platelet-derived growth factor (PDGF) receptor for PDGF-AA and PDGF-BB binding." J. Biol. Chem. 270:27595-27600, 1995.

Mair et al., "Early release of glycogen phosphorylase in patients with unstable angina and translent ST-T alterations." Br. Heart J., 72:125-127, 1994.

Mair et al., "Glycogen phosphorylase isoenzyme BB diagnose ischhaemic myocardial damage." Clin. Chim. Acta, 272:79-86, 1998.

Mair et al., "Glycogen phosphorylase isoenzyme BB mass release after coronary artery bypass grafting." Eur. J. Clin. Chem. Clin. Biochem., 32:543-547, 1994.

Mair, "Progress in myocardial damage detection: new biochemical markers for clinicians." Crit. Rev. Clin. Lab. Sci., 34:1-66, 1997.

Manicourt, D.H. et al., "Serum levels of collagenase, stromelysin-1, and TIMP-1." Arthritis Rheum. 37:1774-1783, 1994.

Manten, A. et al., "Procoaguland and proinflammatory activity in acute coronary syndromes." Cardiovasc. Res, 40:389-395, 1998.

Matsuda et al., "A sandwich enzyme immunoassay for human muscle-specific β-enolase and its application for the determination of skeletal muscle injury." Forensic Sci. Int., 99:197-208, 1999.

Matsumori, A. et al., "Plasma levels of the monocyte chemotactic and activating factor/monocyte chemoattractant protein-1 are elevated in patients with acute myocardial infarction." J. Mot Cell. Cardiol. 29:419-423, 1997.

Mehta, J. et al., "Neutrophil function in ischemic heart disease." Circulation 79:549-556, 1989.

Merek Manual of Diagnosis and Therapy, 17th edition, 1999, Ed. Keryn A.G. Lane, p. 1662-1668.

Merek Manual of Diagnosis and Therapy, 17th edition, 1999, Ed. Keryn A.G. Lane, p. 1668-1677.

Mertini, P.A. et al., "Persistent activation of coagulation mechanism in instable angina and myocardial infarction." Circulation 90:61-68, 1994.

Michelson, A.D. et al., "In vivo tracking of platelets: Circulating degranulated platelets rapidly lose surface P-selectin but continue to circulate and function." Proc. Natl. Acad. Sci. U S.A. 93:11877-11882, 1996.

Misumi, K. et al., "Comparison of plasma tissue factor levels in unstable and stable angina pectoris." Am. J. Cardiol. 81:22-26, 1998.

Miwa, K. et al, "Soluble E-selectin, ICAM-1 and VCAM-1 levels in systemis and coronary circulation in patients with variant angina." Cardiovasc. Res. 36:37-44, 1997.

Miyata, S. et al., "Conformational changes in the A1 domain of von Willebrand factor modulating the interaction with platelet glycoprotein Ibα" J. Biol. Chem. 271:9046-9053, 1996.

Montalescot, G. et al., "Early increase of von Willebrand factor predicts adverse outcome in unstable coronary artery disease: Beneficial effects of Enoxaparin." Circulation 98:294-299.

Moore, D.H. et al., "Collagenase expression in ovarian cancer cell lines." Gynecol. Oncol. 65:78-82, 1997.

Mooser, V. et al., "Effect of cardiopulmonary bypass and heparin on plasma levels of Lp(a) and Apo(a) fragments." Arterioscler. Thromb. Vasc. Biol. 19:1060-1065, 1999.

Morita et al., "Evaluation of serum S100ao protein in patients with renal cell carcinoma." Nippon Hinyokika Gakkal Zasshi, 81:1162-1167, 1990.

Morrow et al., "C-reactive protein is a potent predictor of mortality independently of and in combination with Troponin T in acute coronary syndromes: A TIMI 11A substudy." J.Am. Coll. Cardiol., 31:1460-5, 1998.

Mulvihill, N. et al., "Early temporal expression of soluble cellular adhesion molecules in patients with unstable angina and subendocardial myocardial infarction." Am. J. Cardiol. 83:1265-7, A9, 1999.

Mun-Bryce, S. and Rosenberg, G.A., J. "Matrix metalloproteinases in cerebrovascular disease." Cereb. Blood Flow Metab. 18:1163-1172, 1998.

Murawaki, Y. et al., "Clinical usefulness of serum matrix metalloproteinase-2 concentration in patients with chronic viral liver disease." J. Hepatol. 30:1090-1098, 1999.

Murawaki, Y. et al., "Serum matrix metalloproteinase-1 in patients with chronic viral hepatitis." J Gastroenterol. Hepatol. 14:138-145, 1999.

Musso et al., "Troponina 1 cardiaca e troponina t cardiaca nell'angina instabile: incidenza, correlazione, cinetica di rilasciamento e valore prognostico." J.Ital. Cardiol., 26:1013-1023, 1996.

Nakamura, T. et al., "Modulation of plasma metalloproteinase-9 concentrations and peripheral blood monocyte mRNA levels in patients with septic shock: effect of fiber-immobilized polymyxin B treatment." Am. J. Med. Sci. 316:355-360, 1998.

Ni, Z. et al., "Up-regulation of renal and vascular nitric oxide synthase in iron-deficiency anemia." Kidney Int. 52:195-201, 1997.

Nishizama, K. et al., "Protein kinase Cδand αare involved in the development of vasospasm after subarachnoid hemorrhage." Jpn. Circ. J. 62:710-712, 1998.

Nomura et al., "Serum β-enolase in acute myocardial infarction." Br. Heart J., 58:29-33, 1987.

Nomura, S. et al., "Effect of cilostazol on soluble adhesion molecules and platelet-derived micropaarticles in patients with diabetes." Thromb. Haemost. 80:388-392, 1998.

Norregaard-Hansen, et al., "Lack of indication of myocardial cell damage after myocardial ischaemia in patients with severe stable angina." Eur. Heart J., 13:188-193, 1992.

O'Connor, C.M. et al., "Usefulness of soluble and surface-bound P-selectin in detecting heightened platelet activity in patients with congestive heart failure." Am. J. Cardiol. 83:1345-1349, 1999.

Ogawa, H, et al., "Plasma platelet-derived growth factor levels in coronary circulation in unstable angina pectoris." Am. J Cardiol. 69:453-455, 1992.

Ogawa, H. et al, "Plasma soluble intercellular adhesion molecule-1 levels in coronary circulation in patients with unstable angina." Am. J. Cardiol. 83:38-42, 1999.

Ogawa, H. et al., "Platelet-derived growth factor is released into the coronary circulation after coronary spasm." Coron. Artery Dis. 4:437-442, 1993.

Ohtsuka, T. et al., "Clinical implications of circulating soluble Fas and Fas ligand in patients with acute myocardial infarction." Coron. Artery Dis. 10:221-225, 1999.

Oltrona, L. et al., "C-reactive protein elevation and early outcome in patients with unstable angina pectoris," Am. J. Cardiol. 80:1002-1006, 1997.

Otsuki, M. et al., "Circulating vascular cell adhesion molecule-1 (VCAM-1) in atherosclerotic NIDDM patients." Diabetes 46:2096-2101, 1997.

Pellegatta, F. et al., "Soluble E-selectin and intercellular adhesion molecule-1 plasma levels increase during acute myocardial infarction." J. Cardiovasc. Pharmacol. 30:45 5-460, 1997.

Peter, K. et al., "Circulating vascular celladhesion molecule-1 correlates with the extent of human atherosclerosis in contrast to circulating intercellular molecule-1, E-selectin, P-selectin, and thrombomodulin." Arterioscler. Thromb. Vasc. Biol. 17:505-5 12, 1997.

Plow, E.F. and Plescia, J., "Neutrophil secretion during blood coagulation: evidence for a preallikrien independent pathway." Thromb. Haemost. 59:360-363, 1988.

Plow, E.F., "Leukocyte elastase release during blood coagulation." J. Clin. invest. 69:564-572, 1982.

Rabitzsch et al., "Immunoinhibition assay of the serum activity of human glycogen isophosphorylese BB in the diagnosis of the acute myocardial ischaemia." Biomed. Biochim. Acta, 46:S584-S588, 1987.

Rabitzsch et al., "Immunoenzymometric assay of human glycogen phosphorylase isoenzyme BB In diagnosi of ischemic myocardial injury." Clin. Chem., 41:966-978, 1995.

Rabitzsch et al., "Isoenzyme BB of glycogen phosphorylase b and myocardial infarction." Lancet, 341:1032-1033, 1993.

Rebuzzi, A.G. et al., "Incremental prognostic value of serum levels of troponin T and C-reactive protein on admission in patients with unstable angina pectoris," Am. J. Cardiol. 82:715-719, 1998.

Robey, F.A. et al., "Binding of C-reactive protein to chromatin and nucleosome core particles." J. Biol. Chem. 259:7311-7316, 1974.

Romanic, A.M. et al., "Matrix metalloproteinase expression increases after cerebral local ischemia in rats." Stroke 29:1020-1030, 1998.

Rosenberg, G.A., "Matrix metalloproteinases in brain injury." J. Neurotrauma 12:833-842, 1995.

Rossi, E. et al., "Increased plasma levels of platelet-derived growth factor (PDGF-BB + PDGF-AB) in patients with never-treated mild essential hypertension." Am. J. Hypertens. 11:1239-1243, 1998.

Rucinski, B. et al., "Clearance of human platelet factor 4 by liver and kidney: Its alteration by heparin." Am. J. Physiol. 251:H800-H807, 1986.

Sagnella, G.A., "Measurement and significance of circulating natriuretic peptides in cardiovascular disease." Clinical Science, 95:519-529, 1998.

Sakamaki, F. et al., "Soluble form of P-selectin in plasma is elevated in acute lung injury." Am. J. Respir. Crit. Case Med. 151:1821-1826, 1995.

Sakata, K. et al., "Characteristics of vasospastic angina with exercised-induced ischemia analysis of parameters of hemostasis and fibrinolysis." Jpn. Circ. J. 60:277-284, 1994.

Saraste, A., "Morphologic criteria and detection of apoptosis." Herz 24:189-195, 1999.

Sasagawa, T. et al., "The significance of plasma lysophospholipids in patients with renal failure on hemodialysis." J. Nutr. Sci. Vitaminol. (Tokyo) 44:809-818, 1998.

Savonitto et al., "Prognostic value of the admission electrocardiogram in acute coronary syndromes." JAMA, 281:707-13,1999.

Sawicki, G. et al., "Localization and translocation of MMP-2 during aggregation of human platelets." Thromb. Haemost. 80:836-839, 1998.

Seymour, L. et al., "Tissue platelet derived-growth factor (PDGF) predicts for shortened survival and treatment failure in advanced breast cancer." Breast Cancer Res. Treat. 28:247-252, 1993.

Shah, P.K. et al., "Human monocyte-derived macrophages induce collagen breakdown in fibrous caps of atherosclerotic plaques," Circulation 92:1565-1569, 1995.

Shibata, M. et al., "Effect of magnesium sulfate pretreatment and significance of matrix metalloproteinase-1 and interleukin-6 levels of coronary reperfusion therapy for patients with acute myocardial infarction." Angiology 50:573-582, 1999.

Shimomura et al., "Serial changes in plasma levels of soluble P-selectin in patients with acute myocardial infarction." Am.J. Cardial. 81:397-400, 1998.

Siess, W., "Lysophosphatidic acid medicates the rapid activation of platelets and endothelial cells by mildly oxidized low density lipoprotein and accumulates in human atherosclerotic lesions." Proc. Natl Acad. Sci. U. S. A. 96, 693 1-6936, 1999.

Sixma, J.J. and de Groot, P.G., "Von Willebrand factor and the blood vessel wall." Mayo Clin. Proc. 66:628-633, 1991.

Sobel, M. et al., "Circulating platelet products in unstable angina pectoris." Circulation 63:300-306, 1981.

Soejima, H. et al., "Heightened tissue factor associated with tissue factor pathway inhibitor and prognosis in patients with unstable angina." Circulation 99:2908-29 13, 1999.

Soejima, H. et al., "Angiotensin-converting enzyme inhibition reduces monocyte chemoattractant protein-1 and tissue factor levels in patients with myocardial infarction." J. Am. Colt Cardiol. 34:983-988, 1999.

Sorbi, D. et al., "Elevated levels of 92-kd type IV collagenase (Matrix metalloproteinase 9) in giant cell arteritis." Arthritis Rheum. 39:1747-1753, 1996.

Squadrito, F. et al., "Thrombolytic therapy with urokinase reduces increased circulating endothelial adhesion molecules in acute myocardial infarction." Inflamm. Res. 45:14-19, 1996.

Steiner, M. et al., "Increased levels of soluble adhesion molecules in Type 2 (Non-insulin dependent) diabetes mellitus are independent of glycaemic control." Thromb. Haemost. 72:979-984, 1994.

Stockman, B.J. et al., "Secondary structure and topology of interleukin-1 receptor antagonist protein determined by heteronuclear three-dimensional NMR spectroscopy." Biochemistry 31:5237-5245, 1992.

Suefuji, H. et al., "Increased plasma tissue factor levels in acute myocardial infarction." Am. Heart J. 134:253-259, 1997.

Suga, M. et al., "Clinical significance of MCP-1 levels in BALF and serum in patients with interstitial lung diseases." Eur. Respir. J. 14:376-382, 1999.

Switalska, H.I. et al., "Radioimmunoassay of human platelet thrombospondin: Different patterns of thrombosponsin and β-thromboglobulin antigen secretion and clearance from the circulation." J. Lab. Clin. Med. 106:690-700, 1985.

Takahashi, H. et al., "Tissue factor in plasma of patients with disseminated intravascular coagulation." Am. J. Hematol. 46:333-337, 1994.

Takeda, I. et al., "Soluble P-selectin in the plasma of patients with connective tissue diseases." Int. Arch. Allergy Immunol. 105:128-134, 1994.

Tanaka et al., "Serum and urinary human heart fatty acid-binding protein in acute myocardial Infarction." Clin. Biochem., 24:195-201, 1991.

Tanaka, M. and Suzuki, A., "Hemostatic abnormalities in acute myocardial infarction as detected by specific blod markers." Thromb. Res. 76:289-298, 1994.

Tateyama et al., "Concentrations and molecular forms of human brain natriuretic peptide in plasma." Biochem. Biophys. Res. Commun., 185:760-7, 1992.

Tenaglia, A.N. et al., "Levels of expression of P-selectin, E-selectin, and intercellular adhesion molecule-1 in coronary atherectomy specimens from patients with stable and unstable angina pectoris." Am. J. Cardiol. 79:742-747, 1997.

Theroux and Fuster, "Acute coronary syndromes: Unstable angina and non-Q-wave myocardial Infarction." Circulation 97 :1195-1206, 1998.

Theroux, P. et al., "Fibrinopeptide A and platelet levels in unstable angina pectoris." Circulation 75:156-162, 1987.

Thygesen, et al., "Creatine kinase and creatine kinase B-subunit in stable and unstable angina pectoris." Eur. J. Clin. Invest., 16:1-4, 1986.

Tietz Textbook of Clinical Chemistry, 2nd edition, Carl Burtis and Edward Ashwood eds., W.B. Saunders and Company, p. 496.

Tohgi, 1-l. et al., "Coagulation-fibrinolysis abnormalities in acute and chronic phases of cerebral thrombosis and embolism." Stroke 21:1663-1667, 1990.

Tomoda, H. and Aoki, N., "Plasma soluble P-selectin in acute myocardial infarction: effects of coronary recanalization therapy." Angiology 49:807-813, 1988.

Tousoulis, D. et al., "Von Willebrand factor in patients evolving Q-wave versus non-Q-wave acute myocardial infarction." Int. J. Cardiol. 56:259-262, 1996.

Triebel, S. et al., "A 25 kDa α2-microglobulin-related protein is a component of the 125 kDa form of human gelatinase." FEBS Lett. 3 14:386-388, 1992.

Tsuji et al., "Human heart-type cytoplasmic fatty acid-binding protein in serum and urine during hyperacute myocardial infarction." Int. J. Cardiol., 41:209-217, 1993.

Ushiyama, S. et al., "Structural and functional characterization of monomeric soluble P-selectin and comparison with membrane P-selectin." J. Biol. Chem. 268:15229-15237, 1993.

Usui et al., "β-enolase in blood plasma during open heart surgery." Cardiovasc. Res., 23:737-740, 1989.

Usui et al., "S-100ao protein in serum during acute myocardial infarction." Clin. Chem. 36:639-641, 1990.

Usui et al., "S-100a0 protein in blood and urine during open-heart surgery." Clin. Chem., 35:1942-1944, 1989.

van den Dorpel, M.A. et al., "Low-density lipoprotein oxidation is increased in kidney transplant recipients." Transpl Int 9 Suppl. 1:S54-S57, 1996.

Van Nieuwenhoven et al., "Discrimination between myocardial and skeletal muscle injury by assessment of the plasma ratio of myoglobin over fatty acid-binding protein." Circulation 92:2848-2854, 1995.

Veerkamp and Maatman, "Cytoplasmic fatty acid-burning proteins: their structure and genes." Prog. Lipid Res., 34:17-52, 1995.

Wallace, J.M. et al., "The assessment of platelet derived growth factor concentration in post myocardial infarction and stable angina patients" Ann. Clin. Biochem. 35:236-241, 1998.

Wilkens et al., "The natriuretic-peptide family." Lancet, 349: 1307-1310, 1997.

Xu, Y. et al, "Lysophosphatidic acid as a potential biomarker for ovarian and other gynecologic cancers." JAMA 280:719-723, 1998.

Yazdani, S. et al., "Precutaneous interventions after the hemostatic profile of patients with unstable versus stable angina." J Am Coll Cardiol 30:1284-1287, 1997.

Yoshimoto et al., "Human heart-type cytoplasmic fatty acid-binding protein as an indicator of acute myocardial infarction." Heart Vessels, 10:304-309, 1995.

Yoshimura, T. et al., "Human monocyte chemoattractant protein-1 (MCP-1)." FEBS Lett. 244:487-493, 1989.

Zucker, S. et al., "Increased serum stromelysin-1 levels in systemic lupus erythematosus: lack of correlation with disease activity." J. Rheumatol. 26:78-80, 1999.

International Search Report in PCT Application No. PCT/US02/14219 dated Nov. 5, 2002.

Tateishi et al. Transient Increase in Plasma Brain (B-Type) Natriuretic Peptide after Percutaneous Transluminal Coronary Angioplasty. Clinical. Cardiology vol. 23; No. 10, pp. 776-780.

Database Medline, Accession No. 1999335795. Complementary DNA cloning, tissue distribution, and synthesis of canine brain natriuretic peptide. American Journal of Veterinary Research. Asano et al. Jul. 1999, vol. 60, No. 7, pp. 860-864.

Database Embase, Accession No. 2001129199. Non-viable myocardium, documented by TL-201 SPECT, is a main determinant of the increase in the secretion of Cardiac Natriuretic Peptides. Medecine Nucleaire. 2000, Hassan et al., vol. 24, No. 6, pp. 301-310, Abstract.

Christenson et al., "Standardization of Cardiac Troponin I Assays: Round Robin of Ten Candidate Reference Materials," *Clin. Chem.* 47:431-437 (2001).

*Robbins Pathologic Basis of Disease*, 6th Ed., (1999), chapter 13, "The Heart," p. 554.

American Heart Association web publication entitled *Myocardial Ischemia, Injury and Infarction*.

Myocardial Infraction Redefined-A consensus document of the Joint European Society of Cardiology/American College of Cardiology Committee for the Redefinition of Myocardial Infraction. *J. Am. Coll. Cardiol.*, 36: 959-969, 2000.

Fu and Van Eyk, "Proteomics and heart disease: identifying biomarkers of clinical utility" *Expert Rev. Proteomics* 3: 237-249 (2006).

Hassan et al., "Non-viable myocardium, documented by TL-201 SPECT, is a main determinant of the increase in the secretion of cardiac matriuretic peptides" Medecine Nucleaire, 2000, 24/6, pp. 301-310 (Database EMBASE Accession No. 2001129199 and English language translation).

Supplementary European Search Report—part of Communication dated Aug. 9, 2006 for EP Application No. 04760003,6-2404.

Allwords.com., Definition of "Appreciable".

Greenberg "Drug News and Perspectives", 1998, vol. 11, No. 5, pp. 265-270 (Abstract Only).

Hunter et al., "Analysis of Peptides Derived from Pro Atrial Natriuretic Peptide That Circulate in Man an Increase in Heart Disease", Scand J. Clin Lab Invest 56, 205-216 (1998).

Indik and Alpert, Detection of pulmonary embolism by D-dimer assay, spiral computed tomography, and magnetic resonance imaging. Prog. Cardiovasc. Dis. 42:261-272, 2000.

Mills et al., "Sustained Hemodynamic Effects of an Infusion of Nesiritide (Human b-Type Natriuretic Peptide) in Heart Failure", Journal of the American College of Cardiology, vol. 34, No. 1, pp. 155-62 (1999).

Mullins et al., CT and conventional and diffusion-weighted MR imaging in acute stroke: Study in 691 patients at presentations to the emergency department. Radiology, 224(2): 353-360, 2002.

Nakagawa et al., Plasma concentrations of brain natriuretic peptide in patients with acute ischemic stroke. Cerebrovasc Disease, 19:157-164, 2005.

NG and ILAG, Biomedical applications of protein chips, J. Cell. Mol. Med., 6:329-340, 2002.

"Tumor necrosis factor ligand superfamily member 12." Human Protein Reference Database, http://www.hprd.org/alternate?protein=04074&isoform_id=04074_1&isoform_name=Isoform_1, May 31, 2007.

Venugopal, "Cardiac Natriuretic Peptides—Hope or Hype?", Journal of Clinical Pharmacy and therapeutics, vol. 26, No. 1, 15-31 (2001).

Vesley et al., "Negative Feedback of Atrial Natriuretic Peptides", Journal of Clinical Endocrinology and Metabolism, vol. 78, No. 5, 1128-1134 (1994).

Yip et al., Time course and prognostic value of plasma levels of N-terminal pro-brain natriuretic peptide in patients after ischemic stroke. Circualtion Journal, 70:447-452, 2006.

\* cited by examiner

DIAGNOSTIC MARKERS OF ACUTE CORONARY SYNDROME AND METHODS OF USE THEREOF

This application is a Divisional of U.S. application Ser. No. 10/139,086, filed May 4, 2002, incorporated herein by reference in its entirety, which is related to and claims priority from U.S. Provisional Patent Application No. 60/288,871, filed on May 4, 2001; and U.S. Provisional Patent Application No. 60/315,642, filed on Aug. 28, 2001, each of which is hereby incorporated by reference in its entirety.

FIELD OF THE INVENTION

The present invention relates to the identification and use of diagnostic markers for acute coronary syndromes (ACS). In various aspects, the invention relates to methods for the early detection and differentiation of ACS and the identification of individuals at risk for adverse events upon presentation with ACS symptoms.

BACKGROUND OF THE INVENTION

The following discussion of the background of the invention is merely provided to aid the reader in understanding the invention and is not admitted to describe or constitute prior art to the present invention.

ACS is a manifestation of vascular injury to the heart, also referred to as myocardial injury or myocardial damage, that is commonly secondary to atherosclerosis or hypertension, and is the leading cause of death in the United States. ACS is commonly caused by occlusion associated with coronary artery disease cause by atherosclerotic plaque formation and progression to either further occlusion or fissure. ACS can be manifested as stable angina, unstable angina, or myocardial infarction.

The term "acute coronary syndromes" ("ACS") has been applied to a group of coronary disorders that result from ischemic insult to the heart. Patients with ACS form a heterogeneous group, with differences in pathophysiology, clinical presentation, and risk for adverse events. Such patients present to the physician with conditions that span a continuum that includes unstable angina, non-ST-elevation non-Q wave myocardial infarction ("NST"-"MI"), ST-elevation non-Q wave MI, and transmural (Q-wave) MI. ACS is believed to result largely from thrombus deposition and growth within one or more coronary arteries, resulting in a partial or complete occlusion of the artery, and frequently involves rupture of the plaque, resulting in an ischemic injury. ACS may also be precipitated by a coronary vasospasm or increased myocardial demand. For review, see, e.g., Davies, Clin. Cardiol. 20 (Supp. I): I2-I7 (1997).

The seriousness of ACS is underlined by the morbidity and mortality that follow the ischemic insult. For example, workers have estimated that within four to six weeks of presentation with ACS, the risk of death or a subsequent myocardial infarction (MI) is 8-14%, and the rate of death, MI, or refractory ischemia is 15-25% (Theroux and Fuster, Circulation 97: 1195-1206, 1998). Given that the total number of deaths in the U.S. from acute MI is about 600,000, the search within the art for information that relates to the diagnosis, prognosis, and management of ACS has understandably been extensive. Several potential markers that may provide such information in certain patient populations have been identified, including circulating cardiac troponin levels (see, e.g., Antman et al., N. Eng. J. Med. 335: 1342-9, 1996; see also U.S. Pat. Nos. 6,147,688, 6,156,521, 5,947,124, and 5,795,725, each of which is hereby incorporated by reference in its entirety), ST-segment depression (see, e.g., Savonitto et al., JAMA 281: 707-13, 1999), circulating creatine kinase levels (see, e.g., Alexander et al., Circulation (Suppl.) 1629, 1998), and circulating c-reactive protein levels (see, e.g., Morrow et al., J. Am. Coll. Cardiol. 31: 1460-5, 1998).

Stable angina is characterized by constricting chest pain that occurs upon exertion or stress, and is relieved by rest or sublingual nitroglycerin. Unstable angina is characterized by constricting chest pain at rest that is relieved by sublingual nitroglycerin. Anginal chest pain is usually relieved by sublingual nitroglycerin, and the pain usually subsides within 30 minutes. Myocardial infarction is characterized by constricting chest pain lasting longer than 30 minutes that can be accompanied by diagnostic electrocardiography (ECG) Q waves. Unstable angina is thought to represent the clinical state between stable angina and myocardial infarction, and is commonly associated with atherosclerotic plaque rupture and thrombus formation. In this regard, atherosclerotic plaque rupture is the most common cause of myocardial infarction.

Inflammation occurs during stable angina, and markers of plaque rupture, platelet activation, and early thrombosis can be used to identify and monitor the progressing severity of unstable angina. The myocardial damage caused during an anginal attack is, by definition, reversible, while damage caused during a myocardial infarction is irreversible. According to this model, a specific marker of myocardial injury can be used to identify myocardial infarction. The progression of coronary artery disease from mild unstable angina to severe unstable angina and myocardial infarction is related to plaque instability and the degree of arterial occlusion. This progression can occur slowly, as stable plaques enlarge and become more occlusive, or it can occur rapidly, as unstable plaques rupture, causing platelet activation and occlusive thrombus formation. Because myocardial infarction most frequently shares the same pathophysiology as unstable angina, it is possible that the only distinction between these two events is the reversibility of myocardial damage. However, since the only distinction between severe unstable angina and mild myocardial infarction is based on clinical judgement, markers of myocardial damage may also appear in the peripheral circulation of patients diagnosed as having unstable angina.

Current diagnostic methods for ACS commonly include clinical symptoms, electrocardiography (ECG), and the measurement of cardiac markers in the peripheral circulation. Angiography is also used in cases of severe chest pain usually associated with unstable angina and acute myocardial infarction (AMI). Patients with ACS frequently have constricting chest pain that often radiates to the neck, jaw, shoulders, or down the inside of the left or both arms and can have accompanying symptoms of dyspnea, diaphoresis, palpitations, light-headedness, and nausea. Myocardial ischemia can produce diagnostic ECG changes including Q waves and ST segment changes. Elevations of the plasma concentration of cardiac enzymes may reflect the degree of cardiac tissue necrosis associated with severe unstable angina and myocardial infarction.

Accordingly, there is a present need in the art for a rapid, sensitive and specific diagnostic assay for ACS that can also differentiate the type of ACS and identify those individuals at risk for delayed adverse events. Such a diagnostic assay would greatly increase the number of patients that can receive beneficial treatment and therapy, and reduce the costs associated with incorrect diagnosis.

SUMMARY OF THE INVENTION

The present invention relates to the identification and use of diagnostic and/or prognostic markers for ACS, ischemia, and/or necrosis. The methods and compositions described herein can meet the need in the art for a rapid, sensitive and specific diagnostic assay to be used in the diagnosis, differentiation and prognosis of various forms of ACS. Moreover, the methods and compositions of the present invention can also be used to facilitate the treatment of ACS patients and the development of additional diagnostic indicators.

The terms "ischemia and ischemic" relate to damage to the myocardium as a result of a reduction of blood flow to the heart. The terms "angina pectoris", "stable angina", "unstable angina", "silent ischemia" are generally related to myocardial ischemia. One skilled in the art will recognize these terms, which are described in "The Merck Manual of Diagnosis and Therapy" Seventeenth Edition, 1999, Ed. Keryn A. G. Lane, pp. 1662-1668, incorporated by reference only. The term ischemia is also related to what one skilled in the art would consider as minor myocardial injury or damage. The term ischemia is further described in the Journal of the American College of Cardiology 36, 959-969 (2000), incorporated by reference only.

The terms "necrosis and necrotic" relate to myocardial cell death as a result of a reduction or stoppage of blood flow to the heart. Myocardial necrosis is a condition of the heart which is more severe than myocardial ischemia. The term "myocardial infarction" is generally related to myocardial necrosis. One skilled in the art will recognize these terms, which are described in "The Merck Manual of Diagnosis and Therapy" Seventeenth Edition, 1999, Ed. Keryn A. G. Lane, pp. 1668-1677, incorporated by reference only. The term necrosis is also related to what one skilled in the art would consider as major myocardial injury or damage. The terms myocardial infarction and necrosis are further described in the Journal of the American College of Cardiology 36, 959-969 (2000), incorporated by reference only.

In various aspects, the invention relates to materials and procedures for identifying markers that are associated with the diagnosis, prognosis, or differentiation of ACS in a patient; to using such markers in diagnosing and treating a patient and/or to monitor the course of a treatment regimen; and for screening compounds and pharmaceutical compositions that might provide a benefit in treating or preventing such conditions.

In a first aspect, the invention features methods of diagnosing ACS by analyzing a test sample obtained from a patient for the presence or amount of one or more markers for myocardial injury. These methods can include identifying one or more markers, the presence or amount of which is associated with the diagnosis, prognosis, or differentiation of ACS. Once such a marker(s) is identified, the level of such a marker(s) in a patient sample can be measured. In certain embodiments, these markers can be compared to a diagnostic level that is associated with the diagnosis, prognosis, or differentiation of ACS. By correlating the patient level to the diagnostic level, the presence or absence of ACS, and the probability of future adverse outcomes in a patient may be rapidly and accurately determined.

For purposes of the following discussion, the methods described as applicable to the diagnosis and prognosis of myocardial infarction generally may be considered applicable to the diagnosis and prognosis of stable angina and unstable angina.

In certain embodiments, a plurality of markers are combined to increase the predictive value of the analysis in comparison to that obtained from the markers individually or in smaller groups. Preferably, one or more specific markers for myocardial injury can be combined with one or more non-specific markers for myocardial injury to enhance the predictive value of the described methods.

The term "marker" as used herein refers to molecules to be used as targets for screening patient test samples. Examples of such molecular targets are proteins or polypeptides. "Proteins or polypeptides" used as markers in the present invention are contemplated to include any fragments thereof, in particular, immunologically detectable fragments. One of skill in the art would recognize that proteins which are released by cells of the heart which become damaged during vascular injury could become degraded or cleaved into such fragments. Additionally, certain markers are synthesized in an inactive form, which may be subsequently activated by proteolysis. Examples of such markers are described hereinafter. The term "related marker" as used herein refers to one or more fragments of a particular marker that may be detected as a surrogate for the marker itself.

To date, BNP and BNP related peptides have not been used as markers of myocardial ischemia. Additionally, other markers of various pathological processes including inflammation, coagulation, and plaque rupture have not been used as subsets of a larger panel of markers of myocardial ischemia. Preferred markers of the invention can aid in the diagnosis, differentiation, and prognosis of patients with myocardial infarction, unstable angina, and stable angina.

The term "test sample" as used herein refers to a biological sample obtained for the purpose of diagnosis, prognosis, or evaluation. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components.

The term "specific marker of myocardial injury" as used herein refers to molecules that are typically associated with cardiac tissue, and which can be correlated with a cardiac injury, but are not correlated with other types of injury. Such specific markers of cardiac injury include annexin V, B-type natriuretic peptide, β-enolase, cardiac troponin I (free and/or complexed), cardiac troponin T (free and/or complexed), creatine kinase-MB, glycogen phosphorylase-BB, heart-type fatty acid binding protein, phosphoglyceric acid mutase-MB, and S-100ao. These specific markers are described in detail hereinafter.

The term "non-specific marker of myocardial injury" as used herein refers to molecules that are typically general markers of coagulation and hemostasis or acute phase reactants. Such markers may be elevated in the event of cardiac injury, but may also be elevated due to non-cardiac events. Factors in the activation of platelets and the mechanisms of coagulation include β-thromboglobulin, D-dimer, fibrinopeptide A, platelet-derived growth factor, plasmin-α-2-antiplasmin complex, platelet factor 4, prothrombin fragment 1+2, P-selectin, thrombin-antithrombin III complex, thrombus precursor protein, tissue factor, and von Willebrand factor. These non-specific markers are described in detail hereinafter.

The term "acute phase reactants" as used herein refers to proteins whose concentrations are elevated in response to stressful or inflammatory states that occur during various insults that include infection, injury, surgery, trauma, tissue necrosis, and the like. Acute phase reactant expression and serum concentration elevations are not specific for the type of insult, but rather as a part of the homeostatic response to the insult.

All acute phase reactants are produced in response to insult, perhaps in order to handle extensive insult, even though some components may not be needed. Examples of classical acute phase proteins include C-reactive protein, ceruloplasmin, fibrinogen, $\alpha 1$-acid glycoprotein, $\alpha 1$-antitrypsin, and haptoglobin. Various cytokines and related molecules such as insulin-like growth factor-1, interleukin-1$\beta$, interleukin-1 receptor antagonist, interleukin-6, interleukin-8, transforming growth factor $\beta$, monocyte chemotactic protein-1, and tumor necrosis factor $\alpha$ are components of the inflammatory response that are also intimately involved in the acute phase reaction. Such cytokines are released into the bloodstream from the site of insult and are capable of themselves inducing expression of other acute phase proteins.

Other non-specific markers of myocardial injury include markers of atheroslcerotic plaque rupture. An atherosclerotic plaque consists of accumulated lipids, smooth muscle cells, connective tissue, and glycosaminoglycans. Vessels containing such plaques have reduced systolic expansion, abnormally rapid wave propagation, and progressively reduced elasticity as plaque formation progresses. A plaque may progress to severe stenosis and total arterial occlusion. Some plaques are stable, but others which are rich in lipids and inflammatory cells typically have a thin fibrous cap and may undergo spontaneous rupture. These unstable plaques are more closely associated with the onset of an acute ischemic event. Therefore, markers of atherosclerotic plaque rupture may be useful in the diagnosis and evaluation of potential ACS victims. Such markers of atherosclerotic plaque rupture included human neutrophil elastase, inducible nitric oxide synthase, lysophosphatidic acid, malondialdehyde-modified low-density lipoprotein, matrix metalloproteinase-1, matrix metalloproteinase-2, matrix metalloproteinase-3, and matrix metalloproteinase-9.

Other non-specific markers of myocardial injury may include caspase-3, hemoglobin $\alpha_2$, soluble intercellular adhesion molecule-1 and soluble vascular cell adhesion molecule-1.

The phrase "diagnosis" as used herein refers to methods by which the skilled artisan can estimate and even determine whether or not a patient is suffering from a given disease or condition. The skilled artisan often makes a diagnosis on the basis of one or more diagnostic indicators, i.e., a marker, the presence, absence, or amount of which is indicative of the presence, severity, or absence of the condition.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing a future event in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. Preferred prognostic markers can predict the onset of delayed adverse events in a patient, or the chance of future ACS.

The term "correlating," as used herein in reference to the use of diagnostic and prognostic indicators, refers to comparing the presence or amount of the indicator in a patient to its presence or amount in persons known to suffer from, or known to be at risk of, a given condition; or in persons known to be free of a given condition, i.e. "normal individuals". For example, a marker level in a patient sample can be compared to a level known to be associated with a specific type of ACS. The sample's marker level is said to have been correlated with a diagnosis; that is, the skilled artisan can use the marker level to determine whether the patient suffers from a specific type of ACS, and respond accordingly. Alternatively, the sample's marker level can be compared to a marker level known to be associated with a good outcome (e.g., the absence of ACS), such as an average level found in a population of normal individuals.

In certain embodiments, a diagnostic or prognostic indicator is correlated to a condition or disease by merely its presence or absence. In other embodiments, a threshold level of a diagnostic or prognostic indicator can be established, and the level of the indicator in a patient sample can simply be compared to the threshold level. A preferred threshold level for markers of the present invention is about 25 pg/mL, about 50 pg/mL, about 60 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, and about 2500 pg/mL. The term "about" in this context refers to $\pm 10\%$.

In yet other embodiments, multiple determination of one or more diagnostic or prognostic markers can be made, and a temporal change in the marker can be used to determine a diagnosis or prognosis. For example, a diagnostic indicator may be determined at an initial time, and again at a second time. In such embodiments, an increase in the marker from the initial time to the second time may be diagnostic of a particular type of ACS, or a given prognosis. Likewise, a decrease in the marker from the initial time to the second time may be indicative of a particular type of ACS, or a given prognosis. Furthermore, the degree of change of one or more markers may be related to the severity of ACS and future adverse events.

In yet another embodiment, multiple determination of one or more diagnostic or prognostic markers can be made, and a temporal change in the marker can be used to monitor the efficacy of appropriate therapies. In such an embodiment, one might expect to see a decrease or an increase in the marker(s) over time during the course of effective therapy.

The skilled artisan will understand that, while in certain embodiments comparative measurements are made of the same diagnostic marker at multiple time points, one could also measure a given marker at one time point, and a second marker at a second time point, and a comparison of these markers may provide diagnostic information.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is predictably more or less likely to occur based on the presence, absence or levels of test markers. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting the condition, the chance of a given outcome may be about 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to ±1%.

The skilled artisan will understand that associating a prognostic indicator with a predisposition to an adverse outcome is a statistical analysis. For example, a marker level of greater than 80 pg/mL may signal that a patient is more likely to suffer from an adverse outcome than patients with a level less than or equal to 80 pg/mL, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

In other embodiments, a threshold degree of change in the level of a prognostic or diagnostic indicator can be established, and the degree of change in the level of the indicator in a patient sample can simply be compared to the threshold degree of change in the level. A preferred threshold change in the level for markers of the invention is about 5%, about 10%, about 15%, about 20%, about 25%, about 30%, about 50%, about 75%, about 100%, and about 150%. The term "about" in this context refers to ±10%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In yet another aspect, the invention relates to methods for determining a treatment regimen for use in a patient diagnosed with ACS. The methods preferably comprise determining a level of one or more diagnostic or prognostic markers as described herein, and using the markers to determine a diagnosis for a patient. One or more treatment regimens that improve the patient's prognosis by reducing the increased disposition for an adverse outcome associated with the diagnosis can then be used to treat the patient. Such methods may also be used to screen pharmacological compounds for agents capable of improving the patients prognosis as above.

In a further aspect, the invention relates to kits for determining the diagnosis or prognosis of a patient. These kits preferably comprise devices and reagents for measuring one or more marker levels in a patient sample, and instructions for performing the assay. Optionally, the kits may contain one or more means for converting marker level(s) to a prognosis. Such kits preferably contain sufficient reagents to perform one or more such determinations.

DETAILED DESCRIPTION OF THE INVENTION

In accordance with the present invention, there are provided methods and compositions for the identification and use of markers that are associated with the diagnosis, prognosis, or differentiation of ACS in a patient. Such markers can be used in diagnosing and treating a patient and/or to monitor the course of a treatment regimen; and for screening compounds and pharmaceutical compositions that might provide a benefit in treating or preventing such conditions.

Myocardial ischemia is caused by an imbalance of myocardial oxygen supply and demand. Specifically, demand exceeds supply due to inadequate blood supply. The heart accounts for a small percentage of total body weight, but is responsible for 7% of body oxygen consumption. Cardiac tissue metabolism is highly aerobic and has very little reserve to compensate for inadequate blood supply. When the blood supply is reduced to levels that are inadequate for myocardial demand, the tissue rapidly becomes hypoxic and toxic cellular metabolites can not be removed. Myocardial cells rapidly use oxygen supplies remaining in the local microvasculature, and the length of time that aerobic metabolism continues is indirectly proportional to the degree of arterial occlusion. Once the oxygen supply has been exhausted, oxidative phosphorylation can not continue because oxygen is no longer available as an electron acceptor, pyruvate can not be converted to acetyl coenzyme A and enter the citric acid cycle. Myocardial metabolism switches to anaerobic metabolism using glycogen and glucose stores, and pyruvate is fermented to lactate. Lactate accumulation is the primary cause of chest pain in individuals with ACS. As ischemia continues, cardiac tissue becomes more acidic as lactate and other acidic intermediates accumulate, ATP levels decrease, and available energy sources are depleted. Cardiac tissue can recover if it is reperfused 15-20 minutes after an ischemic event. After the cellular glycogen stores have been depleted, the cell gradually displays features of necrosis, including mitochondrial swelling and loss of cell membrane integrity. Upon reperfusion, these damaged cells die, possibly as a result of the cell's inability to maintain ionic equilibrium. A loss of membrane integrity causes the cell's cytosolic contents to be released into the circulation.

Stable angina, unstable angina, and myocardial infarction all share one common feature: constricting chest pain associated with myocardial ischemia. Angina is classified as stable or unstable through a physician's interpretation of clinical symptoms, with or without diagnostic ECG changes. The classification of angina as "stable" or "unstable" does not refer to the stability of the plaque itself, but rather, the degree of exertion that is required to elicit chest pain. Most notably, the classification of chest pain as stable or unstable angina (or even mild myocardial infarction) in cases other than definitive myocardial infarction is completely subjective. The diagnosis, and in this case the distinction, is made not by angiography, which may quantify the degree of arterial occlusion, but rather by a physician's interpretation of clinical symptoms.

Stable angina is characterized by constricting chest pain that occurs upon exertion or stress, and is relieved by rest or sublingual nitroglycerin. Coronary angiography of patients with stable angina usually reveals 50-70% obstruction of at least one coronary artery. Stable angina is usually diagnosed by the evaluation of clinical symptoms and ECG changes. Patients with stable angina may have transient ST segment abnormalities, but the sensitivity and specificity of these changes associated with stable angina are low.

Unstable angina is characterized by constricting chest pain at rest that is relieved by sublingual nitroglycerin. Anginal chest pain is usually relieved by sublingual nitroglycerin, and the pain usually subsides within 30 minutes. There are three classes of unstable angina severity: class I, characterized as new onset, severe, or accelerated angina; class II, subacute angina at rest characterized by increasing severity, duration, or requirement for nitroglycerin; and class III, characterized as acute angina at rest. Unstable angina represents the clinical state between stable angina and AMI and is thought to be primarily due to the progression in the severity and extent of atherosclerosis, coronary artery spasm, or hemorrhage into non-occluding plaques with subsequent thrombotic occlusion. Coronary angiography of patients with unstable angina usually reveals 90% or greater obstruction of at least one coronary artery, resulting in an inability of oxygen supply to meet even baseline myocardial oxygen demand. Slow growth of stable atherosclerotic plaques or rupture of unstable atherosclerotic plaques with subsequent thrombus formation can cause unstable angina. Both of these causes result in critical narrowing of the coronary artery. Unstable angina is usually associated with atherosclerotic plaque rupture, platelet activation, and thrombus formation. Unstable angina is usually diagnosed by clinical symptoms, ECG changes, and changes in cardiac markers (if any). Treatments for patients with unstable angina include nitrates, aspirin, GPIIb/IIIa inhibitors, heparin, and beta-blockers. Thrombolytic therapy has not been demonstrated to be beneficial for unstable angina patients, and calcium channel blockers may have no effect. Patients may also receive angioplasty and stents. Finally, patients with unstable angina are at risk for developing AMI.

Myocardial infarction is characterized by constricting chest pain lasting longer than 30 minutes that can be accompanied by diagnostic ECG Q waves. Most patients with AMI have coronary artery disease, and as many as 25% of AMI cases are "silent" or asymptomatic infarctions, and individuals with diabetes tend to be more susceptible to silent infarctions. Population studies suggest that 20-60% of nonfatal myocardial infarctions are silent infarctions that are not recognized by the patient. Atypical clinical presentations of AMI can include congestive heart failure, angina pectoris without a severe or prolonged attack, atypical location of pain, central nervous system manifestations resembling stroke, apprehension and nervousness, sudden mania or psychosis, syncope, weakness, acute indigestion, and peripheral embolization. AMI is usually diagnosed by clinical symptoms, ECG changes, and elevations of cardiac proteins, most notably cardiac troponin, creatine kinase-MB and myoglobin. Treatments of AMI have improved over the past decade, resulting in improved patient outcome and a 30% decrease in the death rate associated with AMI. Treatment of AMI patients is accomplished by administering agents that limit infarct size and improve outcome by removing occlusive material, increasing the oxygen supply to cardiac tissue, or decreasing the oxygen demand of cardiac tissue. Treatments can include the following: supplemental oxygen, aspirin, GPIIb/IIIa inhibitors, heparin, thrombolytics (tPA), nitrates (nitroglycerin), magnesium, calcium channel antagonists, β-adrenergic receptor blockers, angiotensin-converting enzyme inhibitors, angioplasty (PTCA), and intraluminal coronary artery stents.

The 30 minute time point from chest pain onset is thought to represent the window of reversible myocardial damage caused by ischemia. Stable angina and unstable angina are characterized angiographically as 50-70% and 90% or greater arterial occlusion, respectively, and myocardial infarction is characterized by complete or nearly complete occlusion. A common misconception is that stable angina and unstable angina refer to plaque stability, or that they, along with myocardial infarction, are separate diseases. Because stable angina often progresses to unstable angina, and unstable angina often progresses to myocardial infarction, stable angina, unstable angina, and myocardial infarction can all be characterized as coronary artery disease of varying severity. Recently, the following physiological model of coronary artery disease progression has been proposed: Inflammation→Plaque Rupture→Platelet Activation→Early Thrombosis→Early Necrosis. This model is designed to fit the theory that inflammation occurs during stable angina, and that markers of plaque rupture, platelet activation, and early thrombosis can be used to identify and monitor the progressing severity of unstable angina. The myocardial damage caused during an anginal attack is, by definition, reversible, while damage caused during a myocardial infarction is irreversible. Therefore, there are two proposed break points in this model for the discrimination of stable angina, unstable angina, and AMI. The first occurs between inflammation and plaque rupture, with the theory that plaque rupture does not occur in stable angina. The second occurs between early thrombosis and early necrosis, with the theory that myocardial damage incurred during unstable angina is reversible. It is important to realize that these events, with the exception of early myocardial necrosis, can be associated with all forms of coronary artery disease, and that progression along this diagnostic pathway does not necessarily indicate disease progression. The progression of coronary artery disease from mild unstable angina to severe unstable angina and myocardial infarction is related to plaque instability and the degree of arterial occlusion. This progression can occur slowly, as stable plaques enlarge and become more occlusive, or it can occur rapidly, as unstable plaques rupture, causing platelet activation and occlusive thrombus formation. Because myocardial infarction most frequently shares the same pathophysiology as unstable angina, it is possible that the only distinction between these two events is the reversibility of myocardial damage. By definition, unstable angina causes reversible damage, while myocardial infarction causes irreversible damage. There have been published reports that indicate the presence of myocardial necrosis in patients with unstable angina. By definition, these patients may actually be experiencing early AMI. Nevertheless, even if these patients are diagnosed with unstable angina instead of early AMI, the high degree of severity suggests that they will benefit greatly from early aggressive treatment. Myocardial ischemia is the major determinant in the pathogenesis of stable angina, unstable angina, and myocardial infarction, and they should not be thought of as individual diseases. Rather, they reflect the increasing severity of myocardial damage from ischemia.

The Coagulation Cascade in ACS

There are essentially two mechanisms that are used to halt or prevent blood loss following vessel injury. The first mechanism involves the activation of platelets to facilitate adherence to the site of vessel injury. The activated platelets then aggregate to form a platelet plug that reduces or temporarily stops blood loss. The processes of platelet aggregation, plug formation and tissue repair are all accelerated and enhanced by numerous factors secreted by activated platelets. Platelet aggregation and plug formation is mediated by the formation of a fibrinogen bridge between activated platelets. Concurrent activation of the second mechanism, the coagulation cascade, results in the generation of fibrin from fibrinogen and the formation of an insoluble fibrin clot that strengthens the platelet plug.

The coagulation cascade is an enzymatic pathway that involves numerous serine proteinases normally present in an inactive, or zymogen, form. The presence of a foreign surface in the vasculature or vascular injury results in the activation of the intrinsic and extrinsic coagulation pathways, respectively. A final common pathway is then followed, which results in the generation of fibrin by the serine proteinase thrombin and, ultimately, a crosslinked fibrin clot. In the coagulation cascade, one active enzyme is formed initially, which can activate other enzymes that active others, and this process, if left unregulated, can continue until all coagulation enzymes are activated. Fortunately, there are mechanisms in place, including fibrinolysis and the action of endogenous proteinase inhibitors that can regulate the activity of the coagulation pathway and clot formation.

Fibrinolysis is the process of proteolytic clot dissolution. In a manner analogous to coagulation, fibrinolysis is mediated by serine proteinases that are activated from their zymogen form. The serine proteinase plasmin is responsible for the degradation of fibrin into smaller degradation products that are liberated from the clot, resulting in clot dissolution. Fibrinolysis is activated soon after coagulation in order to regulate clot formation. Endogenous serine proteinase inhibitors also function as regulators of fibrinolysis.

Platelets are round or oval disks with an average diameter of 2-4 μm that are normally found in blood at a concentration of 200,000-300,000/μl. They play an essential role in maintaining hemostasis by maintaining vascular integrity, initially stopping bleeding by forming a platelet plug at the site of vascular injury, and by contributing to the process of fibrin formation to stabilize the platelet plug. When vascular injury occurs, platelets adhere to the site of injury and each other and are stimulated to aggregate by various agents released from adherent platelets and injured endothelial cells. This is followed by the release reaction, in which platelets secrete the contents of their intracellular granules, and formation of the platelet plug. The formation of fibrin by thrombin in the coagulation cascade allows for consolidation of the plug, followed by clot retraction and stabilization of the plug by crosslinked fibrin. Active thrombin, generated in the concurrent coagulation cascade, also has the ability to induce platelet activation and aggregation.

The coagulation cascade can be activated through either the extrinsic or intrinsic pathways. These enzymatic pathways share one final common pathway. The result of coagulation activation is the formation of a crosslinked fibrin clot. Fibrinolysis is the process of proteolytic clot dissolution that is activated soon after coagulation activation, perhaps in an effort to control the rate and amount of clot formation. Urokinase-type plasminogen activator (uPA) and tissue-type plasminogen activator (tPA) proteolytically cleave plasminogen, generating the active serine proteinase plasmin. Plasmin proteolytically digests crosslinked fibrin, resulting in clot dissolution and the production and release of fibrin degradation products.

The first step of the common pathway of the coagulation cascade involves the proteolytic cleavage of prothrombin by the factor Xa/factor Va prothrombinase complex to yield active thrombin. Thrombin is a serine proteinase that proteolytically cleaves fibrinogen to form fibrin, which is ultimately integrated into a crosslinked network during clot formation.

Exemplary Markers (i) Specific Markers for Myocardial Injury

Annexin V, also called lipocortin V, endonexin II, calphobindin I, calcium binding protein 33, placental anticoagulant protein I, thromboplastin inhibitor, vascular anticoagulant-α, and anchorin CII, is a 33 kDa calcium-binding protein that is an indirect inhibitor and regulator of tissue factor. Annexin V is composed of four homologous repeats with a consensus sequence common to all annexin family members, binds calcium and phosphatidyl serine, and is expressed in a wide variety of tissues, including heart, skeletal muscle, liver, and endothelial cells (Giambanco, I. et al., *J. Histochem. Cytochem.* 39:P 1189-1198, 1991; Doubell, A. F. et al., *Cardiovasc. Res.* 27:1359-1367, 1993). The normal plasma concentration of annexin V is <2 ng/ml (Kaneko, N. et al., *Clin. Chim. Acta* 251:65-80, 1996). The plasma concentration of annexin V is elevated in individuals with AMI (Kaneko, N. et al., *Clin. Chim. Acta* 251:65-80, 1996). Due to its wide tissue distribution, elevation of the plasma concentration of annexin V may be associated with any condition involving non-cardiac tissue injury. However, one study has found that plasma annexin V concentrations were not significantly elevated in patients with old myocardial infarction, chest pain syndrome, valvular heart disease, lung disease, and kidney disease (Kaneko, N. et al., *Clin. Chim. Acta* 251:65-80, 1996). These previous results require confirmation before the clinical utility of annexin V as an ACS marker can be determined. Annexin V is released into the bloodstream soon after AMI onset. The annexin V concentration in the plasma of AMI patients decreased from initial (admission) values, suggesting that it is rapidly cleared from the bloodstream (Kaneko, N. et al. *Clin. Chim. Acta* 251:65-80, 1996).

B-type natriuretic peptide (BNP), also called brain-type natriuretic peptide is a 32 amino acid, 4 kDa peptide that is involved in the natriuresis system to regulate blood pressure and fluid balance (Bonow, R. O., *Circulation* 93:1946-1950, 1996). The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species—NT pro-BNP, BNP-32, and the pre pro BNP—can circulate in human plasma (Tateyama et al., *Biochem. Biophys. Res. Commun.* 185: 760-7 (1992); Hunt et al., *Biochem. Biophys. Res. Commun.* 214: 1175-83 (1995)). The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP. Proteolytic degradation of BNP and of peptides related to BNP have also been described in the literature and these proteolytic fragments are also encompassed it the term "BNP related peptides". BNP and BNP-related peptides are predominantly found in the secretory granules of the cardiac ventricles, and are released from the heart in response to both ventricular volume expansion and pressure overload (Wilkins, M. et al., *Lancet* 349:1307-1310, 1997). Elevations of BNP are associated with raised atrial and pulmonary wedge pressures, reduced ventricular systolic and diastolic function, left ventricular hypertrophy, and myocardial infarction (Sagnella, G. A., *Clinical Science* 95:519-529, 1998). Furthermore, there are numerous reports of elevated BNP concentration associated with congestive heart failure and renal failure. While BNP and BNP-related peptides are likely not specific for ACS, they may be sensitive markers of ACS because they may indicate not only cellular damage due to ischemia, but also a perturbation of the natriuretic system associated with ACS. The term "BNP" as used herein refers to the mature 32-amino acid BNP molecule itself. As the skilled artisan will recognize, however, other markers related to BNP may also serve as diagnostic or prognostic indicators in patients with ACS. For example, BNP is synthesized as a 108-amino acid pre pro-BNP molecule that is proteolytically processed into a 76-amino acid "NT pro BNP" and the 32-amino acid BNP molecule. Because of its relationship to BNP, the concentration of NT pro-BNP molecule can also provide diagnostic or prognostic information in patients. The phrase "marker related to BNP or BNP related peptide" refers to any polypeptide that originates from the pre pro-BNP molecule, other than the 32-amino acid BNP molecule itself. Thus, a marker related to or associated with BNP includes the NT pro-BNP molecule, the pro domain, a fragment of BNP that is smaller than the entire 32-amino acid sequence, a fragment of pre pro-BNP other than BNP, and a fragment of the pro domain. One skilled in the art will also recognize that the circulation contains proteases which can proteolyze BNP and BNP related molecules and that these proteolyzed molecules (peptides) are also considered to be "BNP related" and are additionally subjects of this invention.

Enolase is a 78 kDa homo- or heterodimeric cytosolic protein produced from α, β, and γ subunits. Enolase catalyzes the interconversion of 2-phosphoglycerate and phosphoenolpyruvate in the glycolytic pathway. Enolase is present as αα, αβ, ββ, αγ, and γγ isoforms. The a subunit is found in most tissues, the β subunit is found in cardiac and skeletal muscle, and the γ subunit is found primarily in neuronal and neuroendocrine tissues. β-enolase is composed of αβ and ββ enolase, and is specific for muscle. The normal plasma concentration of β-enolase is <10 ng/ml (120 pM). β-enolase is elevated in the serum of individuals with AMI, but not in individuals with angina (Nomura, M. et al., *Br. Heart J.* 58:29-33, 1987; Herraez-Dominguez, M. V. et al., *Clin. Chim. Acta* 64:307-315, 1975). Further investigations into possible changes in plasma β-enolase concentration associated with unstable and stable angina need to be performed. The plasma concentration of β-enolase is elevated during heart surgery, muscular dystrophy, and skeletal muscle injury (Usui, A. et al., *Cardiovasc. Res.* 23:737-740, 1989; Kato, K. et al., *Clin. Chim. Acta* 131:75-85, 1983; Matsuda, H. et al., *Forensic Sci. Int.* 99:197-208, 1999). β-enolase is released into the bloodstream immediately following cardiac or skeletal muscle injury. The plasma β-enolase concentration was elevated to more than 150 ng/ml in the perioperative stage of cardiac surgery, and remained elevated for 1 week. Serum β-enolase concentrations peaked approximately 12-14 hours after the onset of chest pain and AMI and approached baseline after 1 week had elapsed from onset, with maximum levels approaching 1 µg/ml (Kato, K. et al., *Clin. Chim. Acta* 131:75-85, 1983; Nomura, M. et al., *Br. Heart J.* 58:29-33, 1987).

Troponin I (TnI) is a 25 kDa inhibitory element of the troponin complex, found in all striated muscle tissue. TnI binds to actin in the absence of $Ca^{2+}$, inhibiting the ATPase activity of actomyosin. A TnI isoform that is found in cardiac tissue (cTnI) is 40% divergent from skeletal muscle TnI, allowing both isoforms to be immunologically distinguished. The normal plasma concentration of cTnI is <0.1 ng/ml (4 pM). The plasma cTnI concentration is elevated in patients with AMI. Investigations into changes in the plasma cTnI concentration in patients with unstable angina have yielded mixed results, but cTnI is not elevated in the plasma of individuals with stable angina (Benamer, H. et al., *Am. J. Cardiol.* 82:845-850, 1998; Bertinchant, J. P. et al., *Clin. Biochem.* 29:587-594, 1996; Tanasijevic, M. J. et al., *Clin. Cardiol.* 22:13-16, 1999; Musso, P. et al., *J. Ital. Cardiol.* 26:1013-1023, 1996; Holvoet, P. et al., *JAMA* 281:1718-1721, 1999; Holvoet, P. et al., *Circulation* 98:1487-1494, 1998). The mixed results associated with unstable angina suggest that cTnI may be useful in determining the severity of unstable angina because the extent of myocardial ischemia is directly proportional to unstable angina severity. The plasma cTnI concentration may be elevated in conjunction with cardiac trauma, congestive heart failure, and cardiac surgery, non-ischemic dilated cardiomyopathy, muscular disorders, CNS disorders, HIV infection, chronic renal failure, sepsis, lung disease, and endocrine disorders (Khan, I. A. et al., *Am. J. Emerg. Med.* 17:225-229, 1999). This apparent non-specificity may be related to the quality and specificity of the antibodies used in the immunoassay. cTnI is released into the bloodstream following cardiac cell death. The plasma concentration of cTnI in patients with AMI is significantly elevated 4-6 hours after onset, peaks between 12-16 hours, and can remain elevated for one week. The release kinetics of cTnI associated with unstable angina may be similar. The measurement of specific forms of cardiac troponin, including free cardiac troponin I and complexes of cardiac troponin I with troponin C and/or T may provide the user with the ability to identify various stages of ACS.

Free and complexed cardiac-troponin T may be used in a manner analogous to that described above for cardiac troponin I. Cardiac troponin T complex may be useful either alone or when expressed as a ratio with total cardiac troponin I to provide information related to the presence of progressing myocardial damage. Ongoing ischemia may result in the release of the cardiac troponin TIC complex, indicating that higher ratios of cardiac troponin TIC:total cardiac troponin I may be indicative of continual damage caused by unresolved ischemia.

Creatine kinase (CK) is a 85 kDa cytosolic enzyme that catalyzes the reversible formation ADP and phosphocreatine from ATP and creatine. CK is a homo- or heterodimer composed of M and B chains. CK-MB is the isoform that is most specific for cardiac tissue, but it is also present in skeletal muscle and other tissues. The normal plasma concentration of CK-MB is <5 ng/ml. The plasma CK-MB concentration is significantly elevated in patients with AMI. Plasma CK-MB is not elevated in patients with stable angina, and investigation into plasma CK-MB concentration elevations in patients with unstable angina have yielded mixed results (Thygesen, K. et al., *Eur. J. Clin. Invest.* 16:1-4, 1986; Koukkunen, H. et al., *Ann. Med.* 30:488-496, 1998; Bertinchant, J. P. et al., *Clin. Biochem.* 29:587-594, 1996; Benamer, H. et al., *Am. J. Cardiol.* 82:845-850, 1998; Norregaard-Hansen, K. et al., *Eur. Heart J.* 13:188-193, 1992). The mixed results associated with unstable angina suggest that CK-MB may be useful in determining the severity of unstable angina because the extent of myocardial ischemia is directly proportional to unstable angina severity. Elevations of the plasma CK-MB concentration are associated with skeletal muscle injury and renal disease. CK-MB is released into the bloodstream following cardiac cell death. The plasma concentration of CK-MB in patients with AMI is significantly elevated 4-6 hours after onset, peaks between 12-24 hours, and returns to baseline after 3 days. The release kinetics of CK-MB associated with unstable angina may be similar.

Glycogen phosphorylase (GP) is a 188 kDa intracellular allosteric enzyme that catalyzes the removal of glucose (liberated as glucose-1-phosphate) from the nonreducing ends of glycogen in the presence of inorganic phosphate during glycogenolysis. GP is present as a homodimer, which associates with another homodimer to form a tetrameric enzymatically active phosphorylase A. There are three isoforms of GP that can be immunologically distinguished. The BB isoform is found in brain and cardiac tissue, the MM isoform is found in skeletal muscle and cardiac tissue, and the LL isoform is predominantly found in liver (Mair, J. et al., Br. Heart J. 72:125-127, 1994). GP-BB is normally associated with the sarcoplasmic reticulum glycogenolysis complex, and this association is dependent upon the metabolic state of the myocardium (Mair, J., Clin. Chim. Acta 272:79-86, 1998). At the onset of hypoxia, glycogen is broken down, and GP-BB is converted from a bound form to a free cytoplasmic form (Krause, E. G. et al. Mol. Cell Biochem. 160-161:289-295, 1996). The normal plasma GP-BB concentration is <7 ng/ml (36 pM). The plasma GP-BB concentration is significantly elevated in patients with AMI and unstable angina with transient ST-T elevations, but not stable angina (Mair, J. et al., Br. Heart J. 72:125-127, 1994; Mair, J., Clin. Chim. Acta 272:79-86, 1998; Rabitzsch, G. et al., Clin. Chem. 41:966-978, 1995; Rabitzsch, G. et al., Lancet 341:1032-1033, 1993). Furthermore, GP-BB also can be used to detect perioperative AMI and myocardial ischemia in patients undergoing coronary artery bypass surgery (Rabitzsch, G. et al., Biomed. Biochim. Acta 46:S584-S588, 1987; Mair, P. et al., Eur. J. Clin. Chem. Clin. Biochem. 32:543-547, 1994). GP-BB has been demonstrated to be a more sensitive marker of unstable angina and AMI early after onset than CK-MB, cardiac tropopnin T, and myoglobin (Rabitzsch, G. et al., Clin. Chem. 41:966-978, 1995). Because it is also found in the brain, the plasma GP-BB concentration also may be elevated during ischemic cerebral injury. GP-BB is released into the bloodstream under ischemic conditions that also involve an increase in the permeability of the cell membrane, usually a result of cellular necrosis. GP-BB is significantly elevated within 4 hours of chest pain onset in individuals with unstable angina and transient ST-T ECG alterations, and is significantly elevated while myoglobin, CK-MB, and cardiac troponin T are still within normal levels (Mair, J. et al., Br. Heart J. 72:125-127, 1994). Furthermore, GP-BB can be significantly elevated 1-2 hours after chest pain onset in patients with AMI (Rabitzsch, G. et al., Lancet 341:1032-1033, 1993). The plasma GP-BB concentration in patients with unstable angina and AMI can exceed 50 ng/ml (250 pM) (Mair, J. et al., Br. Heart J. 72:125-127, 1994; Mair, J., Clin. Chim. Acta 272:79-86, 1998; Krause, E. G. et al., Mol. Cell Biochem. 160-161:289-295, 1996; Rabitzsch, G. et al., Clin. Chem. 41:966-978, 1995; Rabitzsch, G. et al., Lancet 341: 1032-1033, 1993). GP-BB appears to be a very sensitive marker of myocardial ischemia, with specificity similar to that of CK-BB. GP-BB plasma concentrations are elevated within the first 4 hours after AMI onset, which suggests that it may be a very useful early marker of myocardial damage. Furthermore, GP-BB is not only a more specific marker of cardiac tissue damage, but also ischemia, since it is released to an unbound form during cardiac ischemia and would not normally be released upon traumatic injury. This is best illustrated by the usefulness of GP-BB in detecting myocardial ischemia during cardiac surgery. GP-BB may be a very useful marker of early myocardial ischemia during AMI and severe unstable angina.

Heart-type fatty acid binding protein (H-FABP) is a cytosolic 15 kDa lipid-binding protein involved in lipid metabolism. Heart-type FABP antigen is found not only in heart tissue, but also in kidney, skeletal muscle, aorta, adrenals, placenta, and brain (Veerkamp, J. H. and Maatman, R. G., Prog. Lipid Res. 34:17-52, 1995; Yoshimoto, K. et al., Heart Vessels 10:304-309, 1995). Furthermore, heart-type FABP mRNA can be found in testes, ovary, lung, mammary gland, and stomach (Veerkamp, J. H. and Maatman, R. G., Prog. Lipid Res. 34:17-52, 1995). The normal plasma concentration of FABP is <6 ng/ml (400 pM). The plasma H-FABP concentration is elevated in patients with AMI and unstable angina (Ishii, J. et al., Clin. Chem. 43:1372-1378, 1997; Tsuji, R. et al., Int. J. Cardiol. 41:209-217, 1993). Furthermore, H-FABP may be useful in estimating infarct size in patients with AMI (Glatz, J. F. et al., Br. Heart J. 71:135-140, 1994). Myocardial tissue as a source of H-FABP can be confirmed by determining the ratio of myoglobin/FABP (grams/grams). A ratio of approximately 5 indicates that FABP is of myocardial origin, while a higher ratio indicates skeletal muscle sources (Van Nieuwenhoven, F. A. et al., Circulation 92:2848-2854, 1995). Because of the presence of H-FABP in skeletal muscle, kidney and brain, elevations in the plasma H-FABP concentration may be associated with skeletal muscle injury, renal disease, or stroke. H-FABP is released into the bloodstream following cardiac tissue necrosis. The plasma H-FABP concentration can be significantly elevated 1-2 hours after the onset of chest pain, earlier than CK-MB and myoglobin (Tsuji, R. et al., Int. J. Cardiol. 41:209-217, 1993; Van Nieuwenhoven, F. A. et al., Circulation 92:2848-2854, 1995; Tanaka, T. et al., Clin. Biochem. 24:195-201, 1991). Additionally, H-FABP is rapidly cleared from the bloodstream, and plasma concentrations return to baseline after 24 hours after AMI onset (Glatz, J. F. et al., Br. Heart J. 71:135-140, 1994; Tanaka, T. et al., Clin. Biochem. 24:195-201, 1991).

Phosphoglyceric acid mutase (PGAM) is a 57 kDa homo- or heterodimeric intracellular glycolytic enzyme composed of 29 kDa M or B subunits that catalyzes the interconversion of 3-phosphoglycerate to 2-phosphoglycerate in the presence of magnesium. Cardiac tissue contains isozymes MM, MB, and BB, skeletal muscle contains primarily PGAM-MM, and most other tissues contain PGAM-BB (Durany, N. and Carreras, J., Comp. Biochem. Physiol. B. Biochem. Mol. Biol. 114:217-223, 1996). Thus, PGAM-MB is the most specific isozyme for cardiac tissue. PGAM is elevated in the plasma of patients with AMI, but further studies need to be performed to determine changes in the plasma PGAM concentration associated with AMI, unstable angina and stable angina (Mair, J., Crit. Rev. Clin. Lab. Sci. 34:1-66, 1997). Plasma PGAM-MB concentration elevations may be associated with unrelated myocardial or possibly skeletal tissue damage. PGAM-MB is most likely released into the circulation following cellular necrosis. PGAM has a half-life of less than 2 hours in the bloodstream of rats (Grisolia, S. et al., Physiol. Chem. Phys. 8:37-52, 1976).

S-100 is a 21 kDa homo- or heterodimeric cytosolic $Ca^{2+}$-binding protein produced from α and β subunits. It is thought to participate in the activation of cellular processes along the $Ca^{2+}$-dependent signal transduction pathway (Bonfrer, J. M. et al., Br. J Cancer 77:2210-2214, 1998).

S-100ao (αα isoform) is found in striated muscles, heart and kidney, S-100a (αβ isoform) is found in glial cells, but not in Schwann cells, and S-100b (ββ isoform) is found in high concentrations in glial cells and Schwann cells, where it is a major cytosolic component (Kato, K. and Kimura, S., Biochim. Biophys. Acta 842:146-150, 1985; Hasegawa, S. et al., Eur. Urol. 24:393-396, 1993). The normal serum concentration of S-100ao is <0.25 ng/ml (12 pM), and its concentration may be influenced by age and sex, with higher concentrations in males and older individuals (Kikuchi, T. et al., Hinyokika Kiyo 36:1117-1123, 1990; Morita, T. et al., Nippon Hinyokika Gakkai Zasshi 81:1162-1167, 1990; Usui, A. et al., Clin. Chem. 36:639-641, 1990). The serum concentration of S-100ao is elevated in patients with AMI, but not in patients with angina pectoris with suspected AMI (Usui, A. et al., Clin. Chem. 36:639-641, 1990). Further investigation is needed to determine changes in the plasma concentration of S-100ao associated with unstable and stable angina. Serum S-100ao is elevated in the serum of patients with renal cell carcinoma, bladder tumor, renal failure, and prostate cancer, as well as in patients undergoing open heart surgery (Hasegawa, S. et al., Eur. Urol. 24:393-396, 1993; Kikuchi, T. et al., Hinyokika Kiyo 36:1117-1123, 1990; Morita, T. et al., Nippon Hinyokika Gakkai Zasshi 81:1162-1167, 1990; Usui, A. et al., Clin. Chem. 35:1942-1944, 1989). S-100ao is a cytosolic protein that will be released into the extracellular space following cell death. The serum concentration of S-100ao is significantly elevated on admission in patients with AMI, increases to peak levels 8 hours after admission, decreases and returns to baseline one week later (Usui, A. et al., Clin. Chem. 36:639-641, 1990). Furthermore, S-100ao appears to be significantly elevated earlier after AMI onset than CK-MB (Usui, A. et al., Clin. Chem. 36:639-641, 1990). The maximum serum S-100ao concentration can exceed 100 ng/ml. S-100ao may be rapidly cleared from the bloodstream by the kidney, as suggested by the rapid decrease of the serum S-100ao concentration of heart surgery patients following reperfusion and its increased urine concentration, but further investigation is needed to determine the kinetics of S-100ao release into and clearance from the bloodstream in the context of ACS (Usui, A. et al., Clin. Chem. 35:1942-1944, 1989). S-100ao is found in high concentration in cardiac tissue and appears to be a sensitive marker of cardiac injury. Major sources of non-specificity of this marker for ACS include skeletal muscle and renal tissue injury. S-100ao may be significantly elevated soon after AMI onset, and it may allow for the discrimination of AMI from unstable angina. Patients with angina pectoris and suspected AMI, indicating that they were suffering chest pain associated with an ischemic episode, did not have a significantly elevated S-100ao concentration. In spite of its risk of non-specificity, which appears to be no different from that of CK-MB and myoglobin, S-100ao may allow physicians to distinguish AMI from unstable angina.

(ii) Non-specific Markers for Myocardial Injury Related to Coagulation

Plasmin is a 78 kDa serine proteinase that proteolytically digests crosslinked fibrin, resulting in clot dissolution. The 70 kDa serine proteinase inhibitor α2-antiplasmin (α2AP) regulates plasmin activity by forming a covalent 1:1 stoichiometric complex with plasmin. The resulting ~150 kDa plasmin-α2AP complex (PAP), also called plasmin inhibitory complex (PIC) is formed immediately after α2AP comes in contact with plasmin that is activated during fibrinolysis. The normal serum concentration of PAP is <1 µg/ml (6.9 nM). Elevations in the serum concentration of PAP can be attributed to the activation of fibrinolysis. Elevations in the serum concentration of PAP may be associated with clot presence, or any condition that causes or is a result of fibrinolysis activation. These conditions can include atherosclerosis, disseminated intravascular coagulation, AMI, surgery, trauma, unstable angina, stroke, and thrombotic thrombocytopenic purpura. PAP is formed immediately following proteolytic activation of plasmin. PAP is a specific marker for fibrinolysis activation and the presence of a recent or continual hypercoagulable state. It is not specific for ACS and can be elevated in many other disease states.

β-thromboglobulin (βTG) is a 36 kDa platelet α granule component that is released upon platelet activation. The normal plasma concentration of βTG is <40 ng/ml (1.1 nM). Plasma levels of β-TG appear to be elevated in patients with unstable angina and AMI, but not stable angina (De Caterina, R. et al., Eur. Heart J. 9:913-922, 1988; Bazzan, M. et al., Cardiologia 34, 217-220, 1989). Plasma β-TG elevations also seem to be correlated with episodes of ischemia in patients with unstable angina (Sobel, M. et al., Circulation 63:300-306, 1981). Elevations in the plasma concentration of PTG may be associated with clot presence, or any condition that causes platelet activation. These conditions can include atherosclerosis, disseminated intravascular coagulation, surgery, trauma, and thrombotic thrombocytopenic purpura, and stroke (Landi, G. et al., Neurology 37:1667-1671, 1987). βTG is released into the circulation immediately after platelet activation and aggregation. It has a biphasic half-life of 10 minutes, followed by an extended 1 hour half-life in plasma (Switalska, H. I. et al., J. Lab. Clin. Med. 106:690-700, 1985). Plasma βTG concentration is reportedly elevated dring unstable angina and AMI, but these studies may not be completely reliable. Special precautions must be taken to avoid platelet activation during the blood sampling process. Platelet activation is common during regular blood sampling, and could lead to artificial elevations of plasma βTG concentration. In addition, the amount of βTG released into the bloodstream is dependent on the platelet count of the individual, which can be quite variable. Plasma concentrations of βTG associated with ACS can approach 70 ng/ml (2 nM), but this value may be influenced by platelet activation during the sampling procedure.

Platelet factor 4 (PF4) is a 40 kDa platelet α granule component that is released upon platelet activation. PF4 is a marker of platelet activation and has the ability to bind and neutralize heparin. The normal plasma concentration of PF4 is <7 ng/ml (175 pM). The plasma concentration of PF4 appears to be elevated in patients with AMI and unstable angina, but not stable angina (Gallino, A. et al., Am. Heart J. 112:285-290, 1986; Sakata, K. et al., Jpn. Circ. J. 60:277-284, 1996; Bazzan, M. et al., Cardiologia 34:217-220, 1989). Plasma PF4 elevations also seem to be correlated with episodes of ischemia in patients with unstable angina (Sobel, M. et al., Circulation 63:300-306, 1981). Elevations in the plasma concentration of PF4 may be associated with clot presence, or any condition that causes platelet activation. These conditions can include atherosclerosis, disseminated intravascular coagulation, surgery, trauma, thrombotic thrombocytopenic purpura, and acute stroke (Carter, A. M. et al., Arterioscler. Thromb. Vasc. Biol. 18:1124-1131, 1998). PF4 is released into the circulation immediately after platelet activation and aggregation. It has a biphasic half-life of 1 minute, followed by an extended 20 minute half-life in plasma. The half-life of PF4 in plasma can be extended to 20-40 minutes by the presence of heparin (Rucinski, B. et al., *Am. J. Physiol.* 251: H800-H807, 1986). Plasma PF4 concentration is reportedly elevated during unstable angina and AMI, but these studies may not be completely reliable. Special precautions must be taken to avoid platelet activation during the blood sampling process. Platelet activation is common during regular blood sampling, and could lead to artificial elevations of plasma PF4 concentration. In addition, the amount of PF4 released into the bloodstream is dependent on the platelet count of the individual, which can be quite variable. Plasma concentrations of PF4 associated with disease can exceed 100 ng/ml (2.5 nM), but it is likely that this value may be influenced by platelet activation during the sampling procedure.

Fibrinopeptide A (FPA) is a 16 amino acid, 1.5 kDa peptide that is liberated from amino terminus of fibrinogen by the action of thrombin. Fibrinogen is synthesized and secreted by the liver. The normal plasma concentration of FPA is <5 ng/ml (3.3 nM). The plasma FPA concentration is elevated in patients with AMI, unstable angina, and variant angina, but not stable angina (Gensini, G. F. et al., *Thromb. Res.* 50:517-525, 1988; Gallino, A. et al., *Am. Heart J.* 112:285-290, 1986; Sakata, K. et al., *Jpn. Circ. J.* 60:277-284, 1996; Theroux, P. et al., *Circulation* 75:156-162, 1987; Merlini, P. A. et al., *Circulation* 90:61-68, 1994; Manten, A. et al., *Cardiovasc. Res.* 40:389-395, 1998). Furthermore, plasma FPA may indicate the severity of angina (Gensini, G. F. et al., *Thromb. Res.* 50:517-525, 1988). Elevations in the plasma concentration of FPA are associated with any condition that involves activation of the coagulation pathway, including stroke, surgery, cancer, disseminated intravascular coagulation, nephrosis, and thrombotic thrombocytopenic purpura. FPA is released into the circulation following thrombin activation and cleavage of fibrinogen. Because FPA is a small polypeptide, it is likely cleared from the bloodstream rapidly. FPA has been demonstrated to be elevated for more than one month following clot formation, and maximum plasma FPA concentrations can exceed 40 ng/ml in active angina (Gensini, G. F. et al., *Thromb. Res.* 50:517-525, 1988; Tohgi, H. et al., *Stroke* 21:1663-1667, 1990).

Platelet-derived growth factor (PDGF) is a 28 kDa secreted homo- or heterodimeric protein composed of the homologous subunits A and/or B (Mahadevan, D. et al., *J. Biol. Chem.* 270:27595-27600, 1995). PDGF is a potent mitogen for mesenchymal cells, and has been implicated in the pathogenesis of atherosclerosis. PDGF is released by aggregating platelets and monocytes near sites of vascular injury. The normal plasma concentration of PDGF is <0.4 ng/ml (15 pM). Plasma PDGF concentrations are higher in individuals with AMI and unstable angina than in healthy controls or individuals with stable angina (Ogawa, H. et al., *Am. J. Cardiol.* 69:453-456, 1992; Wallace, J. M. et al., *Ann. Clin. Biochem.* 35:236-241, 1998; Ogawa, H. et al., *Coron. Artery Dis.* 4:437-442, 1993). Changes in the plasma PDGF concentration in these individuals is most likely due to increased platelet and monocyte activation. Plasma PDGF is elevated in individuals with brain tumors, breast cancer, and hypertension (Kurimoto, M. et al., *Acta Neurochir. (Wien)* 137:182-187, 1995; Seymour, L. et al., *Breast Cancer Res. Treat.* 26:247-252, 1993; Rossi, E. et al., *Am. J. Hypertens.* 11:1239-1243, 1998). Plasma PDGF may also be elevated in any pro-inflammatory condition or any condition that causes platelet activation including surgery, trauma, disseminated intravascular coagulation, and thrombotic thrombocytopenic purpura. PDGF is released from the secretory granules of platelets and monocytes upon activation. PDGF has a biphasic half-life of approximately 5 minutes and 1 hour in animals (Cohen, A. M. et al., *J. Surg. Res.* 49:447-452, 1990; Bowen-Pope, D. F. et al., *Blood* 64:458-469, 1984). The plasma PDGF concentration in ACS can exceed 0.6 ng/ml (22 pM) (Ogawa, H. et al., *Am. J. Cardiol.* 69:453-456, 1992). PDGF may be a sensitive and specific marker of platelet activation. In addition, it may be a sensitive marker of vascular injury, and the accompanying monocyte and platelet activation.

Prothrombin fragment 1+2 is a 32 kDa polypeptide that is liberated from the amino terminus of thrombin during thrombin activation. The normal plasma concentration of F1+2 is <32 ng/ml (1 nM). Reports from investigations of plasma F1+2 concentration elevations that are associated with ACS are conflicting. The plasma concentration of F1+2 is reportedly elevated in patients with AMI and unstable angina, but not stable angina, but the changes were not robust (Merlini, P. A. et al., *Circulation* 90:61-68, 1994). Other reports have indicated that there is no significant change in the plasma F1+2 concentration in cardiovascular disease (Biasucci, L. M. et al., *Circulation* 93:2121-2127, 1996; Manten, A. et al., *Cardiovasc. Res.* 40:389-395, 1998). The concentration of F1+2 in plasma can be elevated during any condition associated with coagulation activation, including stroke, surgery, trauma, thrombotic thrombocytopenic purpura, and disseminated intravascular coagulation. F1+2 is released into the bloodstream immediately upon thrombin activation. F1+2 has a half-life of approximately 90 minutes in plasma, and it has been suggested that this long half-life may mask bursts of thrombin formation (Biasucci, L. M. et al., *Circulation* 93:2121-2127, 1996).

P-selectin, also called granule membrane protein-140, GMP-140, PADGEM, and CD-62P, is a ~140 kDa adhesion molecule expressed in platelets and endothelial cells. P-selectin is stored in the alpha granules of platelets and in the Weibel-Palade bodies of endothelial cells. Upon activation, P-selectin is rapidly translocated to the surface of endothelial cells and platelets to facilitate the "rolling" cell surface interaction with neutrophils and monocytes. Membrane-bound and soluble forms of P-selectin have been identified. Soluble P-selectin may be produced by shedding of membrane-bound P-selectin, either by proteolysis of the extracellular P-selectin molecule, or by proteolysis of components of the intracellular cytoskeleton in close proximity to the surface-bound P-selectin molecule (Fox, J. E., *Blood Coagul. Fibrinolysis* 5:291-304, 1994). Additionally, soluble P-selectin may be translated from mRNA that does not encode the N-terminal transmembrane domain (Dunlop, L. C. et al., *J. Exp. Med.* 175:1147-1150, 1992; Johnston, G. I. et al., *J. Biol. Chem.* 265:21381-21385, 1990). Activated platelets can shed membrane-bound P-selectin and remain in the circulation, and the shedding of P-selectin can elevate the plasma P-selectin concentration by approximately 70 ng/ml (Michelson, A. D. et al., *Proc. Natl. Acad. Sci. U.S.A.* 93:11877-11882, 1996). Soluble P-selectin may also adopt a different conformation than membrane-bound P-selectin. Soluble P-selectin has a monomeric rod-like structure with a globular domain at one end, and the membrane-bound molecule forms rosette structures with the globular domain facing outward (Ushiyama, S. et al., *J. Biol. Chem.* 268: 15229-15237, 1993). Soluble P-selectin may play an important role in regulating inflammation and thrombosis by blocking interactions between leukocytes and activated platelets and endothelial cells (Gamble, J. R. et al., *Science* 249:414-417, 1990). The normal plasma concentration of soluble P-selectin is <200 ng/ml. Blood is normally collected using citrate as an anticoagulant, but some studies have used EDTA plasma with additives such as prostaglandin E to prevent platelet activation. EDTA may be a suitable anticoagulant that will yield results comparable to those obtained using citrate. Furthermore, the plasma concentration of soluble P-selectin may not be affected by potential platelet activation during the sampling procedure. The plasma soluble P-selectin concentration was significantly elevated in patients with AMI and unstable angina, but not stable angina, even following an exercise stress test (Ikeda, H. et al., *Circulation* 92:1693-1696, 1995; Tomoda, H. and Aoki, N., *Angiology* 49:807-813, 1998; Hollander, J. E. et al., *J. Am. Coll. Cardiol.* 34:95-105, 1999; Kaikita, K. et al., *Circulation* 92:1726-1730, 1995; Ikeda, H. et al., *Coron. Artery Dis.* 5:515-518, 1994). The sensitivity and specificity of membrane-bound P-selectin versus soluble P-selectin for AMI is 71% versus 76% and 32% versus 45% (Hollander, J. E. et al., *J. Am. Coll. Cardiol.* 34:95-105, 1999). The sensitivity and specificity of membrane-bound P-selectin versus soluble P-selectin for unstable angina+AMI is 71% versus 79% and 30% versus 35% (Hollander, J. E. et al., *J. Am. Coll. Cardiol.* 34:95-105, 1999). P-selectin expression is greater in coronary atherectomy specimens from individuals with unstable angina than stable angina (Tenaglia, A. N. et al., *Am. J. Cardiol.* 79:742-747, 1997). Furthermore, plasma soluble P-selectin may be elevated to a greater degree in patients with AMI than in patients with unstable angina. Plasma soluble and membrane-bound P-selectin also is elevated in individuals with non-insulin dependent diabetes mellitus and congestive heart failure (Nomura, S. et al., *Thromb. Haemost.* 80:388-392, 1998; O'Connor, C. M. et al., *Am. J. Cardiol.* 83:1345-1349, 1999). Soluble P-selectin concentration is elevated in the plasma of individuals with idiopathic thrombocytopenic purpura, rheumatoid arthritis, hypercholesterolemia, acute stroke, atherosclerosis, hypertension, acute lung injury, connective tissue disease, thrombotic thrombocytopenic purpura, hemolytic uremic syndrome, disseminated intravascular coagulation, and chronic renal failure (Katayama, M. et al., *Br. J. Haematol.* 84:702-710, 1993; Haznedaroglu, I. C. et al., *Acta Haematol.* 101:16-20, 1999; Ertenli, I. et al., *J. Rheumatol.* 25:1054-1058, 1998; Davi, G. et al., *Circulation* 97:953-957, 1998; Frijns, C. J. et al., *Stroke* 28:2214-2218, 1997; Blann, A. D. et al., *Thromb. Haemost.* 77:1077-1080, 1997; Blann, A. D. et al., *J. Hum. Hypertens.* 11:607-609, 1997; Sakamaki, F. et al., *A. J. Respir. Crit. Care Med.* 151:1821-1826, 1995; Takeda, I. et al., *Int. Arch. Allergy Immunol.* 105:128-134, 1994; Chong, B. H. et al., *Blood* 83:1535-1541, 1994; Bonomini, M. et al., *Nephron* 79:399-407, 1998). Additionally, any condition that involves platelet activation can potentially be a source of plasma elevations in P-selectin. P-selectin is rapidly presented on the cell surface following platelet of endothelial cell activation. Soluble P-selectin that has been translated from an alternative mRNA lacking a transmembrane domain is also released into the extracellular space following this activation. Soluble P-selectin can also be formed by proteolysis involving membrane-bound P-selectin, either directly or indirectly. Plasma soluble P-selectin is elevated on admission in patients with AMI treated with tPA or coronary angioplasty, with a peak elevation occurring 4 hours after onset (Shimomura, H. et al., *Am. J. Cardiol.* 81:397-400, 1998). Plasma soluble P-selectin was elevated less than one hour following an anginal attack in patients with unstable angina, and the concentration decreased with time, approaching baseline more than 5 hours after attack onset (Ikeda, H. et al., *Circulation* 92:1693-1696, 1995). The plasma concentration of soluble P-selectin can approach 1 µg/ml in ACS (Ikeda, H. et al., *Coron. Artery Dis.* 5:515-518, 1994). Further investigation into the release of soluble P-selectin into and its removal from the bloodstream need to be conducted. P-selectin may be a sensitive and specific marker of platelet and endothelial cell activation, conditions that support thrombus formation and inflammation. It is not, however, a specific marker of ACS. When used with another marker that is specific for cardiac tissue injury, P-selectin may be useful in the discrimination of unstable angina and AMI from stable angina. Furthermore, soluble P-selectin may be elevated to a greater degree in AMI than in unstable angina. P-selectin normally exists in two forms, membrane-bound and soluble. Published investigations note that a soluble form of P-selectin is produced by platelets and endothelial cells, and by shedding of membrane-bound P-selectin, potentially through a proteolytic mechanism. Soluble P-selectin may prove to be the most useful currently identified marker of platelet activation, since its plasma concentration may not be as influenced by the blood sampling procedure as other markers of platelet activation, such as PF4 and β-TG.

Thrombin is a 37 kDa serine proteinase that proteolytically cleaves fibrinogen to form fibrin, which is ultimately integrated into a crosslinked network during clot formation. Antithrombin III (ATIII) is a 65 kDa serine proteinase inhibitor that is a physiological regulator of thrombin, factor XIa, factor XIIa, and factor IXa proteolytic activity. The inhibitory activity of ATIII is dependent upon the binding of heparin. Heparin enhances the inhibitory activity of ATIII by 2-3 orders of magnitude, resulting in almost instantaneous inactivation of proteinases inhibited by ATIII. ATIII inhibits its target proteinases through the formation of a covalent 1:1 stoichiometric complex. The normal plasma concentration of the approximately 100 kDa thrombin-ATIII complex (TAT) is <5 ng/ml (50 pM). TAT concentration is elevated in patients with AMI and unstable angina, especially during spontaneous ischemic episodes (Biasucci, L. M. et al., *Am. J. Cardiol.* 77:85-87, 1996; Kienast, J. et al., *Thromb. Haemost.* 70:550-553, 1993). Furthermore, TAT may be elevated in the plasma of individuals with stable angina (Manten, A. et al., *Cardiovasc. Res.* 40:389-395, 1998). Other published reports have found no significant differences in the concentration of TAT in the plasma of patients with ACS (Manten, A. et al., *Cardiovasc. Res.* 40:389-395, 1998; Hoffmeister, H. M. et al., *Atherosclerosis* 144:151-157, 1999). Further investigation is needed to determine plasma TAT concentration changes associated with ACS. Elevation of the plasma TAT concentration is associated with any condition associated with coagulation activation, including stroke, surgery, trauma, disseminated intravascular coagulation, and thrombotic thrombocytopenic purpura. TAT is formed immediately following thrombin activation in the presence of heparin, which is the limiting factor in this interaction. TAT has a half-life of approximately 5 minutes in the bloodstream (Biasucci, L. M. et al., *Am. J. Cardiol.* 77:85-87, 1996). TAT concentration is elevated in, exhibits a sharp drop after 15 minutes, and returns to baseline less than 1 hour following coagulation activation. The plasma concentration of TAT can approach 50 ng/ml in ACS (Biasucci, L. M. et al., *Circulation* 93:2121-2127, 1996). TAT is a specific marker of coagulation activation, specifically, thrombin activation. TAT may be useful as a marker of coagulation activation on a diagnostic panel with other markers that are specific for plaque rupture and/or cardiac tissue injury.

D-dimer is a crosslinked fibrin degradation product with an approximate molecular mass of 200 kDa. The normal plasma concentration of D-dimer is <150 ng/ml (750 pM). The plasma concentration of D-dimer is elevated in patients with AMI and unstable angina, but not stable angina (Hoffmeister, H. M. et al., *Circulation* 91:2520-2527, 1995; Bayes-Genis, A. et al., *Thromb. Haemost.* 81:865-868, 1999; Gurfinkel, E. et al., *Br. Heart J.* 71:151-155, 1994; Kruskal, J. B. et al., *N. Engl. J. Med.* 317:1361-1365, 1987; Tanaka, M. and Suzuki, A., *Thromb. Res.* 76:289-298, 1994). The plasma concentration of D-dimer also will be elevated during any condition associated with coagulation and fibrinolysis activation, including stroke, surgery, atherosclerosis, trauma, and thrombotic thrombocytopenic purpura. D-dimer is released into the bloodstream immediately following proteolytic clot dissolution by plasmin. Plasma D-dimer concentrations are elevated soon after ACS onset (within 6 hours), and will remain elevated in proportion to the degree of hypercoagulability of the individual. In this regard, further investigation is needed to determine the kinetics of D-dimer removal form the bloodstream following ACS. The plasma concentration of D-dimer can exceed 2 µg/ml in patients with unstable angina (Gurfinkel, E. et al., *Br. Heart J.* 71:151-155, 1994). Plasma D-dimer is a specific marker of fibrinolysis and indicates the presence of a prothrombotic state associated with AMI and unstable angina. D-dimer is not specific for ACS, and plasma elevations of D-dimer may be associated with various risk factors for ACS. However, when used as a member of a panel that contains markers specific for cardiac injury, D-dimer may allow that discrimination of unstable angina and AMI from stable angina. This differentiation may allow physicians to more effectively treat patients presenting with acute chest pain.

von Willebrand factor (vWF) is a plasma protein produced by platelets, megakaryocytes, and endothelial cells composed of 220 kDa monomers that associate to form a series of high molecular weight multimers. These multimers normally range in molecular weight from 600-20,000 kDa. vWF participates in the coagulation process by stabilizing circulating coagulation factor VIII and by mediating platelet adhesion to exposed subendothelium, as well as to other platelets. The A1 domain of vWF binds to the platelet glycoprotein Ib-IX-V complex and non-fibrillar collagen type VI, and the A3 domain binds fibrillar collagen types I and III (Emsley, J. et al., *J. Biol. Chem.* 273:10396-10401, 1998). Other domains present in the vWF molecule include the integrin binding domain, which mediates platelet-platelet interactions, the the protease cleavage domain, which appears to be relevant to the pathogenesis of type 11A von Willebrand disease. The interaction of vWF with platelets is tightly regulated to avoid interactions between vWF and platelets in normal physiologic conditions. vWF normally exists in a globular state, and it undergoes a conformation transition to an extended chain structure under conditions of high sheer stress, commonly found at sites of vascular injury. This conformational change exposes intramolecular domains of the molecule and allows vWF to interact with platelets. Furthermore, shear stress may cause vWF release from endothelial cells, making a larger number of vWF molecules available for interactions with platelets. The conformational change in vWF can be induced in vitro by the addition of non-physiological modulators like ristocetin and botrocetin (Miyata, S. et al., *J. Biol. Chem.* 271:9046-9053, 1996). At sites of vascular injury, vWF rapidly associates with collagen in the subendothelial matrix, and virtually irreversibly binds platelets, effectively forming a bridge between platelets and the vascular subendothelium at the site of injury. Evidence also suggests that a conformational change in vWF may not be required for its interaction with the subendothelial matrix (Sixma, J. J. and de Groot, P. G., *Mayo Clin. Proc.* 66:628-633, 1991). This suggests that vWF may bind to the exposed subendothelial matrix at sites of vascular injury, undergo a conformational change because of the high localized shear stress, and rapidly bind circulating platelets, which will be integrated into the newly formed thrombus. Measurement of the total amount of vWF would allow one who is skilled in the art to identify changes in total vWF concentration associated with stroke or cardiovascular disease. This measurement could be performed through the measurement of various forms of the vWF molecule. Measurement of the A1 domain would allow the measurement of active vWF in the circulation, indicating that a pro-coagulant state exists because the A1 domain is accessible for platelet binding. In this regard, an assay that specifically measures vWF molecules with both the exposed A1 domain and either the integrin binding domain or the A3 domain would also allow for the identification of active vWF that would be available for mediating platelet-platelet interactions or mediate crosslinking of platelets to vascular subendothelium, respectively. Measurement of any of these vWF forms, when used in an assay that employs antibodies specific for the protease cleavage domain may allow assays to be used to determine the circulating concentration of various vWF forms in any individual, regardless of the presence of von Willebrand disease. The normal plasma concentration of vWF is 5-10 µg/ml, or 60-110% activity, as measured by platelet aggregation. The measurement of specific forms of vWF may be of importance in any type of vascular disease, including stroke and cardiovascular disease. The plasma vWF concentration is reportedly elevated in individuals with AMI and unstable angina, but not stable angina (Goto, S. et al., *Circulation* 99:608-613, 1999; Tousoulis, D. et al., *Int. J. Cardiol.* 56:259-262, 1996; Yazdani, S. et al., *J Am Coll Cardiol* 30:1284-1287, 1997; Montalescot, G. et al., *Circulation* 98:294-299). Furthermore, elevations of the plasma vWF concentration may be a predictor of adverse clinical outcome in patients with unstable angina (Montalescot, G. et al., *Circulation* 98:294-299). vWF concentrations also have been demonstrated to be elevated in patients with stroke and subarachnoid hemorrhage, and also appear to be useful in assessing risk of mortality following stroke (Blann, A. et al., *Blood Coagul. Fibrinolysis* 10:277-284, 1999; Hirashima, Y. et al. *Neurochem Res.* 22:1249-1255, 1997; Catto, A. J. et al., *Thromb. Hemost.* 77:1104-1108, 1997). The plasma concentration of vWF may be elevated in conjunction with any event that is associated with endothelial cell damage or platelet activation. vWF is present at high concentration in the bloodstream, and it is released from platelets and endothelial cells upon activation. vWF would likely have the greatest utility as a marker of platelet activation or, specifically, conditions that favor platelet activation and adhesion to sites of vascular injury. The conformation of VWF is also known to be altered by high shear stress, as would be associated with a partially stenosed blood vessel. As the blood flows past a stenosed vessel, it is subjected to shear stress considerably higher than what it encounters in the circulation of an undiseased individual. Another aspect of this invention measures the forms of vWF that arise from shear stress and the correlation of the forms to the presence of ACS.

Tissue factor (TF) is a 45 kDa cell surface protein expressed in brain, kidney, and heart, and in a transcriptionally regulated manner on perivascular cells and monocytes. TF forms a complex with factor VIIa in the presence of $Ca^{2+}$ ions, and it is physiologically active when it is membrane bound. This complex proteolytically cleaves factor X to form factor Xa. It is normally sequestered from the bloodstream. Tissue factor can be detected in the bloodstream in a soluble form, bound to factor VIIa, or in a complex with factor VIIa, and tissue factor pathway inhibitor that can also include factor Xa. TF also is expressed on the surface of macrophages, which are commonly found in atherosclerotic plaques. The normal serum concentration of TF is <0.2 ng/ml (4.5 pM). The plasma TF concentration is elevated in patients with ischemic heart disease (Falciani, M. et al., *Thromb. Haemost.* 79:495-499, 1998). TF is elevated in patients with unstable angina and AMI, but not in patients with stable angina (Falciani, M. et al., *Thromb. Haemost.* 79:495-499, 1998; Suefuji, H. et al., *Am. Heart J.* 134:253-259, 1997; Misumi, K. et al., *Am. J. Cardiol.* 81:22-26, 1998). Furthermore, TF expression on macrophages and TF activity in atherosclerotic plaques is more common in unstable angina than stable angina (Soejima, H. et al., *Circulation* 99:2908-2913, 1999; Kaikita, K. et al., *Arterioscler. Thromb. Vasc. Biol.* 17:2232-2237, 1997; Ardissino, D. et al., *Lancet* 349:769-771, 1997). The differences in plasma TF concentration in stable versus unstable angina may not be of statistical significance. Elevations in the serum concentration of TF are associated with any condition that causes or is a result of coagulation activation through the extrinsic pathway. These conditions can include subarachnoid hemorrhage, disseminated intravascular coagulation, renal failure, vasculitis, and sickle cell disease (Hirashima, Y. et al., *Stroke* 28:1666-1670, 1997; Takahashi, H. et al., *Am. J. Hematol.* 46:333-337, 1994; Koyama, T. et al., *Br. J. Haematol.* 87:343-347, 1994). TF is released immediately when vascular injury is coupled with extravascular cell injury. TF levels in ischemic heart disease patients can exceed 800 pg/ml within 2 days of onset (Falciani, M. et al., *Thromb. Haemost.* 79:495-499, 1998. TF levels were decreased in the chronic phase of AMI, as compared with the chronic phase (Suefuji, H. et al., *Am. Heart J.* 134:253-259, 1997). TF is a specific marker for activation of the extrinsic coagulation pathway and the presence of a general hypercoagulable state. It may be a sensitive marker of vascular injury resulting from plaque rupture and could have some benefit as a member of a panel. It is not specific for ACS, can be elevated in many disease states, and may even be artificially elevated by the blood sampling procedure. However, it may be possible to use TF as a marker to rule out patients for thrombolytic therapy. The infusion of tissue-type plasminogen activator (tPA) during thrombolytic therapy results in an activation of fibrinolysis, and the patient is unable to maintain blood clots. The administration of tPA to an individual with vascular injury could ultimately result in hemorrhage.

The coagulation cascade can be activated through either the extrinsic or intrinsic pathways. These enzymatic pathways share one final common pathway. The first step of the common pathway involves the proteolytic cleavage of prothrombin by the factor Xa/factor Va prothrombinase complex to yield active thrombin. Thrombin is a serine proteinase that proteolytically cleaves fibrinogen. Thrombin first removes fibrinopeptide A from fibrinogen, yielding desAA fibrin monomer, which can form complexes with all other fibrinogen-derived proteins, including fibrin degradation products, fibrinogen degradation products, desAA fibrin, and fibrinogen. The desAA fibrin monomer is generically referred to as soluble fibrin, as it is the first product of fibrinogen cleavage, but it is not yet crosslinked via factor XIIIa into an insoluble fibrin clot. DesAA fibrin monomer also can undergo further proteolytic cleavage by thrombin to remove fibrinopeptide B, yielding desAABB fibrin monomer. This monomer can polymerize with other desAABB fibrin monomers to form soluble desAABB fibrin polymer, also referred to as soluble fibrin or thrombus precursor protein (TpP™). TpP™ is the immediate precursor to insoluble fibrin, which forms a "mesh-like" structure to provide structural rigidity to the newly formed thrombus. In this regard, measurement of TpP™ in plasma is a direct measurement of active clot formation. The normal plasma concentration of TpP™ is <6 ng/ml (Laurino, J. P. et al., *Ann. Clin. Lab. Sci.* 27:338-345, 1997). American Biogenetic Sciences has developed an assay for TpP™ (U.S. Pat. Nos. 5,453,359 and 5,843,690) and states that its TpP™ assay can assist in the early diagnosis of AMI, the ruling out of AMI in chest pain patients, and the identification of patients with unstable angina that will progress to AMI. Other studies have confirmed that TpP™ is elevated in patients with AMI, most often within 6 hours of onset (Laurino, J. P. et al., *Ann. Clin. Lab. Sci.* 27:338-345, 1997; Carville, D. G. et al., *Clin. Chem.* 42:1537-1541, 1996). The plasma concentration of TpP™ is also elevated in patients with unstable angina, but these elevations may be indicative of the severity of angina and the eventual progression to AMI (Laurino, J. P. et al., *Ann. Clin. Lab. Sci.* 27:338-345, 1997). The concentration of TpP™ in plasma will theoretically be elevated during any condition that causes or is a result of coagulation activation, including disseminated intravascular coagulation, deep venous thrombosis, congestive heart failure, surgery, cancer, gastroenteritis, and cocaine overdose (Laurino, J. P. et al., *Ann. Clin. Lab. Sci.* 27:338-345, 1997). TpP™ is released into the bloodstream immediately following thrombin activation. TpP™ likely has a short half-life in the bloodstream because it will be rapidly converted to insoluble fibrin at the site of clot formation. Plasma TpP™ concentrations peak within 3 hours of AMI onset, returning to normal after 12 hours from onset. The plasma concentration of TpP™ can exceed 30 ng/ml in CVD (Laurino, J. P. et al., *Ann. Clin. Lab. Sci.* 27:338-345, 1997). TpP™ is a sensitive and specific marker of coagulation activation. It has been demonstrated that TpP™ is useful in the diagnosis of AMI, but only when it is used in conjunction with a specific marker of cardiac tissue injury. TpP™ is not a specific marker of ACS, and its concentration will be elevated in numerous disease states that involve coagulation activation, including conditions that are considered risk factors for the development of ACS. TpP™ may also be useful in determining the severity of unstable angina. American Biogenetic Sciences, Inc. instructs users of the TpP™ ELISA assay kit to collect blood using citrate as an anticoagulant, and they recommend against using EDTA. The effect of the anticoagulant used during blood sampling on plasma TpP™ levels is currently unclear. If the blood sampling procedure can be controlled, TpP™ may be the best available marker for coagulation activation.

(iii) Non-specific Markers for Myocardial Injury Related to Atherosclerotic Plaque Rupture The appearance of markers related to atherosclerotic plaque rupture may preceed specific markers of myocardial injury when ACS is due to atherosclerotic plaque rupture. Potential markers of atherosclerotic plaque rupture include human neutrophil elastase, inducible nitric oxide synthase, lysophosphatidic acid, malondialdehyde-modified low density lipoprotein, and various members of the matrix metalloproteinase (MMP) family, including MMP-1, -2, -3, and -9.

Human neutrophil elastase (HNE) is a 30 kDa serine proteinase that is normally contained within the azurophilic granules of neutrophils. HNE is released upon neutrophil activation, and its activity is regulated by circulating $\alpha_1$-proteinase inhibitor. Activated neutrophils are commonly found in atherosclerotic plaques, and rupture of these plaques may result in the release of HNE. The plasma HNE concentration is usually measured by detecting HNE-$\alpha_1$-PI complexes. The normal concentration of these complexes is 50 ng/ml, which indicates a normal concentration of approximately 25 ng/ml (0.8 nM) for HNE. HNE release also can be measured through the specific detection of fibrinopeptide B$\beta_{30-43}$, a specific HNE-derived fibrinopeptide, in plasma. Plasma HNE is elevated in patients with coronary stenosis, and its elevation is greater in patients with complex plaques than those with simple plaques (Kosar, F. et al., *Angiology* 49:193-201, 1998; Amaro, A. et al., *Eur. Heart J.* 16:615-622, 1995). Plasma HNE is not significantly elevated in patients with stable angina, but is elevated inpatients with unstable angina and AMI, as determined by measuring fibrinopeptide B$\beta_{30-43}$, with concentrations in unstable angina being 2.5-fold higher than those associated with AMI (Dinerman, J. L. et al., *J. Am. Coll. Cardiol.* 15:1559-1563, 1990; Mehta, J. et al., *Circulation* 79:549-556, 1989). Serum HNE is elevated in cardiac surgery, exercise-induced muscle damage, giant cell arteritis, acute respiratory distress syndrome, appendicitis, pancreatitis, sepsis, smoking-associated emphysema, and cystic fibrosis (Genereau, T. et al., *J. Rheumatol.* 25:710-713, 1998; Mooser, V. et al., *Arterioscler. Thromb. Vasc. Biol.* 19:1060-1065, 1999; Gleeson, M. et al. *Eur. J. Appl. Physiol.* 77:543-546, 1998; Gando, S. et al., *J Trauma* 42:1068-1072, 1997; Eriksson, S. et al., *Eur. J. Surg.* 161:901-905, 1995; Liras, G. et al., *Rev. Esp. Enferm. Dig.* 87:641-652, 1995; Endo, S. et al., *J. Inflamm.* 45:136-142, 1995; Janoff, A., *Annu Rev Med* 36:207-216, 1985). HNE may also be released during blood coagulation (Plow, E. F. and Plescia, J., *Thromb. Haemost.* 59:360-363, 1988; Plow, E. F., *J. Clin. Invest.* 69:564-572, 1982). Serum elevations of HNE could also be associated with any non-specific infection or inflammatory state that involves neutrophil recruitment and activation. It is most likely released upon plaque rupture, since activated neutrophils are present in atherosclerotic plaques. HNE is presumably cleared by the liver after it has formed a complex with $\alpha_1$-PI.

Inducible nitric oxide synthase (iNOS) is a 130 kDa cytosolic protein in epithelial cells macrophages whose expression is regulated by cytokines, including interferon-$\gamma$, interleukin-1$\beta$, interleukin-6, and tumor necrosis factor $\alpha$, and lipopolysaccharide. iNOS catalyzes the synthesis of nitric oxide (NO) from L-arginine, and its induction results in a sustained high-output production of NO, which has antimicrobial activity and is a mediator of a variety of physiological and inflammatory events. NO production by iNOS is approximately 100 fold more than the amount produced by constitutively-expressed NOS (Depre, C. et al., *Cardiovasc. Res.* 41:465-472, 1999). There are no published investigations of plasma iNOS concentration changes associated with ACS. iNOS is expressed in coronary atherosclerotic plaque, and it may interfere with plaque stability through the production of peroxynitrite, which is a product of NO and superoxide and enhances platelet adhesion and aggregation (Depre, C. et al., *Cardiovasc. Res.* 41:465-472, 1999). iNOS expression during cardiac ischemia may not be elevated, suggesting that iNOS may be useful in the differentiation of angina from AMI (Hammerman, S. I. et al., *Am. J. Physiol.* 277:H1579-H1592, 1999; Kaye, D. M. et al., *Life Sci* 62:883-887, 1998). Elevations in the plasma iNOS concentration may be associated with cirrhosis, iron-deficiency anemia, or any other condition that results in macrophage activation, including bacterial infection (Jimenez, W. et al., *Hepatology* 30:670-676, 1999; Ni, Z. et al., *Kidney Int.* 52:195-201, 1997). iNOS may be released into the bloodstream as a result of atherosclerotic plaque rupture, and the presence of increased amounts of iNOS in the bloodstream may not only indicate that plaque rupture has occurred, but also that an ideal environment has been created to promote platelet adhesion. However, iNOS is not specific for atherosclerotic plaque rupture, and its expression can be induced during non-specific inflammatory conditions.

Lysophosphatidic acid (LPA) is a lysophospholipid intermediate formed in the synthesis of phosphoglycerides and triacylglycerols. It is formed by the acylation of glycerol-3 phosphate by acyl-coenzyme A and during mild oxidation of low-density lipoprotein (LDL). LPA is a lipid second messanger with vasoactive properties, and it can function as a platelet activator. LPA is a component of atherosclerotic lesions, particularly in the core, which is most prone to rupture (Siess, W., *Proc. Natl. Acad. Sci. U.S.A.* 96, 6931-6936, 1999). The normal plasma LPA concentration is 540 nM. Serum LPA is elevated in renal failure and in ovarian cancer and other gynecologic cancers (Sasagawa, T. et al., *J. Nutr. Sci. Vitaminol. (Tokyo)* 44:809-818, 1998; Xu, Y. et al., *JAMA* 280:719-723, 1998). In the context of unstable angina, LPA is most likely released as a direct result of plaque rupture. The plasma LPA concentration can exceed 60 µM in patients with gynecologic cancers (Xu, Y. et al., *JAMA* 280:719-723, 1998). Serum LPA may be a useful marker of atherosclerotic plaque rupture, which may allow the discrimination of unstable angina from stable angina. However, LPA may not be as specific as other markers of plaque rupture.

Malondialdehyde-modified low-density lipoprotein (MDA-modified LDL) is formed during the oxidation of the apoB-100 moiety of LDL as a result of phospholipase activity, prostaglandin synthesis, or platelet activation. MDA-modified LDL can be distinguished from oxidized LDL because MDA modifications of LDL occur in the absence of lipid peroxidation (Holvoet, P., *Acta Cardiol.* 53:253-260, 1998). The normal plasma concentration of MDA-modified LDL is less than 4 µg/ml (~10 µM). Plasma concentrations of oxidized LDL are elevated in stable angina, unstable angina, and AMI, indicating that it may be a marker of atherosclerosis (Holvoet, P., *Acta Cardiol.* 53:253-260, 1998; Holvoet, P. et al., *Circulation* 98:1487-1494, 1998). Plasma MDA-modified LDL is not elevated in stable angina, but is significantly elevated in unstable angina and AMI (Holvoet, P., *Acta Cardiol.* 53:253-260, 1998; Holvoet, P. et al., *Circulation* 98:1487-1494, 1998; Holvoet, P. et al., *JAMA* 281:1718-1721, 1999). Plasma MDA-modified LDL is elevated in individuals with beta-thallasemia and in renal transplant patients (Livrea, M. A. et al., *Blood* 92:3936-3942, 1998; Ghanem, H. et al., *Kidney Int.* 49:488-493, 1996; van den Dorpel, M. A. et al., *Transpl. Int.* 9 Suppl. 1:S54-S57, 1996). Furthermore, serum MDA-modified LDL may be elevated during hypoxia (Balagopalakrishna, C. et al., *Adv. Exp. Med. Biol.* 411:337-345, 1997). The plasma concentration of MDA-modified LDL is elevated within 6-8 hours from the onset of chest pain. Plasma concentrations of MDA-modified LDL can approach 20 µg/ml (~50 µM) in patients with AMI, and 15 µg/ml (~40 µM) in patients with unstable angina (Holvoet, P. et al., *Circulation* 98:1487-1494, 1998). Plasma MDA-modified LDL has a half-life of less than 5 minutes in mice (Ling, W. et al., *J. Clin. Invest.* 100:244-252, 1997). MDA-modified LDL appears to be a specific marker of atherosclerotic plaque rupture in acute coronary symptoms. It is unclear, however, if elevations in the plasma concentration of MDA-modified LDL are a result of plaque rupture or platelet activation. The most reasonable explanation is that the presence of increased amounts of MDA-modified LDL is an indication of both events. MDA-modified LDL may be useful in discriminating unstable angina and AMI from stable angina, but it alone can not distinguish AMI from unstable angina. In this regard, MDA-modified LDL would be most useful as part of a panel of markers, particularly with another marker that can distinguish AMI from unstable angina.

Matrix metalloproteinase-1 (MMP-1), also called collagenase-1, is a 41/44 kDa zinc- and calcium-binding proteinase that cleaves primarily type I collagen, but can also cleave collagen types II, III, VII and X. The active 41/44 kDa enzyme can undergo autolysis to the still active 22/27 kDa form. MMP-1 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-1, like other MMPs, is involved in extracellular matrix remodeling, which can occur following injury or during intervascular cell migration. MMP-1 can be found in the bloodstream either in a free form or in complex with TIMP-1, its natural inhibitor. MMP-1 is normally found at a concentration of <25 ng/ml in plasma. There have been no conclusive published investigations into changes in the serum or plasma concentration of MMP-1 associated with ACS. However, MMP-1 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Furthermore, MMP-1 has been implicated in the pathogenesis of myocardial reperfusion injury (Shibata, M. et al., *Angiology* 50:573-582, 1999). Serum MMP-1 may be elevated inflammatory conditions that induce mast cell degranulation. Serum MMP-1 concentrations are elevated in patients with arthritis and systemic lupus erythematosus (Keyszer, G. et al., *Z Rheumatol* 57:392-398, 1998; Keyszer, G. *J. Rheumatol.* 26:251-258, 1999). Serum MMP-1 also is elevated in patients with prostate cancer, and the degree of elevation corresponds to the metastatic potential of the tumor (Baker, T. et al., *Br. J. Cancer* 70:506-512, 1994). The serum concentration of MMP-1 may also be elevated in patients with other types of cancer. Serum MMP-1 is decreased in patients with hemochromatosis and also in patients with chronic viral hepatitis, where the concentration is inversely related to the severity (George, D. K. et al., *Gut* 42:715-720, 1998; Murawaki, Y. et al., *J. Gastroenterol. Hepatol.* 14:138-145, 1999). MMP-1 is released during mast cell degranulation, and is presumably released during atherosclerotic plaque rupture. MMP-1 concentrations are lower in heparinized plasma than in EDTA plasma or serum, and diluted samples give higher concentration values in an ELISA assay than undiluted samples, presumable due to reduction of the inihibitory effects of protein MMP inhibitors or matrix components (Lein, M. et al., *Clin. Biochem.* 30:491-496, 1997). Serum MMP-1 was decreased in the first four days following AMI, and increased thereafter, reaching peak levels 2 weeks after the onset of AMI (George, D. K. et al., *Gut* 42:715-720, 1998).

Matrix metalloproteinase-2 (MMP-2), also called gelatinase A, is a 66 kDa zinc- and calcium-binding proteinase that is synthesized as an inactive 72 kDa precursor. Mature MMP-3 cleaves type I gelatin and collagen of types IV, V, VII, and X. MMP-2 is synthesized by a variety of cells, including vascular smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-2 is usually found in plasma in complex with TIMP-2, its physiological regulator (Murawaki, Y. et al., *J. Hepatol.* 30:1090-1098, 1999). The normal plasma concentration of MMP-2 is <~550 ng/ml (8 nM). MMP-2 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-2 has been implicated as a contributor to plaque instability and rupture (Shah, P. K. et al., *Circulation* 92:1565-1569, 1995). Serum MMP-2 concentrations were elevated in patients with stable angina, unstable angina, and AMI, with elevations being significantly greater in unstable angina and AMI than in stable angina (Kai, H. et al., *J. Am. Coll. Cardiol.* 32:368-372, 1998). There was no change in the serum MMP-2 concentration in individuals with stable angina following a treadmill exercise test (Kai, H. et al., *J. Am. Coll. Cardiol.* 32:368-372, 1998). Serum and plasma MMP-2 is elevated in patients with gastric cancer, hepatocellular carcinoma, liver cirrhosis, urothelial carcinoma, rheumatoid arthritis, and lung cancer (Murawaki, Y. et al., *J. Hepatol.* 30:1090-1098, 1999; Endo, K. et al., *Anticancer Res.* 17:2253-2258, 1997; Gohji, K. et al., *Cancer* 78:2379-2387, 1996; Gruber, B. L. et al., *Clin. Immunol. Immunopathol.* 78:161-171, 1996; Garbisa, S. et al., *Cancer Res.* 52:4548-4549, 1992). Furthermore, MMP-2 may also be translocated from the platelet cytosol to the extracellular space during platelet aggregation (Sawicki, G. et al., *Thromb. Haemost.* 80:836-839, 1998). MMP-2 was elevated on admission in the serum of individuals with unstable angina and AMI, with maximum levels approaching 1.5 µg/ml (25 nM) (Kai, H. et al., *J. Am. Coll. Cardiol.* 32:368-372, 1998). The serum MMP-2 concentration peaked 1-3 days after onset in both unstable angina and AMI, and started to return to normal after 1 week (Kai, H. et al., *J. Am. Coll. Cardiol.* 32:368-372, 1998).

Matrix metalloproteinase-3 (MMP-3), also called stromelysin-1, is a 45 kDa zinc- and calcium-binding proteinase that is synthesized as an inactive 60 kDa precursor. Mature MMP-3 cleaves proteoglycan, fibrinectin, laminin, and type IV collagen, but not type I collagen. MMP-3 is synthesized by a variety of cells, including smooth muscle cells, mast cells, macrophage-derived foam cells, T lymphocytes, and endothelial cells (Johnson, J. L. et al., *Arterioscler. Thromb. Vasc. Biol.* 18:1707-1715, 1998). MMP-3, like other MMPs, is involved in extracellular matrix remodeling, which can occur following injury or during intervascular cell migration. MMP-3 is normally found at a concentration of <125 ng/ml in plasma. The serum MMP-3 concentration also has been shown to increase with age, and the concentration in males is approximately 2 times higher in males than in females (Manicourt, D. H. et al., *Arthritis Rheum.* 37:1774-1783, 1994). There have been no conclusive published investigations into changes in the serum or plasma concentration of MMP-3 associated with ACS. However, MMP-3 is found in the shoulder region of atherosclerotic plaques, which is the region most prone to rupture, and may be involved in atherosclerotic plaque destabilization (Johnson, J. L. et al., *Arterioscler. Thromb. Vasc. Biol.* 18:1707-1715, 1998). Therefore, MMP-3 concentration may be elevated as a result of atherosclerotic plaque rupture in unstable angina. Serum MMP-3 may be elevated inflammatory conditions that induce mast cell degranulation. Serum MMP-3 concentrations are elevated in patients with arthritis and systemic lupus erythematosus (Zucker, S. et al. *J. Rheumatol.* 26:78-80, 1999; Keyszer, G. et al., *Z Rheumatol.* 57:392-398, 1998; Keyszer, G. et al. *J. Rheumatol.* 26:251-258, 1999). Serum MMP-3 also is elevated in patients with prostate and urothelial cancer, and also glomerulonephritis (Lein, M. et al., *Urologe A* 37:377-381, 1998; Gohji, K. et al., *Cancer* 78:2379-2387, 1996; Akiyama, K. et al., *Res. Commun. Mol. Pathol. Pharmacol.* 95:115-128, 1997). The serum concentration of MMP-3 may also be elevated in patients with other types of cancer. Serum MMP-3 is decreased in patients with hemochromatosis (George, D. K. et al., *Gut* 42:715-720, 1998).

Matrix metalloproteinase-9 (MMP-9) also called gelatinase B, is an 84 kDa zinc- and calcium-binding proteinase that is synthesized as an inactive 92 kDa precursor. Mature MMP-9 cleaves gelatin types I and V, and collagen types IV and V. MMP-9 exists as a monomer, a homodimer, and a heterodimer with a 25 kDa $\alpha_2$-microglobulin-related protein (Triebel, S. et al., *FEBS Lett.* 314:386-388, 1992). MMP-9 is synthesized by a variety of cell types, most notably by neutrophils. The normal plasma concentration of MMP-9 is <35 ng/ml (400 pM). MMP-9 expression is elevated in vascular smooth muscle cells within atherosclerotic lesions, and it may be released into the bloodstream in cases of plaque instability (Kai, H. et al., *J. Am. Coll. Cardiol.* 32:368-372, 1998). Furthermore, MMP-9 may have a pathogenic role in the development of ACS (Brown, D. L. et al., *Circulation* 91:2125-2131, 1995). Plasma MMP-9 concentrations are significantly elevated in patients with unstable angina and AMI, but not stable angina (Kai, H. et al., *J. Am. Coll. Cardiol.* 32:368-372, 1998). The elevations in patients with AMI may also indicate that those individuals were suffering from unstable angina. Elevations in the plasma concentration of MMP-9 may also be greater in unstable angina than in AMI, but these differences may not be statistically significant. There was no significant change in plasma MMP-9 levels after a treadmill exercise test in patients with stable angina (Kai, H. et al., *J. Am. Coll. Cardiol.* 32:368-372, 1998). Plasma MMP-9 is elevated in individuals with rheumatoid arthritis, septic shock, giant cell arteritis and various carcinomas (Gruber, B. L. et al., *Clin. Immunol. Immunopathol.* 78:161-171, 1996; Nakamura, T. et al., *Am. J. Med. Sci.* 316:355-360, 1998; Blankaert, D. et al., *J. Acquir. Immune Defic. Syndr. Hum. Retrovirol.* 18:203-209, 1998; Endo, K. et al. *Anticancer Res.* 17:2253-2258, 1997; Hayasaka, A. et al., *Hepatology* 24:1058-1062, 1996; Moore, D. H. et al., *Gynecol. Oncol.* 65:78-82, 1997; Sorbi, D. et al., *Arthritis Rheum.* 39:1747-1753, 1996; Iizasa, T. et al., *Clin., Cancer Res.* 5:149-153, 1999). Furthermore, the plasma MMP-9 concentration may be elevated in stroke and cerebral hemorrhage (Mun-Bryce, S. and Rosenberg, G. A., *J. Cereb. Blood Flow Metab.* 18:1163-1172, 1998; Romanic, A. M. et al., *Stroke* 29:1020-1030, 1998; Rosenberg, G. A., *J. Neurotrauma* 12:833-842, 1995). MMP-9 was elevated on admission in the serum of individuals with unstable angina and AMI, with maximum levels approaching 150 ng/ml (1.7 nM) (Kai, H. et al., *J. Am. Coll. Cardiol.* 32:368-372, 1998). The serum MMP-9 concentration was highest on admission in patients unstable angina, and the concentration decreased gradually after treatment, approaching baseline more than 1 week after onset (Kai, H. et al., *J. Am. Coll. Cardiol.* 32:368-372, 1998).

(iv) Other Non-specific Markers of Myocardial Injury

Activation of the inflammatory response may be manifested in the early stages of ACS. In this regard, measurement of the circulating concentrations of non-specific markers of inflammation and acute phase reactants may be of use in identifying individuals with ACS, as well as individuals at risk for developing ACS. Examples of such markers associated with inflammation and the acute phase response include C-reactive protein, interleukin-1β, interleukin-1 receptor antagonist, interleukin-6, monocyte chemotactic protein-1, soluble intercellular adhesion molecule-1, soluble vascular cell adhesion molecule-1, tumor necrosis factor α, caspase-3 and hemoglobin $\alpha_2$.

C-reactive protein is a (CRP) is a homopentameric $Ca^{2+}$-binding acute phase protein with 21 kDa subunits that is involved in host defense. CRP preferentially binds to phosphorylcholine, a common constituent of microbial membranes. Phosphorylcholine is also found in mammalian cell membranes, but it is not present in a form that is reactive with CRP. The interaction of CRP with phosphorylcholine promotes agglutination and opsonization of bacteria, as well as activation of the complement cascade, all of which are involved in bacterial clearance. Furthermore, CRP can interact with DNA and histones, and it has been suggested that CRP is a scavenger of nuclear material released from damaged cells into the circulation (Robey, F. A. et al., *J. Biol. Chem.* 259:7311-7316, 1984). CRP synthesis is induced by Il-6, and indirectly by IL-1, since IL-1 can trigger the synthesis of IL-6 by Kupffer cells in the hepatic sinusoids. The normal plasma concentration of CRP is <3 μg/ml (30 nM) in 90% of the healthy population, and <10 μg/ml (100 nM) in 99% of healthy individuals. Plasma CRP concentrations can be measured by rate nephelometry or ELISA. The plasma concentration of CRP is significantly elevated in patients with AMI and unstable angina, but not stable angina (Biasucci, L. M. et al., *Circulation* 94:874-877, 1996; Biasucci, L. M. et al., *Am. J. Cardiol.* 77:85-87, 1996; Benamer, H. et al., *Am. J. Cardiol.* 82:845-850, 1998; Caligiuri, G. et al., *J. Am. Coll. Cardiol.* 32:1295-1304, 1998; Curzen, N. P. et al., *Heart* 80:23-27, 1998; Dangas, G. et al., *Am. J. Cardiol.* 83:583-5, A7, 1999). CRP may also be elevated in the plasma of individuals with variant or resolving unstable angina, but mixed results have been reported (Benamer, H. et al., *Am. J. Cardiol.* 82:845-850, 1998; Caligiuri, G. et al., *J. Am. Coll. Cardiol.* 32:1295-1304, 1998). CRP may not be useful in predicting the outcome of patients with AMI or unstable angina (Curzen, N. P. et al., *Heart* 80:23-27, 1998; Rebuzzi, A. G. et al., *Am. J. Cardiol.* 82:715-719, 1998; Oltrona, L. et al., *Am. J. Cardiol.* 80:1002-1006, 1997). The concentration of CRP will be elevated in the plasma from individuals with any condition that may elicit an acute phase response, such as infection, surgery, trauma, and stroke. CRP is a secreted protein that is released into the bloodstream soon after synthesis. CRP synthesis is upregulated by IL-6, and the plasma CRP concentration is significantly elevated within 6 hours of stimulation (Biasucci, L. M. et al., *Am. J. Cardiol.* 77:85-87, 1996). The plasma CRP concentration peaks approximately 50 hours after stimulation, and begins to decrease with a half-life of approximately 19 hours in the bloodstream (Biasucci, L. M. et al., *Am. J. Cardiol.* 77:85-87, 1996). Other investigations have confirmed that the plasma CRP concentration in individuals with unstable angina (Biasucci, L. M. et al., *Circulation* 94:874-877, 1996). The plasma concentration of CRP can approach 100 μg/ml (1 μM) in individuals with ACS (Biasucci, L. M. et al., *Circulation* 94:874-877, 1996; Liuzzo, G. et al., *Circulation* 94:2373-

2380, 1996). CRP is a specific marker of the acute phase response. Elevations of CRP have been identified in the plasma of individuals with AMI and unstable angina, most likely as a result of activation of the acute phase response associated with atherosclerotic plaque rupture or cardiac tissue injury. CRP is a highly nonspecific marker for ACS, and elevations of the CRP concentration in plasma may occur from unrelated conditions involving activation of the immune system. Despite its high degree of non-specificity for ACS, CRP may be useful in the identification of unstable angina and AMI when used with another marker that is specific for cardiac tissue injury. Plasma has a high concentration of CRP and there is much variability in the reported concentration of CRP in the blood of healthy individuals. Further investigation using a uniform assay, most likely a competitive immunoassay, on a range of plasma samples is necessary to determine the upper limits of the concentration of CRP in the plasma of apparently healthy individuals.

Interleukin-1β (IL-1β) is a 17 kDa secreted proinflammatory cytokine that is involved in the acute phase response and is a pathogenic mediator of many diseases. IL-1β is normally produced by macrophages and epithelial cells. IL-1β is also released from cells undergoing apoptosis. The normal serum concentration of IL-1β is <30 pg/ml (1.8 pM). There have been no conclusive investigations into potential elevations of the plasma concentration of IL-1β in individuals with ACS, possibly due to sensitivity limitations of the assay or clearance of IL-1β from the bloodstream soon after ACS onset. In theory, IL-1β would be elevated earlier than other acute phase proteins such as CRP in unstable angina and AMI, since IL-1β is an early participant in the acute phase response. Furthermore, IL-1β is released from cells undergoing apoptosis, which may be activated in the early stages of ischemia. In this regard, elevation of the plasma IL-1β concentration associated with ACS requires further investigation using a high-sensitivity assay. Elevations of the plasma IL-1β concentration are associated with activation of the acute phase response in proinflammatory conditions such as trauma and infection. IL-1β has a biphasic physiological half-life of 5 minutes followed by 4 hours (Kudo, S. et al., *Cancer Res.* 50:5751-5755, 1990). IL-1β is released into the extracellular milieu upon activation of the inflammatory response or apoptosis. It is possible that IL-1β is elevated for only a short time after AMI and unstable angina episodes, and most blood samples taken on admission from patients with ACS are outside the window of IL-1β elevation following insult.

Interleukin-1 receptor antagonist (IL-1ra) is a 17 kDa member of the IL-1 family predominantly expressed in hepatocytes, epithelial cells, monocytes, macrophages, and neutrophils. IL-1ra has both intracellular and extracellular forms produced through alternative splicing. IL-1ra is thought to participate in the regulation of physiological IL-1 activity. IL-1ra has no IL-1-like physiological activity, but is able to bind the IL-1 receptor on T-cells and fibroblasts with an affinity similar to that of IL-1β, blocking the binding of IL-1α and IL-1β and inhibiting their bioactivity (Stockman, B. J. et al., *Biochemistry* 31:5237-5245, 1992; Eisenberg, S. P. et al., *Proc. Natl. Acad. Sci. U.S.A.* 88:5232-5236, 1991; Carter, D. B. et al., *Nature* 344:633-638, 1990). IL-1ra is normally present in higher concentrations than IL-1 in plasma, and it has been suggested that IL-1ra levels are a better correlate of disease severity than IL-1 (Biasucci, L. M. et al., *Circulation* 99:2079-2084, 1999). Furthermore, there is evidence that IL-1ra is an acute phase protein (Gabay, C. et al., *J. Clin. Invest.* 99:2930-2940, 1997). The normal plasma concentration of IL-1ra is <200 pg/ml (12 pM). The plasma concentration of IL-1ra is elevated in patients with AMI and unstable angina that proceeded to AMI, death, or refractory angina (Biasucci, L. M. et al., *Circulation* 99:2079-2084, 1999; Latini, R. et al., *J. Cardiovasc. Pharmacol.* 23:1-6, 1994). Furthermore, IL-1ra was significantly elevated in severe AMI as compared to uncomplicated AMI (Latini, R. et al., *J. Cardiovasc. Pharmacol.* 23:1-6, 1994). This indicates that IL-1ra may be a useful marker of ACS severity in unstable angina and AMI. Elevations in the plasma concentration of IL-1ra are associated with any condition that involves activation of the inflammatory or acute phase response, including infection, trauma, and arthritis. IL-1ra is released into the bloodstream in pro-inflammatory conditions, and it may also be released as a participant in the acute phase response. The major sources of clearance of IL-1ra from the bloodstream appear to be kidney and liver (Kim, D. C. et al., *J. Pharm. Sci.* 84:575-580, 1995). IL-1ra concentrations were elevated in the plasma of individuals with unstable angina within 24 hours of onset, and these elevations may even be evident within 2 hours of onset (Biasucci, L. M. et al., *Circulation* 99:2079-2084, 1999). In patients with severe progression of unstable angina, the plasma concentration of IL-1ra was higher 48 hours after onset than levels at admission, while the concentration decreased in patients with uneventful progression (Biasucci, L. M. et al., *Circulation* 99:2079-2084, 1999). In addition, the plasma concentration of IL-1ra associated with unstable angina can approach 1.4 ng/ml (80 pM). IL-1ra may be a useful marker of ACS severity. It is not a specific marker of ACS, but changes in the plasma concentration of IL-1ra appear to be related to disease severity. Furthermore, it is likely released in conjunction with or soon after IL-1 release in pro-inflammatory conditions, and it is found at higher concentrations than IL-1. This indicates that IL-1ra may be a useful indirect marker of IL-1 activity, which elicits the production of IL-6. Thus, IL-1ra may be useful not only in grading the severity of unstable angina and AMI, but also in the identification of the early stages of the acute phase response, before IL-6 concentrations are significantly elevated.

Interleukin-6 (IL-6) is a 20 kDa secreted protein that is a hematopoietin family proinflammatory cytokine. IL-6 is an acute-phase reactant and stimulates the synthesis of a variety of proteins, including adhesion molecules. Its major function is to mediate the acute phase production of hepatic proteins, and its synthesis is induced by the cytokine IL-1. IL-6 is normally produced by macrophages and T lymphocytes. The normal serum concentration of IL-6 is <3 pg/ml (0.15 pM). The plasma concentration of IL-6 is elevated in patients with AMI and unstable angina, to a greater degree in AMI (Biasucci, L. M. et al., *Circulation* 94:874-877, 1996; Manten, A. et al., *Cardiovasc. Res.* 40:389-395, 1998; Biasucci, L. M. et al., *Circulation* 99:2079-2084, 1999). IL-6 is not significantly elevated in the plasma of patients with stable angina (Biasucci, L. M. et al., *Circulation* 94:874-877, 1996; Manten, A. et al., *Cardiovasc. Res.* 40:389-395, 1998). Furthermore, IL-6 concentrations increase over 48 hours from onset in the plasma of patients with unstable angina with severe progression, but decrease in those with uneventful progression (Biasucci, L. M. et al., *Circulation* 99:2079-2084, 1999). This indicates that IL-6 may be a useful indicator of disease progression. Plasma elevations of IL-6 are associated with any nonspecific proinflammatory condition such as trauma, infection, or other diseases that elicit an acute phase response. IL-6 has a half-life of 4.2 hours in the bloodstream and is elevated following AMI and unstable angina (Manten, A. et al., Cardiovasc. Res. 40:389-395, 1998). The plasma concentration of IL-6 is elevated within 8-12 hours of AMI onset, and can approach 100 pg/ml. The plasma concentration of IL-6 in patients with unstable angina was elevated at peak levels 72 hours after onset, possibly due to the severity of insult (Biasucci, L. M. et al., *Circulation* 94:874-877, 1996). IL-6 appears to be a sensitive marker of inflammation associated with ACS. However, it is not specific for ACS, and may be elevated in various conditions that are considered risk factors for ACS. However, IL-6 may be useful in identifying the severity of AMI or unstable angina, allowing physicians to monitor these patients closely for disease progression. Furthermore, IL-6 may be useful in distinguishing unstable angina and AMI from stable angina.

Tumor necrosis factor α (TNFα) is a 17 kDa secreted proinflammatory cytokine that is involved in the acute phase response and is a pathogenic mediator of many diseases. TNFα is normally produced by macrophages and natural killer cells. The normal serum concentration of TNFα is <40 pg/ml (2 pM). The plasma concentration of TNFα is elevated in patients with AMI, and is marginally elevated in patients with unstable angina (Li, D. et al., *Am. Heart J.* 137:1145-1152, 1999; Squadrito, F. et al., *Inflamm. Res.* 45:14-19, 1996; Latini, R. et al., *J. Cardiovasc. Pharmacol.* 23:1-6, 1994; Carlstedt, F. et al., *J. Intern. Med.* 242:361-365, 1997). Elevations in the plasma concentration of TNFα are associated with any proinflammatory condition, including trauma, stroke, and infection. TNFα has a half-life of approximately 1 hour in the bloodstream, indicating that it may be removed from the circulation soon after symptom onset. In patients with AMI, TNFα was elevated 4 hours after the onset of chest pain, and gradually declined to normal levels within 48 hours of onset (Li, D. et al., *Am. Heart J.* 137:1145-1152, 1999). The concentration of TNFα in the plasma of AMI patients exceeded 300 pg/ml (15 pM) (Squadrito, F. et al., *Inflamm. Res.* 45:14-19, 1996).

Soluble intercellular adhesion molecule (sICAM-1), also called CD54, is a 85-110 kDa cell surface-bound immunoglobulin-like integrin ligand that facilitates binding of leukocytes to antigen-presenting cells and endothelial cells during leukocyte recruitment and migration. sICAM-1 is normally produced by vascular endothelium, hematopoietic stem cells and non-hematopoietic stem cells, which can be found in intestine and epidermis. sICAM-1 can be released from the cell surface during cell death or as a result of proteolytic activity. The normal plasma concentration of sICAM-1 is approximately 250 ng/ml (2.9 nM). The plasma concentration of sICAM-1 is significantly elevated in patients with AMI and unstable angina, but not stable angina (Pellegatta, F. et al., *J. Cardiovasc. Pharmacol.* 30:455-460, 1997; Miwa, K. et al., *Cardiovasc. Res.* 36:37-44, 1997; Ghaisas, N. K. et al., *Am. J. Cardiol.* 80:617-619, 1997; Ogawa, H. et al., *Am. J. Cardiol.* 83:38-42, 1999). Furthermore, ICAM-1 is expressed in atherosclerotic lesions and in areas predisposed to lesion formation, so it may be released into the bloodstream upon plaque rupture (Iiyama, K. et al., *Circ. Res.* 85:199-207, 1999; Tenaglia, A. N. et al., *Am. J. Cardiol.* 79:742-747, 1997). Elevations of the plasma concentration of sICAM-1 are associated with ischemic stroke, hjead trauma, atherosclerosis, cancer, preeclampsia, multiple sclerosis, cystic fibrosis, and other nonspecific inflammatory states (Kim, J. S., *J. Neurol. Sci.* 137:69-78, 1996; Laskowitz, D. T. et al., *J. Stroke Cerebrovasc. Dis.* 7:234-241, 1998). The plasma concentration of sICAM-1 is elevated during the acute stage of AMI and unstable angina. The elevation of plasma sICAM-1 reaches its peak within 9-12 hours of AMI onset, and returns to normal levels within 24 hours (Pellegatta, F. et al., *J. Cardiovasc. Pharmacol.* 30:455-460, 1997). The plasma concentration of sICAM can approach 700 ng/ml (8 nM) in patients with AMI (Pellegatta, F. et al., *J. Cardiovasc. Pharmacol.* 30:455-460, 1997). sICAM-1 is elevated in the plasma of individuals with AMI and unstable angina, but it is not specific for these diseases. It may, however, be useful marker in the differentiation of AMI and unstable angina from stable angina since plasma elevations are not associated with stable angina. Interestingly, ICAM-1 is present in atherosclerotic plaques, and may be released into the bloodstream upon plaque rupture. Thus, sICAM may be useful not only as a marker of inflammation, but also plaque rupture associated with ACS.

Vascular cell adhesion molecule (VCAM), also called CD106, is a 100-110 kDa cell surface-bound immunoglobulin-like integrin ligand that facilitates binding of B lymphocytes and developing T lymphocytes to antigen-presenting cells during lymphocyte recruitment. VCAM is normally produced by endothelial cells, which line blood and lymph vessels, the heart, and other body cavities. VCAM-1 can be released from the cell surface during cell death or as a result of proteolytic activity. The normal serum concentration of sVCAM is approximately 650 ng/ml (6.5 nM). The plasma concentration of sVCAM-1 is marginally elevated in patients with AMI, unstable angina, and stable angina (Mulvihill, N. et al., *Am. J. Cardiol.* 83:1265-7, A9, 1999; Ghaisas, N. K. et al., *Am. J. Cardiol.* 80:617-619, 1997). However, sVCAM-1 is expressed in atherosclerotic lesions and its plasma concentration may correlate with the extent of atherosclerosis (Iiyama, K. et al., *Circ. Res.* 85:199-207, 1999; Peter, K. et al., *Arterioscler. Thromb. Vasc. Biol.* 17:505-512, 1997). Elevations in the plasma concentration of sVCAM-1 are associated with ischemic stroke, cancer, diabetes, preeclampsia, vascular injury, and other nonspecific inflammatory states (Bitsch, A. et al., *Stroke* 29:2129-2135, 1998; Otsuki, M. et al., *Diabetes* 46:2096-2101, 1997; Banks, R. E. et al., *Br. J. Cancer* 68:122-124, 1993; Steiner, M. et al., *Thromb. Haemost.* 72:979-984, 1994; Austgulen, R. et al., *Eur. J. Obstet. Gynecol. Reprod. Biol.* 71:53-58, 1997).

Monocyte chemotactic protein-1 (MCP-1) is a 10 kDa chemotactic factor that attracts monocytes and basophils, but not neutrophils or eosiniphils. MCP-1 is normally found in equilibrium between a monomeric and homodimeric form, and it is normally produced in and secreted by monocytes and vascular endothelial cells (Yoshimura, T. et al., *FEBS Lett.* 244:487-493, 1989; Li, Y. S. et al., *Mol. Cell. Biochem.* 126:61-68, 1993). MCP-1 has been implicated in the pathogenesis of a variety of diseases that involve monocyte infiltration, including psoriasis, rheumatoid arthritis, and atherosclerosis. The normal concentration of MCP-1 in plasma is <0.1 ng/ml. The plasma concentration of MCP-1 is elevated in patients with AMI, and may be elevated in the plasma of patients with unstable angina, but no elevations are associated with stable angina (Soejima, H. et al., *J. Am. Coll. Cardiol.* 34:983-988, 1999; Nishiyama, K. et al., *Jpn. Circ. J.* 62:710-712, 1998; Matsumori, A. et al., *J. Mol. Cell. Cardiol.* 29:419-423, 1997). Interestingly, MCP-1 also may be involved in the recruitment of monocytes into the arterial wall during atherosclerosis. Elevations of the serum concentration of MCP-1 are associated with various conditions associated with inflammation, including alcoholic liver disease, interstitial lung disease, sepsis, and systemic lupus erythematosus (Fisher, N. C. et al., *Gut* 45:416-420, 1999; Suga, M. et al., *Eur. Respir. J.* 14:376-382, 1999; Bossink, A. W. et al., *Blood* 86:3841-3847, 1995; Kaneko, H. et al. *J. Rheumatol.* 26:568-573, 1999). MCP-1 is released into the bloodstream upon activation of monocytes and endothelial cells. The concentration of MCP-1 in plasma form patients with AMI has been reported to approach 1 ng/ml (100 pM), and can remain elevated for one month (Soejima, H. et al., *J. Am. Coll. Cardiol.* 34:983-988, 1999). The kinetics of MCP-1 release into and clearance from the bloodstream in the context of ACS are currently unknown. MCP-1 is a specific marker of the presence of a pro-inflammatory condition that involves monocyte migration. MCP-1 is not specific for ACS, but it concentration is reportedly elevated in the plasma of patients with AMI. Furthermore, MCP-1 concentrations may not be elevated in the plasma of patients with unstable angina or stable angina, which suggests that MCP-1 may be useful in discriminating AMI from unstable and stable angina.

Caspase-3, also called CPP-32, YAMA, and apopain, is an interleukin-1β converting enzyme (ICE)-like intracellular cysteine proteinase that is activated during cellular apoptosis. Caspase-3 is present as an inactive 32 kDa precursor that is proteolytically activated during apoptosis induction into a heterodimer of 20 kDa and 11 kDa subunits (Fernandes-Alnemri, T. et al., *J. Biol. Chem.* 269:30761-30764, 1994). Its cellular substrates include poly(ADP-ribose) polymerase (PARP) and sterol regulatory element binding proteins (SREBPs) (Liu, X. et al., *J. Biol. Chem.* 271:13371-13376, 1996). The normal plasma concentration of caspase-3 is unknown. There are no published investigations into changes in the plasma concentration of caspase-3 associated with ACS. There are increasing amounts of evidence supporting the hypothesis of apoptosis induction in cardiac myocytes associated with ischemia and hypoxia (Saraste, A., *Herz* 24:189-195, 1999; Ohtsuka, T. et al., *Coron. Artery Dis.* 10:221-225, 1999; James, T. N., *Coron. Artery Dis.* 9:291-307, 1998; Bialik, S. et al., *J. Clin. Invest.* 100:1363-1372, 1997; Long, X. et al., *J. Clin. Invest.* 99:2635-2643, 1997). Elevations in the plasma caspase-3 concentration may be associated with any physiological event that involves apoptosis. There is evidence that suggests apoptosis is induced in skeletal muscle during and following exercise and in cerebral ischemia (Carraro, U. and Franceschi, C., *Aging (Milano)* 9:19-34, 1997; MacManus, J. P. et al., *J. Cereb. Blood Flow Metab.* 19:502-510, 1999). The usefulness of caspase-3 as a marker of cardiac cell death is presently unknown, since there have been no published reports finding caspase-3 in the peripheral blood of patients with AMI. Interestingly, ischemia-induced apoptosis may have characteristics that distinguish it from other forms of apoptosis, but the induction of caspase-3 is common to all apoptotic pathways. Caspase-3 may not prove to be more useful than other cytosolic markers of cardiac cell death, since all of these markers are released following a loss of plasma membrane integrity. Evidence also suggests that cells undergoing apoptosis do not lose membrane integrity, a characteristic of necrosis, but rather, they form apoptotic bodies with intact membranes that are ultimately ingested by macrophages and other adjacent cells (Saraste, A., *Herz* 24:189-195, 1999; James, T. N., *Coron. Artery Dis.* 9:291-307, 1998). In this regard, the release of intracellular contents may be a result of necrosis, and caspase-3 may not be a suitable marker for the identification of cardiac cell death, particularly as a result of apoptosis.

Hemoglobin (Hb) is an oxygen-carrying iron-containing globular protein found in erythrocytes. It is a heterodimer of two globin subunits. $\alpha_2\gamma_2$ is referred to as fetal Hb, $\alpha_2\beta_2$ is called adult HbA, and $\alpha_2\delta_2$ is called adult HbA$_2$. 90-95% of hemoglobin is HbA, and the $\alpha_2$ globin chain is found in all Hb types, even sickle cell hemoglobin. Hb is responsible for carrying oxygen to cells throughout the body. Hb$\alpha_2$ is not normally detected in serum. The usefulness of Hb$\alpha_2$ on a ACS panel would be to determine the extent of hemolysis and the resulting contribution of erythrocyte-onginated proteins to the measured serum concentration. An accepted level of hemolysis would have to be established for the measurement of serum markers that are present in erythrocytes.

Human lipocalin-type prostaglandin D synthase (hPDGS), also called β-trace, is a 30 kDa glycoprotein that catalyzes the formation of prostaglandin D2 from prostaglandin H. The upper limit of hPDGS concentrations in apparently healthy individuals is reported to be approximately 420 ng/ml (Patent No. EP0999447A1). Elevations of hPDGS have been identified in blood from patients with unstable angina and cerebral infarction (Patent No. EP0999447A1). Furthermore, hPDGS appears to be a useful marker of ischemic episodes, and concentrations of hPDGS were found to decrease over time in a patient with angina pectoris following percutaneous transluminal coronary angioplasty (PTCA), suggesting that the hPGDS concentration decreases as ischemia is resolved (Patent No. EP0999447A1).

In a preferred embodiment, one or more specific marker of myocardial injury is combined with one or more non-specific marker of myocardial injury to create a diagnostic panel for ACS. In addition, the present invention provides methods for determining the components of such a plurality of markers. Once such a panel is assembled, the presence or level of each of the various markers is determined in one or more patient samples, and optionally compared to the diagnostic levels or normal levels of each marker.

Assay Measurement Strategies

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody.

Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvagable tissue, the appropriateness of drug therapies, the effectiveness of various therapies as indicated by reperfusion or resolution of symptoms, differentiation of the various types of ACS, identification of the severity of the event, identification of the disease severity, and identification of the patient's outcome, including risk of future events.

A panel consisting of the markers referenced above may be constructed to provide relevant information related to the diagnosis or prognosis of ACS and management of patients with ACS. Such a panel may be constucted using 1, 2, 3, 4, 5, 6, 7, 8, 9, 10, 15 or 20 individual markers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W.B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In another embodiment, the present invention provides a kit for the analysis of markers. Such a kit preferably comprises devises and reagents for the analysis of at least one test sample and instructions for performing the assay. Optionally the kits may contain one or more means for converting a marker level to a diagnosis or prognosis of the patient.

EXAMPLES

Example 1

Blood Sampling

Blood specimens were collected by trained study personnel. Samples were collected and processed as described previously. See, de Lemos et al., *The prognostic value of B-type natriuretic peptide in patients with acute coronary syndromes*, N Engl J Med 345:1014-21 (2001). Plasma samples were collected in citrate anticoagulant and frozen at the study site at −20° C. or colder within 60 minutes of collection. The specimens were shipped on dry ice to the TIMI Cardiac Marker Core Laboratory at Children's Hospital (Boston, Mass.) where they were stored at −70° C. Following completion of the OPUS-TIMI 16 trial, all plasma specimens from the 50/50 treatment arm were shipped on dry ice to BIOSITE, Inc. (San Diego, Calif.), where assays were performed.

Example 2

Biochemical Analyses

Markers were measured using standard immunoassay techniques. These techniques involved the use of antibodies to specifically bind the protein targets. A monoclonal antibody directed against a selected marker was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed. This formed the "anti-marker" in the microtiter plate. Another monoclonal antibody directed against the same marker was conjugated to alkaline phosphatase using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Immunoassays were performed on a TECAN Genesis RSP 200/8 Workstation. Biotinylated antibodies were pipetted into microtiter plate wells previously coated with avidin and incubated for 60 min. The solution containing unbound antibody was removed, and the cells were washed with a wash buffer, consisting of 20 mM borate (pH 7.42) containing 150 mM NaCl, 0.1% sodium azide, and 0.02% Tween-20. The plasma samples (10 µL) were pipetted into the microtiter plate wells, and incubated for 60 min. The sample was then removed and the wells were washed with a wash buffer. The antibody-alkaline phosphatase conjugate was then added to the wells and incubated for an additional 60 min, after which time, the antibody conjugate was removed and the wells were washed with a wash buffer. A substrate, (AttoPhos®, Promega, Madison, Wis.) was added to the wells, and the rate of formation of the fluorescent product was related to the concentration of the marker in the patient samples.

Assays for BNP were performed using murine anti-BNP monoclonal antibody 106.3 obtained from Scios Incorporated (Sunnyvale, Calif.). The hybridoma cell line secreting mAb 106.3 was generated from a fusion between FOX-NY cells and spleen cells from a Balb/c mouse immunized with human BNP 1-32 conjugated to BSA. A second murine anti-BNP antibody was produced by Biosite Incorporated (San Diego, Calif.) by antibody phage display as described previously (U.S. Pat. No. 6,057,098), using human BNP antigen (Scios Incorporated, Sunnyvale, Calif.; U.S. Pat. No. 5,114,923) conjugated to KLH by standard techniques. Human BNP antigen was also used for assay standardization.

Assays for MMP-9 were performed using murine anti-MMP-9 antibodies generated by Biosite Incorporated using phage display and recombinant protein expression as described previously (U.S. Pat. No. 6,057,098). Commercially available MMP-9 antigen was used for assay standardization (Calbiochem-Novabiochem Corporation, San Diego, Calif.). The immunogen used for antibody production was prepared by Biosite Incorporated. PCR primers were made corresponding to sequence at the 5'-end of human MMP-9 and the coding sequence at the 3'-end of human MMP-9 (Genbank accession number J05070). Six histidine codons inserted between the end of the coding sequence and the stop codon to assist in purification of the recombinant protein by metal-chelate affinity chromatography. The 5'-end MMP-9 primer, designated primer A, consisted of the nucleotide sequence as follows:
5'-AGGTGTCGTAAGCTTGAATTCAGACAC-CTCTGCCGCCACCATGAG -3' (SEQ ID NO:1). The 5' primer also contains 21 base pairs of pEAK12 vector sequence (Edge BioSystems, Gaithersburg, Md.) at its 5'-end corresponding to the EcoRI site and sequence immediately upstream. The 3'-end MMP-9 primer, designated primer B, consisted of the nucleotide sequence as follows:
5'-GGGCTGGCTTACCTGCGGCCTTAGT-GATGGTGATGGTGATGGTCCTCAGG GCACTG-CAGGATG-3' (SEQ ID NO:2). The 3' primer contains an additional 20 base-pairs of vector sequence, including 6 bases of the NotI site and the sequence immediately downstream, at its 5' end. The vector sequence at the 5'-ends of these primers will form, upon treatment with T4 DNA polymerase, single-stranded overhangs that are specific and complementary to those on the pEAK12 vector. The PCR amplification of the MMP-9 gene insert was done on a 2×100 µl reaction scale containing 100 pmol of 5' primer (A), 100 pmol of 3' primer (B), 2.5 units of Expand polymerase, 10 µl 2 mM dNTPs, 10 µl 10× Expand reaction buffer, 1 µl of Clontech Quick-clone human spleen cDNA (Clontech Laboratories, Palo Alto, Calif.) as template, and water to 100 µl. The reaction was carried out in a Perkin-Elmer thermal cycler as described in Example 18 (U.S. Pat. No. 6,057,098). The PCR products were precipitated and fractionated by agarose gel electrophoresis and full-length products excised from the gel, purified, and resuspended in water (Example 17, U.S. Pat. No. 6,057,098). The pEAK12 vector was prepared to receive insert by digestion with NotI and EcoRI (New England BioLabs, Beverly, Mass.). The insert and EcoRI/NotI digested pEAK12 vector were prepared for T4 exonuclease digestion by adding 1.0 µl of 10× Buffer A to 1.0 µg of DNA and bringing the final volume to 9 µl with water. The samples were digested for 4 minutes at 30° C. with 1 µl (1 U/µl) of T4 DNA polymerase. The T4 DNA polymerase was heat inactivated by incubation at 70° C. for 10 minutes. The samples were cooled, briefly centrifuged, and 45 ng of the digested insert added to 100 ng of digested pEAK12 vector in a fresh microfuge tube. After the addition of 1.0 µl of 10× annealing buffer, the volume was brought to 10 µl with water. The mixture was heated to 70° C. for 2 minutes and cooled over 20 minutes to room temperature, allowing the insert and vector to anneal. The annealed DNA was diluted one to four with distilled water and electroporated (Example 8, U.S. Pat. No. 6,057,098) into 30 µl of electrocompetent $E.$ $coli$ strain, DH10B (Invitrogen, Carlsbad, Calif.). The transformed cells were diluted to 1.0 ml with 2×YT broth and 10 µl, 100 µl, 300 µl plated on LB agar plates supplemented with ampicillin (75 µg/ml) and grown overnight at 37° C. Colonies were picked and grown overnight in 2×YT (75 µg/ml ampicillin at 37° C. The following day glycerol freezer stocks were made for long term storage at −80° C. The sequence of these clones (MMP9peak12) was verified at MacConnell Research (San Diego, Calif.) by the dideoxy chain termination method using a Sequatherm sequencing kit (Epicenter Technologies, Madison, Wis.), oligonucleotide primers C, 5'-TTCT-CAAGCCTCAGACAGTG-3' (SEQ ID NO:3), and D, 5'-CCTGGATGCAGGCTACTCTAG-3' (SEQ ID NO:4), that bind on the 5' and 3' side of the insert in the pEAK12 vector, respectively, and a LI-COR 4000L automated sequencer (LI-COR, Lincoln, Nebr.). Plasmid suitable for transfection and the subsequent expression and purification of human MMP-9 was prepared from clone MMP9peak12.2 using an EndoFree Plasmid Mega Kit as per manufacturer's recommendations (Qiagen, Valencia, Calif.). HEK 293 ("Peak") cells were expanded into a T-75 flask from a 1 ml frozen vial stock (5×10$^6$ cells/ml) in IS 293 medium (Irvine Scientific, Santa Ana, Calif.) with 5% fetal bovine serum (FBS) (JRH Biosciences, Lenexa, Kans.), 20 units/ml Heparin, 0.1% Pluronic F-68 (JRH Biosciences, Lenexa, Kans.), and 50 µg/ml Gentamicin (Sigma, St. Louis, Mo.). After incubating at 37° C., 85% humidity, and 5% $CO_2$ for 2-3 days, the cells were expanded into a T-175 flask while reducing the FBS to 2% in the medium. The cells were then continuously expanded 1:2 over a period of 2-3 weeks, establishing a consistent mono-layer of attached cells. Peak cells grown with the above method were centrifuged at 1000 rpm for 6 minutes, and the supernatant was discarded. After counting the cells to establish the density and checking for at least 90% viability with a standard dye test, the cells were resuspended at 5×10$^5$ cells/ml in 400 ml IS 293 with 2% FBS and 50 µg/ml Gentamicin and added to a 1 L spinner flask. Then, to a conical tube 5 ml IS 293 and 320 kg MMP-9 DNA were added per 400 ml spinner flask. This was mixed and incubated at room temperature for 2 minutes. 400 µl X-tremeGENE RO-1539 transfection reagent (Roche Diagnostics, Indianapolis, Ind.) per spinner was added to the tube that was then mixed and incubated at room temperature for 20 minutes. The mixture was added to the spinner flask, and incubated at 37° C., 85% humidity, and 5% $CO_2$ for 4 days at 100 rpm. The cell broth from the above spinner flask was spun down at 3500 rpm for 20 minutes, and the supernatant was saved for purification of the MMP-9. A column containing 20 ml Chelating Fast Flow resin (Amersham Pharmacia Biotech, Piscataway, N.J.) charged with $NiCl_2$ was equilibrated with BBS. Then the supernatant from the spinner flask was loaded on the column, washed with BBS+10 mM imidazole, and eluted with 200 mM imidazole. The elution was used for the load of the next purification step after adding $CaCl_2$ to 10 mM. A column with 5 ml gelatin sepharose 4B resin (Amersham Pharmacia Biotech, Piscataway, N.J.) was equilibrated with BBS+10 mM $CaCl_2$. After loading the antigen, the column was washed with equilibration buffer, and the MMP-9 was eluted using equilibration buffer+2% dimethyl sulfoxide (DMSO). Polyoxyethyleneglycol dodecyl ether (BRIJ-35) (0.005%) and EDTA (10 mM) were added to the elution, which was then dialyzed into the final buffer (50 mM Tris, 400 mM NaCl, 10 mM CaCl$_2$, 0.01% NaN$_3$, pH 7.5, 0.005% BRIJ-35, 10 mM EDTA). Finally, the protein was concentrated to approximately 0.25 mg/ml for storage at 4° C. Zymogram gels were used to check for production and purification of MMP-9. Western blots were also used to check for activity of the protein. MMP-9 (Oncogene Research Products, Cambridge, Mass.) was used for comparison of the purified antigen made using the PEAK cell system to known standards.

Assays for MMP-9 were performed using murine anti-MMP-9 antibodies generated at Biosite Incorporated, using phage display and recombinant protein expression techniques. Commercially available MMP-9 antigen was used for assay standardization (Calbiochem-Novabiochem Corporation, San Diego, Calif.). The concentration of MMP-9 was quantified by detecting the binding of alkaline phosphatase-conjugated antibody. The minimal detectable concentration for the assay was 0.3 ng/mL and the upper end of the reportable range was 2000 ng/mL.

Assays for Thrombus precursor Protein (TpP™) were performed using reagents obtained from American Biogenetic Sciences, Inc., Columbia, Md. Two murine monoclonal antibodies that recognize different epitopes on the soluble fibrin polymer were employed for the assay. The assay was calibrated using TpP™ supplied by American Biogenetic Sciences. Samples were diluted 1:4 prior to assay. The minimal detectable concentration was 0.25 μg/ml and the upper end of the reportable range was 25 μg/ml. Thus, samples between 1 μg/ml and 100 μg/ml would assay in the reportable range.

Assays for Monocyte Chemotactic protein-1 (MCP-1) were performed using antibodies developed at Biosite. The assays were developed in an immunometric (sandwich) format. The assays were calibrated with an in-house MCP-1 reference preparation. The minimal detectable concentration of the assay was 20 pg/ml and the upper end of the reportable range was 10,000 pg/mi.

Assays for various forms of troponin I (TIC complex and total TnI) were performed using a commercially available goat anti-TnI for capture and antibodies developed at Biosite as the enzyme-labeled conjugates. The assays were calibrated with in-house TIC complex and TnI reference solutions. The minimal detectable concentration for TnI was 40 pg/ml and was 50 pg/ml for the TIC complex. The upper end of the reportable range was 10,000 pg/ml for both assays.

Assays for fatty acid binding protein (FABP) were performed using commercially available monoclonal antibodies and a commercially available FABP antigen. The minimal detectable concentration was 6 ng/ml and the upper end of the reportable range was 10,000 ng/ml.

C-reactive protein (CRP) and fibrinogen were measured using commercially available assays (Dade Behring Inc, Newark, Del.).

Example 3

Exemplary Marker Panels

A marker panel can be constructed that contains markers of the various pathological events that result in myocardial damage. Such a panel would include markers of inflammation, atherosclerotic plaque rupture, platelet activation, thrombosis, and myocardial damage or necrosis. Suitable markers that may appear on this panel are IL-6, malondialdehyde-modified low-density lipoprotein (MDA-modified LDL), P-selectin, thrombin-antithrombin III (TAT) complex, BNP, free cardiac troponin I, total cardiac troponin I, cardiac troponin I in complexes with troponin T and/or C, free cardiac troponin T, total cardiac troponin T, cardiac troponin T in complexes with troponin I and/or C, C-reactive protein, and/or MMP-9. The marker panel will be evaluated in conjunction with the clinical signs and symptoms of the patient. Typically, patients with ACS have a predominant symptom of chest pain.

| Marker(s) Positive | Interpretation |
|---|---|
| IL-6 | Presence of an inflammatory response. Not specific for ACS, but may be indicative of an early event. |
| MDA-modified LDL | Indication of plaque rupture. May be indicative of an ongoing event, and that plaque rupture may be causing chest pain. |
| P-selectin | Indication of platelet activation. A platelet plug is forming or has formed. The platelet plug and the resulting occlusion may be causing chest pain. |
| TAT complex | Indication of coagulation activation. A clot is forming or has formed, and the resulting occlusion may be causing chest pain. |
| BNP | Indication of ventricular dysfunction. May be related to damage produced by cardiac ischemia. |
| Total cTnI | Indication of myocardial damage. Elevations are indicative of myocardial necrosis, and are produced by cardiac ischemia. |
| Total cTnTIC | Indication of myocardial damage. Elevations are indicative of myocardial necrosis, and are produced by cardiac ischemia. A high ratio of cTnTIC to total cTnI may be indicative of an ongoing event or continual ischemia. |

Elevations and changes over time of more than one marker on the panel may be indicative of the progression of ACS. For example, elevations of IL-6, MD-modified LDL, P-selectin, and TAT complex may indicate that atherosclerotic plaque rupture has occurred, and that the rupture has caused platelet aggregation and coagulation activation, resulting in a narrowing of the blood vessel. Furthermore, elevations of P-selectin and TAT complex may indicate that conditions are favorable for clot formation. Subsequent decreases in marker concentrations over time would indicate that the pathological process has been slowed or halted. For example, decreases in the TAT complex concentration over time would indicate that the coagulation process has been slowed or halted. In this regard, decreases in the MDA-modified LDL concentration over time would suggest that plaque rupture is not continuing.

Other markers may be substituted for or added to the markers listed in the example above. Alternative or additional markers of myocardial injury include annexin V, BNP and/or BNP-related peptides, β-enolase, creatine kinase-MB, glycogen phosphorylase-BB, heart-type fatty acid binding protein, phosphoglyceric acid mutase-MB, and S-100ao.

Alternative or additional markers of coagulation activation include plasmin-α-2-antiplasmin complex, fibrinopeptide A, prothrombin fragment 1+2, D-dimer, one or more forms of von Willebrand factor, tissue factor, and thrombus precursor protein (TpP).

Alternative or additional markers of platelet activation include β-thromboglobulin, platelet factor 4 and platelet-derived growth factor.

Alternative or additional markers of atherosclerotic plaque rupture include human neutrophil elastase, inducible nitric oxide synthase, lysophosphatidic acid, matrix metalloproteinase-1, matrix metalloproteinase-2, matrix metalloproteinase-3, and matrix metalloproteinase-9 (MMP-9).

Alternative or additional markers of inflammation or the acute phase response include C-reactive protein, interleukin-1β, interleukin-1 receptor antagonist, tumor necrosis factor α, soluble intercellular adhesion molecule-1, soluble vascular cell adhesion molecule-1, and monocyte chemotactic protein-1.

In addition, other markers can be added to the panel to enhance the diagnostic power of the panel.

Example 4

MMP-9, Total cTnI, cTnTIC, BNP, CRP, FABP, TpP, and MCP-1 as Prognostic Markers in ACS Study Population The Oral Glycoprotein IIb/IIIa Inhibition with Orbofiban in Patients with Unstable Coronary Syndromes (OPUS-TIMI 16) Trial was a randomized multicenter trial comparing an oral glycoprotein IIb/IIIa inhibitor, orbofiban, with placebo in 10,288 patients with ACS. See, Cannon et al., *Oral glycoprotein IIb/IIIa inhibition with orbofiban in patients with unstable coronary syndromes (OPUS-TIMI 16) trial*, Circulation 102:149-56 (2000). Patients were eligible for enrollment if they presented within 72 hours of the onset of ischemic symptoms and met one of the following criteria: age >65 with diabetes or vascular disease; prior coronary artery disease; dynamic ECG changes; or elevated cardiac markers. The study was approved by the Institutional Review Board of each hospital and all patients provided written informed consent. Patients were randomized to one of the following three treatment arms: orbofiban 50 mg twice daily (50/50 group), orbofiban 50 mg twice daily for one month, followed by orbofiban 30 mg twice daily (50/30 group), or placebo. The OPUS-TIMI 16 study was terminated prematurely because increased mortality was observed in the 50/30 group. No increase in mortality was observed in the 50/50 group. The present study was conducted in patients who were assigned to the 50/50 group and provided a baseline plasma specimen suitable for analysis of MMP-9, total cTnI, cTnTIC, BNP, CRP, FABP, TpP, and MCP-1.

The median time from the onset of symptoms to enrollment in OPUS-TIMI 16 was 40 hours.

MMP-9 Assay

Assays for MMP-9 were performed using murine anti-MMP-9 antibodies generated at Biosite Incorporated, using phage display and recombinant protein expression techniques. Commercially available MMP-9 antigen was used for assay standardization (Calbiochem-Novabiochem Corporation, San Diego, Calif.). Assays were performed in 384-well microtiter plates on a robotic high-throughput platform (TECAN Genesis RSP 200/8). The concentration of MMP-9 was quantified by detecting the binding of alkaline phosphatase-conjugated antibody. All samples were run in duplicate. The minimal detectable concentration for the assay was 3.0 ng/mL and the upper end of the reportable range was 2000 ng/mL.

Clinical Endpoints

All-cause mortality, nonfatal MI, and congestive heart failure were evaluated at 30 days and through the end of the 10-month follow-up period. MI was defined using previously reported criteria and adjudicated by a Clinical Events Committee. See, Antman et al., *Enoxaparin prevents death and cardiac ischemic events in unstable angina/non-Q-wave myocardial infarction: Results of the thrombolysis in myocardial infarction (TIMI) 11B trial*, Circulation 100:1593-601 (1999). The endpoint of new or worsening CHF or cardiogenic shock was collected from the case record forms and was not adjudicated.

Statistical Analyses

Subjects were divided into quartiles based on their marker concentration at the time of enrollment into the trial. Means and proportions for baseline variables were compared across quartiles using ANOVA for continuous variables and $\chi^2$ trend tests for categorical variables. The direct correlation between markers and other continuous baseline variables was assessed using Pearson's product moment correlation coefficient. The marker concentration was compared between patients who met a study endpoint and those who did not using the Wilcoxon Rank Sum Test. Cumulative hazard functions were used to estimate the frequency of adverse events at the end of the 10-month follow-up period. The log-rank test was used to compare outcomes across quartiles.

Analyses were performed in prespecified subgroups defined by age, gender, presence of diabetes, and index diagnosis. For all-cause mortality through the end of follow-up (10 months), a Cox proportional hazards model was constructed using forward stepwise selection. Clinical variables were entered into the model if they had a univariate p value <0.1, and if data were available in >75% of patients; variables were removed if they had a multivariate p value >0.1. Baseline concentrations of total cTnI, BNP, and MMP-9 were then added into the completed model. Only patients with complete data for all variables were included in these multivariate analyses (n=2068). The model was subsequently repeated in the subset of patients who had undergone measurement of C-reactive protein (n=736).

Association of MMP-9 with Baseline Clinical Variables

Higher baseline levels of MMP-9 were associated with female gender, nonwhite race and current tobacco use, but not with older age, diabetes, or prior evidence of hypercholesterolemia, coronary disease or congestive heart failure. Higher MMP-9 levels were associated with faster heart rate, Killip Class >I, and elevated levels of troponin I and C-reactive protein. (table 1) In contrast, MMP-9 was not associated with body mass index, renal function, electrocardiographic changes, elevated BNP, LVEF, or the extent of coronary artery disease measured at coronary angiography. There was no association between the concentration of MMP-9 and the time from symptom onset to enrollment in the trial. The correlations between the concentrations of MMP-9 and CRP (R=0.16; p<0.001), cTnI (R=0.07; p=0.001), and peak recorded CKMB (R=0.05; p=0.04) were only modest. There was no association between the concentration of MMP-9 and BNP (R=0.005; p=0.82) or fibrinogen (R=-0.05; p=0.12).

TABLE 1

Baseline Clinical Characteristics According to Quartiles of MMP-9 (ng/mL)

| | Quartile 1 | Quartile 2 | Quartile 3 | Quartile 4 | p trend | p Q4 vs Q1 |
|---|---|---|---|---|---|---|
| Range, ng/mL | 3.0-24.3 | 24.4-43.1 | 43.2-85.2 | 85.3-2000 | | |
| n | 580 | 573 | 581 | 577 | | |
| Time to randomization (hrs) | 43 ± 19 | 40 ± 20 | 41 ± 20 | 39 ± 20 | 0.09 | 0.02 |
| Age (years) | 61 ± 12 | 60 ± 12 | 61 ± 11 | 61 ± 12 | 0.48 | 0.94 |
| Male | 441 (76%) | 404 (71%) | 418 (72%) | 397 (69%) | 0.02 | 0.006 |
| White | 558 (96%) | 537 (94%) | 557 (96%) | 519 (90%) | <0.001 | <0.001 |
| Past Medical History | | | | | | |
| Hypertension | 240 (41%) | 244 (43%) | 237 (41%) | 256 (44%) | 0.42 | 0.29 |
| Congestive Heart Failure | 22 (4%) | 34 (6%) | 31 (5%) | 32 (6%) | 0.26 | 0.16 |
| Coronary artery disease | 280 (48%) | 305 (53%) | 291 (51%) | 276 (48%) | 0.64 | 0.88 |
| Peripheral vascular disease | 32 (6%) | 41 (7%) | 49 (8%) | 34 (6%) | 0.60 | 0.78 |
| Cerebrovascular disease | 10 (2%) | 20 (3%) | 22 (4%) | 16 (3%) | 0.27 | 0.23 |
| Diabetes | 127 (22%) | 111 (19%) | 125 (22%) | 133 (23%) | 0.46 | 0.63 |
| Hypercholesterolemia | 156 (27%) | 162 (28%) | 180 (31%) | 152 (26%) | 0.89 | 0.83 |
| Smoking status: | | | | | | |
| Current smoker | 182 (31%) | 201 (35%) | 210 (36%) | 241 (42%) | <0.001 | <0.001 |
| Never smoker | 216 (37%) | 181 (32%) | 173 (30%) | 164 (29%) | 0.005 | 0.005 |
| Past smoker | 180 (31%) | 191 (33%) | 197 (34%) | 170 (30%) | 0.64 | 0.56 |
| Index Diagnosis: | | | | | | |
| ST elevation MI | 183 (32%) | 165 (29%) | 184 (32%) | 218 (38%) | 0.02 | 0.03 |
| Non ST elevation MI | 127 (22%) | 119 (21%) | 145 (25%) | 127 (22%) | 0.56 | 0.96 |
| Unstable angina | 270 (46%) | 288 (50%) | 252 (43%) | 232 (40%) | 0.005 | 0.03 |
| Physical findings | | | | | | |
| BMI kg/m$^2$ | 28 ± 15 | 28 ± 5 | 29 ± 13 | 28 ± 5 | 0.84 | 0.87 |
| Systolic BP (mm Hg) | 130 ± 21 | 129 ± 21 | 127 ± 21 | 129 ± 21 | 0.27 | 0.73 |
| HR (BPM) | 72 + 14 | 71 + 13 | 73 + 14 | 75 + 15 | <0.001 | <0.001 |
| Killip Class II-IV | 34 (6%) | 42 (7%) | 66 (12%) | 64 (11%) | <0.001 | 0.001 |
| Diagnostic Testing | | | | | | |
| Creatinine clearance ≦90 | 223 (40%) | 203 (37%) | 214 (38%) | 221 (40%) | 0.83 | 0.92 |
| CK-MB > ULN | 279 (72%) | 264 (73%) | 305 (76%) | 311 (76%) | 0.15 | 0.23 |
| cTnI >1.5 ng/ml | 144 (25%) | 137 (24%) | 159 (28%) | 187 (33%) | 0.002 | 0.006 |
| BNP >80 pg/ml | 278 (49%) | 274 (48%) | 313 (55%) | 290 (51%) | 0.18 | 0.48 |
| CRP >1.5 ng/ml | 55 (38%) | 74 (34%) | 102 (43%) | 128 (55%) | <0.001 | 0.002 |
| ST deviation >1 mm | 288 (50%) | 262 (46%) | 264 (45%) | 267 (46%) | 0.26 | 0.25 |
| Extent of CAD (50% stenosis) | | | | | | |
| 0 vessel | 17 (7%) | 18 (6%) | 22 (7%) | 26 (8%) | 0.42 | 0.49 |
| 1 vessel | 77 (30%) | 100 (34%) | 113 (35%) | 110 (34%) | 0.29 | 0.26 |
| 2 vessel | 70 (27%) | 90 (31%) | 89 (28%) | 85 (27%) | 0.60 | 0.85 |
| 3 vessel | 92 (36%) | 83 (29%) | 98 (30%) | 98 (31%) | 0.31 | 0.19 |
| Positive Exercise Test | 77 (36%) | 62 (36%) | 74 (41%) | 69 (38%) | 0.44 | 0.63 |
| Ejection Fraction (%) | 55 + 12 | 55 + 13 | 53 + 13 | 53 + 14 | 0.09 | 0.07 |

Association of MMP-9 with Clinical Outcomes

The concentration of MMP-9 was significantly higher among patients who died by 30 days (p=0.002) or by 10 months (p<0.0001) vs. those who were alive at either time point. Similarly, MMP-9 concentrations were higher among patients with nonfatal MI and those with CHF than those free of these endpoints. (p<0.01 for each endpoint at both 30 days and 10 months.

TABLE 2

Association between baseline MMP-9 concentration (ng/mL) and outcomes

| Outcome | n | Median [25, 75] | p value |
|---|---|---|---|
| 30 days | | | |
| Dead | 34 | 65 [39, 151] | 0.002 |
| Alive | 2277 | 43 [24, 85] | |
| Nonfatal MI | 61 | 65 [37, 110] | 0.006 |
| No MI | 2250 | 43 [24, 85] | |
| CHF | 46 | 65 [35, 147] | 0.008 |
| No CHF | 2265 | 43 [24, 85] | |
| Death, MI, or CHF | 116 | 65 [36, 145] | <0.001 |
| No Death MI, or CHF | 2195 | 42 [24, 84] | |
| 10 months | | | |
| Dead | 78 | 64 [39, 142] | <0.001 |
| Alive | 2233 | 43 [24, 85] | |
| Nonfatal MI | 112 | 57 [33, 109] | 0.002 |
| No MI | 2199 | 43 [24, 84] | |
| CHF | 67 | 64 [37, 142] | 0.002 |
| No CHF | 2244 | 43 [24, 85] | |
| Death, MI, or CHF | 205 | 64 [35, 118] | <0.001 |
| No Death MI, or CHF | 2106 | 42 [24, 83] | |

Unadjusted mortality increased with each successive quartile of MMP-9 concentration (p<0.001). Similar associations were observed between MMP-9 and the composite of death and nonfatal MI (p<0.001) and between MMP-9 and congestive heart failure (p<0.001). A directionally consistent association was observed between MMP-9 and mortality in subgroups of patients defined by time from symptom onset to treatment, index diagnosis, gender, diabetes, and age.

ease, absence of hypertension requiring treatment, and tobacco use, but not with older age or race. Higher total ctnI levels were associated with renal function, electrocardiographic changes, Killip Class >I, and elevated levels of CK-MB. (Table 4) In contrast, total ctnI was not associated with body mass index, the extent of coronary artery disease measured at coronary angiography, stress test, or race. There was no association between the concentration of total cTnI

TABLE 3

Subgroup analyses for 10-month mortality

| Group | n | Quartile 1 | Quartile 2 | Quartile 3 | Quartile 4 | p trend | p q4 v q1 |
|---|---|---|---|---|---|---|---|
| All pts | 2311 | 3 (0.5%) | 20 (4.3%) | 27 (6.1%) | 28 (6.3%) | <0.001 | <0.001 |
| Time CP to randomization | | | | | | | |
| 0-24 hrs | 508 | 0 (0%) | 4 (4.8%) | 10 (12.9%) | 7 (5.3%) | 0.02 | 0.02 |
| >24-48 hrs | 915 | 0 (0%) | 9 (4.6%) | 9 (4.5%) | 15 (8.5%) | 0.003 | <0.001 |
| >48 hrs | 862 | 2 (0.9%) | 6 (2.9%) | 8 (4.3%) | 6 (4.9%) | 0.28 | 0.11 |
| Index dx | | | | | | | |
| STEMI | 750 | 0 (0%) | 4 (2.5%) | 8 (5.1%) | 9 (6.2%) | <0.05 | 0.008 |
| NSTEMI | 518 | 1 (0.8%) | 7 (8.7%) | 7 (5.5%) | 10 (9.8%) | 0.07 | 0.008 |
| UAP | 1042 | 2 (0.8%) | 9 (3.7%) | 12 (6.7%) | 9 (4.7%) | 0.07 | 0.02 |
| Gender | | | | | | | |
| male | 1660 | 2 (0.5%) | 12 (3.9%) | 20 (6.5%) | 16 (5.7%) | 0.002 | <0.001 |
| female | 651 | 1 (0.7%) | 8 (5.0%) | 7 (5.1%) | 12 (7.3%) | 0.08 | 0.008 |
| Diabetes | | | | | | | |
| present | 496 | 1 (0.8%) | 6 (5.8%) | 6 (5.5%) | 12 (11.6%) | 0.03 | 0.003 |
| absent | 1814 | 2 (0.5%) | 14 (3.9%) | 21 (6.3%) | 16 (4.7%) | 0.003 | 0.001 |
| Age | | | | | | | |
| <65 | 1402 | 0 (0%) | 4 (1.4%) | 14 (4.9%) | 8 (3.4%) | 0.001 | 0.006 |
| >65 | 896 | 3 (1.4%) | 16 (9.2%) | 13 (8.1%) | 20 (10.9%) | 0.007 | <0.001 |

The percentages represent survival estimates.

Association of Total cTnI with Baseline Clinical Variables

Data were evaluated from 2523 patients. Higher baseline levels of total ctnI were associated with male gender, absence of diabetes, absence of prior coronary artery disease and the time from symptom onset to enrollment in the trial. There was no association between the concentration of total cTnI and CRP (R=0.05; p=0.16) or fibrinogen (R=0.04; p=0.18) (Table 5).

TABLE 4

Association between Baseline Variables and Quartiles of Baseline Marker Concentrations
Total Troponin I

|  | ≦53.6 | 53.6-346 | 346-1816 | >1816 | p trend | p Q4 vs Q1 |
|---|---|---|---|---|---|---|
| Range of marker levels | 0-53.6 | 53.8-346 | 346.6-1811.5 | 1820.3-69719 | | |
| Time from onset to rando (hrs) | 36.99 ± 20.53 | 41.29 ± 20.7 | 44.28 ± 20.06 | 37.74 ± 17.74 | 0.1518 | 0.5085 |
| Age (years) | 61.66 ± 11.41 | 61.58 ± 11.49 | 60.04 ± 11.45 | 59.24 ± 11.65 | 0 | 0.0002 |
| Male | 409 (64.7%) | 437 (69.4%) | 464 (73.7%) | 506 (80.2%) | 0 | 0 |
| White | 596 (94.3%) | 590 (93.7%) | 589 (93.5%) | 597 (94.6%) | 0.8565 | 0.811 |
| Hypertension req rx | 308 (48.7%) | 297 (47.2%) | 223 (35.5%) | 230 (36.5%) | 0 | 0 |
| Prior CAD$ | 441 (69.8%) | 367 (58.3%) | 258 (41%) | 194 (30.7%) | 0 | 0 |
| PCI for index event | 120 (19%) | 179 (28.4%) | 170 (27%) | 206 (32.6%) | 0 | 0 |
| Periph AVD | 58 (9.2%) | 54 (8.6%) | 39 (6.2%) | 28 (4.4%) | 0.0003 | 0.001 |
| Prior CVA/TIA+ | 45 (7.1%) | 46 (7.3%) | 34 (5.4%) | 30 (4.8%) | 0.0359 | 0.0771 |
| Diabetes | 158 (25%) | 147 (23.3%) | 131 (20.8%) | 118 (18.7%) | 0.0038 | 0.0071 |
| Family history of CAD | 258 (41.2%) | 273 (43.8%) | 237 (37.9%) | 240 (38.3%) | 0.098 | 0.2985 |
| Hypercholesterolemia | 225 (35.7%) | 210 (33.4%) | 154 (24.5%) | 121 (19.2%) | 0 | 0 |
| Current smoker | 169 (26.9%) | 220 (34.9%) | 256 (40.7%) | 276 (43.9%) | 0 | 0 |
| Never smoker | 223 (35.5%) | 203 (32.2%) | 191 (30.4%) | 178 (28.3%) | | |
| Past smoker | 236 (37.6%) | 207 (32.9%) | 182 (28.9%) | 175 (27.8%) | | |
| STEMI | 38 (6%) | 99 (15.7%) | 262 (41.7%) | 428 (67.8%) | 0 | 0 |
| NSTEMI | 36 (5.7%) | 114 (18.1%) | 240 (38.2%) | 172 (27.3%) | | |
| UA | 557 (88.3%) | 417 (66.2%) | 127 (20.2%) | 31 (4.9%) | | |

TABLE 4-continued

Association between Baseline Variables and Quartiles of Baseline Marker Concentrations
Total Troponin I

|  | ≤53.6 | 53.6-346 | 346-1816 | >1816 | p trend | p Q4 vs Q1 |
|---|---|---|---|---|---|---|
| Aspirin prior | 353 (55.9%) | 309 (49.2%) | 205 (32.5%) | 144 (22.8%) | 0 | 0 |
| Prior heparin | 502 (79.4%) | 551 (87.6%) | 568 (90.2%) | 590 (93.5%) | 0 | 0 |
| Beta blockers prior | 242 (38.4%) | 201 (31.9%) | 139 (22.1%) | 112 (17.8%) | 0 | 0 |
| Hypolipidemic agents prior | 178 (28.3%) | 160 (25.6%) | 109 (17.4%) | 84 (13.3%) | 0 | 0 |
| BMI | 28.84 ± 14.67 | 28.62 ± 12.23 | 27.96 ± 4.71 | 27.9 ± 4.58 | 0.0568 | 0.1028 |
| Systolic BP (mm Hg) | 132.16 ± 20.76 | 131.93 ± 21.19 | 126.62 ± 20.01 | 124.58 ± 19.98 | 0 | 0 |
| Diastolic BP (mm Hg) | 75.33 ± 12.28 | 74.71 ± 12.16 | 73.58 ± 12.52 | 73.28 ± 12.97 | 0.0011 | 0.0037 |
| Killip II-IV | 53 (8.5%) | 52 (8.4%) | 52 (8.3%) | 76 (12.1%) | 0.0433 | 0.0407 |
| Creatinine clearance ≤90 | 260 (43%) | 227 (38.3%) | 217 (35.9%) | 202 (33.9%) | 0.0008 | 0.0012 |
| CK > ULN | 99 (17.6%) | 210 (36%) | 503 (83.6%) | 603 (97.7%) | 0 | 0 |
| CK-MB > ULN | 93 (29.7%) | 200 (55.9%) | 445 (90.8%) | 516 (98.1%) | 0 | 0 |
| CTnI ≥0.4 ng/mg | 42 (32.3%) | 114 (62.6%) | 126 (84%) | 123 (83.7%) | 0 | 0 |
| ST depression >0.5 mm | 269 (42.6%) | 292 (46.3%) | 313 (49.7%) | 354 (56.1%) | 0 | 0 |
| T wave inversion >3 mm | 176 (27.8%) | 170 (27%) | 154 (24.4%) | 124 (19.7%) | 0.0004 | 0.0006 |
| New LBBB | 12 (2%) | 14 (2.3%) | 7 (1.1%) | 8 (1.3%) | 0.1663 | 0.3411 |
| Angiography: number of vessels with ≥50% stenosis | | | | | | |
| None | 0 (0%) | 0 (0%) | 0 (0%) | 0 (0%) | 0.9572 | 1 |
| 1 vessel | 3 (18.8%) | 1 (5%) | 4 (17.4%) | 2 (6.5%) | | |
| 2 vessel | 10 (62.5%) | 12 (60%) | 8 (34.8%) | 22 (71%) | | |
| ≥3 vessels | 3 (18.8%) | 7 (35%) | 11 (47.8%) | 7 (22.6%) | | |
| LVEF (%) | 53.98 ± 13.35 | 56.13 ± 11.82 | 55.88 ± 12.55 | 50.42 ± 12.01 | 0.043 | 0.0556 |
| Stress test positive | 67 (39.4%) | 61 (34.5%) | 87 (38.8%) | 79 (36.7%) | 0.5179 | 0.4108 |
| Stress test indeterminate | 29 (17.1%) | 29 (16.4%) | 28 (12.5%) | 31 (14.4%) | | |
| Stress test negative | 74 (43.5%) | 87 (49.2%) | 109 (48.7%) | 105 (48.8%) | | |

$^\$$Prior CAD: previous MI, documented unstable angina, angina pectoris, angiographically confirmed CAD, prior PTCR or CABG not for index event.
$^+$Prior CVA/TIA: Cerebrovascular arterial disease, prior non-haemorrhagic stroke or prior TIA.

TABLE 5

Simple Correlation between Baseline Marker Levels & Continuous Baseline Variables
Total Troponin I

|  | R value | p* |
|---|---|---|
| Age (years) | 0.05 | 0.0113 |
| BMI | 0.02 | 0.3959 |
| Maximum recorded CK-MB (% of ULN) | 0.36 | 0 |
| CRP (mg/dl) | 0.05 | 0.1591 |
| Fibrinogen (mg · dl) | 0.04 | 0.1752 |
| LVEF (%) | 0.19 | 0.0003 |
| Creatinine clearance | 0.03 | 0.1333 |

*p value based on Pearson's product moment correlation coefficient.

The p value based on Pearson's product moment correlation coefficient tests whether a linear relationship between the marker and the baseline variable is valid. The R value indicates how closely the observed points are to the fitted line.

Association of total cTnI with Clinical Outcomes

The concentration of total cTnI was significantly higher among patients who died by 30 days (p=0.004) vs. those who were alive at the same time point. Similarly, total cTnI concentrations were higher among patients with a combined endpoint of death or nonfatal MI than those free of these endpoints. (p<0.01 for each endpoint at both 30 days and 10 months (Tables 6 and 7).

TABLE 6

Correlation between Baseline Marker Concentrations and 30 Day Outcomes
Total Troponin I

| Outcome | n | mean ± SD | median (25, 75) | p |
|---|---|---|---|---|
| Dead | 40 | 4656.93 ± 10309.66 | 1293.5 (104.3, 4990.12) | 0.0041 |
| Alive | 2483 | 2144.1 ± 5384.8 | 335.4 (53.45, 1775.8) | |
| MI | 70 | 3248.72 ± 10172.18 | 219.9 (67.9, 1820.75) | 0.1006 |
| No MI | 2453 | 2153.55 ± 5310.15 | 346.6 (53.2, 1811.5) | |
| Ischemia -> Urgent Revasc | 81 | 2226.51 ± 5366.63 | 470.8 (70.1, 1744.4) | 0.9436 |
| No Ischemia -> Urgent Revasc | 2442 | 2182.52 ± 5508.1 | 338.5 (53.52, 1818.1) | |
| Death/MI | 103 | 3901.2 ± 10514.31 | 387.3 (69.6, 3380.4) | 0.0012 |
| No Death/MI | 2420 | 2110.84 ± 5174.48 | 337 (52.68, 1761.45) | |
| Death/MI/Ischemia -> Urgent Revasc | 180 | 3181.58 ± 8743.16 | 433.85 (69.77, 2287.88) | 0.0116 |
| No Death/MI/Ischemia -> Urgent Revasc | 2343 | 2107.29 ± 5165.32 | 333.7 (52.55, 1775.8) | |

TABLE 7

Correlation between Baseline Marker Concentrations and 10 Month Outcomes
Total Troponin I

| Outcome | n | mean ± SD | median (25, 75) | p |
|---|---|---|---|---|
| Dead | 86 | 3309.64 ± 7830.37 | 541.95 (94.72, 3882.3) | 0.0535 |
| Alive | 2437 | 2144.21 ± 5400.14 | 335.4 (52.9, 1744.4) | |
| MI | 123 | 2758.01 ± 8494.07 | 200.7 (66.7, 1497.6) | 0.2356 |
| No MI | 2400 | 2154.51 ± 5305.09 | 351.3 (52.92, 1829.52) | |
| Ischemia -> Urgent Revasc | 145 | 1981.8 ± 4703.86 | 335.4 (70.1, 1519.8) | 0.6488 |
| No Ischemia -> Urgent Revasc | 2378 | 2196.26 ± 5548.18 | 346.3 (53.42, 1826.83) | |
| Death/MI | 190 | 3181.92 ± 8575.64 | 340.45 (69.8, 2632.88) | 0.0093 |
| No Death/MI | 2333 | 2102.66 ± 5166.94 | 346 (52.4, 1766.1) | |
| Death/MI/Ischemia -> Urgent Revasc | 328 | 2678.37 ± 7245.55 | 346.5 (69.97, 1876.8) | 0.081 |
| No Death/MI/Ischemia -> Urgent Revasc | 2195 | 2110.05 ± 5190.23 | 346 (52.1, 1804.2) | |

Association of cTnTIC with Baseline Clinical Variables

Data were evaluated from 2439 patients. Higher baseline levels of cTnTIC were associated with male gender, absence of diabetes, absence of prior coronary artery disease, absence of hypertension requiring treatment, and tobacco use, but not with older age or race. Higher cTnTIC levels were associated with renal function, electrocardiographic changes, Killip Class >I, elevated levels of cTnI, and elevated levels of CK-MB. (Table 8) In contrast, cTnTIC was not associated with body mass index, the extent of coronary artery disease measured at coronary angiography, stress test, or race. There was no association between the concentration of cTnTIC and CRP (R=0.03; p=0.36) or fibrinogen (R=0.04; p=0.29) (Table 9).

TABLE 8

Association between Baseline Variables and Quartiles of Baseline Marker Concentrations
Troponin TIC Complex

| | ≤16.65 | 16.65-65.8 | 65.8-195 | >195 | p trend | p Q4 vs Q1 |
|---|---|---|---|---|---|---|
| Range of marker levels | 0-16.6 | 16.7-65.8 | 65.9-193.4 | 196.6-58658.8 | | |
| Time from onset to rando (hrs) | 41.05 ± 20.31 | 43.25 ± 20.49 | 42.53 ± 20.82 | 33.35 ± 16.43 | 0 | 0 |
| Age (years) | 61.8 ± 11.64 | 60.76 ± 11.53 | 60.69 ± 11.35 | 59.75 ± 11.69 | 0.003 | 0.002 |
| Male | 381 (62.5%) | 437 (71.6%) | 437 (71.8%) | 484 (79.3%) | 0 | 0 |
| White | 579 (94.9%) | 570 (93.4%) | 571 (93.8%) | 583 (95.6%) | 0.5822 | 0.5904 |
| Hypertension req rx | 282 (46.3%) | 269 (44.2%) | 253 (41.5%) | 226 (37.1%) | 0.0008 | 0.0012 |
| Prior CAD$ | 383 (62.8%) | 356 (58.4%) | 282 (46.3%) | 207 (33.9%) | 0 | 0 |
| PCI for index event | 149 (24.4%) | 134 (22%) | 175 (28.7%) | 185 (30.3%) | 0.0022 | 0.021 |
| Periph AVD | 56 (9.2%) | 56 (9.2%) | 32 (5.3%) | 30 (4.9%) | 0.0004 | 0.0041 |
| Prior CVA/TIA+ | 47 (7.7%) | 38 (6.2%) | 32 (5.3%) | 33 (5.4%) | 0.0715 | 0.1071 |
| Diabetes | 154 (25.2%) | 118 (19.3%) | 142 (23.3%) | 119 (19.5%) | 0.0789 | 0.017 |
| Family history of CAD | 252 (41.7%) | 245 (40.4%) | 254 (42.1%) | 226 (37.4%) | 0.2088 | 0.1261 |
| Hypercholesterolemia | 192 (31.5%) | 200 (32.8%) | 162 (26.6%) | 125 (20.6%) | 0 | 0 |
| Current smoker | 196 (32.3%) | 212 (34.8%) | 219 (36.1%) | 255 (41.9%) | 0.0026 | 0.0118 |
| Never smoker | 220 (36.3%) | 180 (29.5%) | 193 (31.8%) | 181 (29.7%) | | |
| Past smoker | 190 (31.4%) | 218 (35.7%) | 195 (32.1%) | 173 (28.4%) | | |
| STEMI | 74 (12.2%) | 125 (20.5%) | 222 (36.5%) | 374 (61.3%) | 0 | 0 |
| NSTEMI | 99 (16.3%) | 117 (19.2%) | 146 (24%) | 182 (29.8%) | | |
| UA | 436 (71.6%) | 367 (60.3%) | 241 (39.6%) | 54 (8.9%) | | |

TABLE 8-continued

Association between Baseline Variables and Quartiles of Baseline Marker Concentrations
Troponin TIC Complex

|  | ≦16.65 | 16.65-65.8 | 65.8-195 | >195 | p trend | p Q4 vs Q1 |
|---|---|---|---|---|---|---|
| Aspirin prior | 288 (47.3%) | 305 (50%) | 235 (38.7%) | 149 (24.5%) | 0 | 0 |
| Prior heparin | 520 (85.2%) | 505 (82.8%) | 537 (88.2%) | 572 (93.9%) | 0 | 0 |
| Beta blockers prior | 200 (32.8%) | 199 (32.6%) | 168 (27.6%) | 110 (18%) | 0 | 0 |
| Hypolipidemic agents prior | 152 (25.1%) | 149 (24.5%) | 116 (19.1%) | 88 (14.4%) | 0 | 0 |
| BMI | 28.76 ± 14.91 | 28.26 ± 5.15 | 28.41 ± 12.33 | 27.92 ± 4.55 | 0.2118 | 0.162 |
| Systolic BP (mm Hg) | 131.87 ± 21.13 | 129.72 ± 20.49 | 128.98 ± 20.62 | 125.55 ± 20.25 | 0 | 0 |
| Diastolic BP (mm Hg) | 74.95 ± 12.5 | 74.75 ± 11.88 | 74.32 ± 12.44 | 73.38 ± 13.3 | 0.0244 | 0.0296 |
| Killip II-IV | 40 (6.7%) | 49 (8.1%) | 62 (10.3%) | 77 (12.7%) | 0.0002 | 0.0005 |
| Creatinine clearance ≦90 | 239 (41.6%) | 230 (39.4%) | 222 (38.9%) | 193 (33%) | 0.0036 | 0.0025 |
| CK > ULN | 161 (29%) | 253 (45.2%) | 373 (65.7%) | 570 (95%) | 0 | 0 |
| CK-MB > ULN | 173 (50.6%) | 211 (59.6%) | 336 (78.9%) | 484 (96.8%) | 0 | 0 |
| CTnI ≧0.4 ng/mg | 81 (54%) | 78 (55.3%) | 109 (73.6%) | 117 (81.8%) | 0 | 0 |
| ST depression >0.5 mm | 274 (44.9%) | 271 (44.4%) | 309 (50.7%) | 344 (56.4%) | 0 | 0.0001 |
| T wave inversion >3 mm | 170 (27.9%) | 169 (27.7%) | 138 (22.7%) | 126 (20.7%) | 0.0007 | 0.0034 |
| New LBBB | 10 (1.7%) | 13 (2.2%) | 8 (1.3%) | 10 (1.7%) | 0.6932 | 0.9698 |
| Angiography: number of vessels with ≧50% stenosis | | | | | | |
| None | 0 (0%) | 0 (0%) | 0 (0%) | 0 (0%) | 0.3038 | 1 |
| 1 vessel | 5 (45.5%) | 1 (4.3%) | 2 (8%) | 2 (8%) | | |
| 2 vessel | 5 (45.5%) | 13 (56.5%) | 15 (60%) | 15 (60%) | | |
| ≧3 vessels | 1 (9.1%) | 9 (39.1%) | 8 (32%) | 8 (32%) | | |
| LVEF (%) | 53.49 ± 11.36 | 58.29 ± 12.34 | 53.84 ± 13.35 | 50.53 ± 12.17 | 0.0203 | 0.1235 |
| Stress test positive | 70 (40.5%) | 79 (38%) | 60 (32.8%) | 71 (37.4%) | 0.6382 | 0.5086 |
| Stress test indeterminate | 25 (14.5%) | 34 (16.3%) | 31 (16.9%) | 27 (14.2%) | | |
| Stress test negative | 78 (45.1%) | 95 (45.7%) | 92 (50.3%) | 92 (48.4%) | | |

$Prior CAD: previous MI, documented unstable angina, angina pectoris, angiographically confirmed CAD, prior PTCR or CABG not for index event.
+Prior CVA/TIA: Cerebrovascular arterial disease, prior non-haemorrhagic stroke or prior TIA.

TABLE 9

Simple Correlation between Baseline Marker Levels & Continuous Baseline Variables
Troponin TIC Complex

|  | R value | p* |
|---|---|---|
| Age (years) | 0.02 | 0.3448 |
| BMI | 0 | 0.9317 |
| Maximum recorded CK-MB (% of ULN) | 0.22 | 0 |
| CRP (mg/dl) | 0.03 | 0.3579 |
| Fibrinogen (mg · dl) | 0.04 | 0.2861 |
| LVEF (%) | 0.07 | 0.186 |
| Creatinine clearance | 0.03 | 0.1679 |

*p value based on Pearson's product moment correlation coefficient.

The p value for Pearson's product moment correlation coefficient tests whether a linear relationship between the marker and the baseline variable is valid. The R value indicates how closely the observed points are to the fitted line.

Association of cTnTIC with Clinical Outcomes

The concentration of cTnTIC was significantly higher among patients who died by 30 days (p<0.05) vs. those who were alive at the same time point (Table 10). The trend of lower quartile cTnTIC concentrations was associated with an increased frequency of ischemia requiring urgent revascularization at 10 months (Table 11). In contrast, the trend of higher quartile cTnTIC concentrations was associated with an increased frequency of death, ischemia requiring urgent revascularization, and the combined endpoint of death, non-fatal MI, or ischemia requiring urgent revascularization at 30 days post-event in patients with no history of smoking (Table 12).

TABLE 10

Correlation between Baseline Marker Concentrations and 30 Day Outcomes
Troponin TIC Complex

| Outcome | n | mean ± SD | median (25, 75) | p |
|---|---|---|---|---|
| Dead | 40 | 1255.76 ± 3208.86 | 163.3 (23.15, 973.55) | 0.0492 |
| Alive | 2399 | 479.48 ± 2460.34 | 65.5 (16.65, 188.85) | |
| MI | 70 | 685.68 ± 2837.65 | 50.75 (6.25, 287.27) | 0.5071 |
| No MI | 2369 | 486.49 ± 2464.51 | 66.3 (17, 193.2) | |
| Ischemia -> Urgent Revasc | 82 | 411.49 ± 1422.44 | 82.95 (15.7, 260.42) | 0.764 |
| No Ischemia -> Urgent Revasc | 2357 | 495.02 ± 2504.38 | 65.6 (16.7, 189.6) | |
| Death/MI | 103 | 933.03 ± 3070.43 | 64.3 (12.35, 442.65) | 0.0648 |
| No Death/MI | 2336 | 472.77 ± 2444.99 | 65.85 (16.95, 188.42) | |

TABLE 10-continued

Correlation between Baseline Marker Concentrations and 30 Day Outcomes
Troponin TIC Complex

| Outcome | n | mean ± SD | median (25, 75) | p |
|---|---|---|---|---|
| Death/MI/Ischemia -> Urgent Revasc | 181 | 710.78 ± 2513.32 | 66.1 (12.8, 334.3) | 0.2171 |
| No Death/MI/Ischemia -> Urgent Revasc | 2258 | 474.69 ± 2472.24 | 65.7 (17, 187.05) | |

TABLE 11

Associations between Baseline Marker Concentrations and 10 Month Outcomes
Troponin TIC Complex

| | ≦16.65 | | 16.65-65.8 | | 65.8-195 | | >195 | | | p Q4 vs |
|---|---|---|---|---|---|---|---|---|---|---|
| | n | % | n | % | n | % | n | % | p trend | Q1 |
| | 610 | | 610 | | 609 | | 610 | | | |
| Death | 23 | 5 | 16 | 3.5 | 15 | 3.1 | 32 | 6.3 | 0.1619 | 0.1678 |
| MI | 44 | 8.6 | 32 | 5.9 | 21 | 4.6 | 27 | 5.7 | 0.0162 | 0.059 |
| Ischemia -> Urgent Revasc | 40 | 7.7 | 40 | 8.8 | 30 | 5.6 | 36 | 6.1 | 0.4682 | 0.7325 |
| Death or MI | 56 | 10.9 | 45 | 8.7 | 35 | 7.5 | 55 | 11.1 | 0.7577 | 0.9498 |
| Death/MI/Ischemia -> Urgent Revasc | 93 | 17.7 | 85 | 17.4 | 64 | 12.9 | 88 | 16.6 | 0.439 | 0.853 |

With the exception of cause of death, percentages are kaplan-meier events rates with follow up censored at 10 months.
p values are from Cox regression analysis.

TABLE 12

Association between Baseline Marker Concentrations and 30 Day Outcomes
Troponin TIC Complex
Smoking: Never smoked

| | ≦16.65 | | 16.65-65.8 | | 65.8-195 | | >195 | | | p Q4 vs |
|---|---|---|---|---|---|---|---|---|---|---|
| | n | % | n | % | n | % | n | % | p trend | Q1 |
| | 220 | | 180 | | 193 | | 181 | | | |
| Death | 4 | 1.8 | 2 | 1.2 | 3 | 1.6 | 11 | 6.1 | 0.0178 | 0.0351 |
| MI | 9 | 4.1 | 7 | 4.1 | 4 | 2.1 | 6 | 3.5 | 0.4843 | 0.7361 |
| Ischemia -> Urgent Revasc | 1 | 0.5 | 7 | 4.1 | 7 | 3.7 | 11 | 6.2 | 0.0042 | 0.0111 |
| Death or MI | 11 | 5 | 8 | 4.6 | 6 | 3.1 | 16 | 8.9 | 0.1884 | 0.1254 |
| Death/MI/Ischemia -> Urgent Revasc | 12 | 5.5 | 15 | 8.7 | 13 | 6.8 | 26 | 14.5 | 0.0054 | 0.0029 |

Association of BNP with Baseline Clinical Variables

Data were evaluated from 2525 patients. Higher baseline quartile levels of BNP were associated with age, hypertension, and tobacco use. Higher quartile BNP levels were associated with history of congestive heart failure, renal function, electrocardiographic changes, Killip Class >I, and elevated levels of CK-MB. (Table 13) In contrast, the quartile BNP concentration was not associated with prior history of coronary artery disease, body mass index, and diabetes. There was a significant correlation between the concentration of BNP and the continuous baseline variables CRP (R=0.2; p<0.0001), fibrinogen (R=0.18; p<0.0001), LVEF (R=0.23, p<0.0001). The correlation between BNP concentration and body mass index was modest (R=0.06) (Table 14). In addition, higher mean BNP concentrations were significantly associated with the number of vessels with 50% stenosis or greater, lower ejection fraction, and positive stress test results (Table 15).

TABLE 13

Baseline Clinical Characteristics According to Quartiles of BNP (pg/mL)

|  | Quartile 1 | Quartile 2 | Quartile 3 | Quartile 4 | p trend | p Q4 vs Q1 |
|---|---|---|---|---|---|---|
| Range of BNP levels, pg/mL | 0-43.6 | 43.7-81.2 | 81.3-137.8 | 137.9-1456.6 | | |
| n | 631 | 632 | 632 | 630 | | |
| Time to randomization (hrs) | 39 ± 21 | 40 ± 21 | 41 ± 20 | 41 ± 19 | 0.04 | 0.10 |
| Age (years) | 57 ± 10 | 59 ± 11 | 61 ± 12 | 66 ± 11 | <0.0001 | <0.0001 |
| Male | 474 (75%) | 465 (74%) | 472 (75%) | 405 (64%) | 0.0001 | <0.0001 |
| White | 575 (91%) | 592 (94%) | 605 (96%) | 603 (96%) | 0.0002 | 0.001 |
| Past Medical History | | | | | | |
| Hypertension | 246 (39%) | 254 (40%) | 263 (42%) | 298 (47%) | 0.003 | 0.003 |
| Congestive Heart Failure | 26 (4%) | 28 (4%) | 26 (4%) | 56 (9%) | 0.0006 | 0.0008 |
| Coronary artery disease* | 329 (52%) | 312 (49%) | 294 (47%) | 327 (52%) | 0.7 | 0.9 |
| Peripheral vascular disease | 33 (5%) | 43 (7%) | 48 (8%) | 57 (9%) | 0.008 | 0.009 |
| Cerebrovascular disease | 24 (4%) | 32 (5%) | 39 (6%) | 60 (10%) | <0.0001 | 0.0001 |
| Diabetes | 138 (22%) | 133 (21%) | 132 (21%) | 152 (24%) | 0.4 | 0.3 |
| Family history of CAD | 268 (43%) | 260 (41%) | 253 (41%) | 232 (37%) | 0.045 | 0.04 |
| Hypercholesterolemia | 199 (32%) | 191 (30%) | 173 (28%) | 149 (24%) | 0.0009 | 0.002 |
| Smoking status: | | | | | 0.0002 | 0.001 |
| Current smoker | 233 (37%) | 263 (42%) | 236 (38%) | 189 (30%) | | |
| Never smoker | 193 (31%) | 161 (26%) | 185 (29%) | 254 (40%) | | |
| Past smoker | 204 (32%) | 205 (33%) | 209 (33%) | 186 (30%) | | |
| Index Diagnosis: | | | | | <0.0001 | <0.0001 |
| ST elevation MI | 141 (22%) | 189 (30%) | 231 (37%) | 264 (42%) | | |
| Non ST elevation MI | 87 (64%) | 137 (22%) | 159 (25%) | 182 (29%) | | |
| Unstable angina | 402 (64%) | 306 (48%) | 241 (38%) | 184 (29%) | | |
| Physical findings | | | | | | |
| BMI kg/m$^2$ | 29 ± 5 | 28 ± 5 | 28 ± 14 | 28 ± 12 | 0.1 | 0.08 |
| Systolic BP (mm Hg) | 130 ± 20 | 129 ± 19 | 128 ± 22 | 129 ± 21 | 0.3 | 0.4 |
| Killip Class II-IV | 31 (5%) | 36 (6%) | 56 (9%) | 109 (18%) | <0.0001 | <0.0001 |
| Diagnostic Testing | | | | | | |
| Creatinine clearance ≦90 | 146 (24%) | 185 (31%) | 229 (38%) | 350 (58%) | <0.0001 | <0.0001 |
| CK-MB > ULN | 212 (58%) | 308 (72%) | 349 (79%) | 388 (86%) | <0.0001 | <0.0001 |
| ST depression >0.5 mm | 270 (43%) | 297 (47%) | 311 (49%) | 356 (57%) | <0.0001 | <0.0001 |
| T wave inversion >3 mm | 137 (22%) | 146 (23%) | 171 (27%) | 167 (27%) | 0.02 | 0.047 |

*Prior coronary artery disease: previous MI, documented unstable angina, angina pectoris, angiographically confirmed CAD, prior PTCR or CABG not for index event.

TABLE 14

Correlation between BNP Levels & Continuous Baseline Variables

| | R value | p value |
|---|---|---|
| Age (years) | 0.28 | <0.0001 |
| BMI | 0.06 | 0.006 |
| Maximum recorded CK-MB (% of ULN) | 0.09 | 0.0005 |
| CRP (mg/dl) | 0.2 | <0.0001 |
| Fibrinogen (mg · dl) | 0.18 | <0.0001 |
| LVEF (%) | 0.23 | <0.0001 |
| Creatinine clearance | 0.28 | <0.0001 |

TABLE 15

Association between cardiac test results and BNP concentration

| Test | Result | n | BNP (Mean ± SD) | p value |
|---|---|---|---|---|
| Coronary Angiography: | None | 27 | 68 ± 48 | <0.0001 |
| No. vessels with ≧50% stenosis | 1 | 220 | 83 ± 65 | |
| | 2 | 106 | 98 ± 98 | |
| | ≧3 | 79 | 143 ± 145 | |
| LV Ejection Fraction | ≦50% | 156 | 136 ± 161 | 0.003 |
| | >50% | 189 | 96 ± 78 | |
| Stress test | Positive | 296 | 118 ± 118 | 0.003 |
| | Indeterminate | 118 | 118 ± 128 | |
| | Negative | 374 | 91 ± 95 | |

Association of BNP with Clinical Outcomes

The concentration of BNP was significantly higher among patients who died by 30 days (p<0.0001) and 10 months (p<0.0001) vs. those who were alive at the same time points (Table 16). Furthermore, the BNP concentration was significantly higher among patients who experienced a non-fatal MI by 30 days (p=0.01) and 10 months (p=0.02) vs. those who did not (Table 16). The relationship between higher BNP concentration and death by 30 days and 10 months also was observed in an analysis of subgroups based on index diagnosis (Table 17).

TABLE 16

Association between baseline BNP concentration (pg/mL) and outcomes

| Outcome | n | Median [25, 75] | Mean ± SD | p value |
|---|---|---|---|---|
| 30 days | | | | |
| Dead | 39 | 153 [79, 294] | 226 ± 204 | <0.0001 |
| Alive | 2486 | 80 [43, 135] | 113 ± 124 | |
| MI | 70 | 109 [50, 159] | 152 ± 159 | 0.01 |
| No MI | 2455 | 80 [44, 137] | 113 ± 125 | |
| 10 months | | | | |
| Dead | 85 | 143 [88, 308] | 228 ± 228 | <0.0001 |
| Alive | 2440 | 79 [43, 133] | 110 ± 120 | |
| MI | 124 | 101 [50, 161] | 141 ± 140 | 0.02 |
| No MI | 2401 | 80 [43, 134] | 113 ± 126 | |

TABLE 17

Association between baseline BNP concentration (pg/ml) and 10-month outcomes in subgroups based on index diagnosis.

| Outcome | n | Median [25, 75] | Mean ± SD | p value |
|---|---|---|---|---|
| ST elevation MI | 825 | 96 [56, 161] | 131± | |
| Dead by 30 days | 13 | 153 [77, 265] | 236 ± 220 | 0.002 |
| Alive at 30 days | 812 | 95 [56, 161] | | |
| Dead by 10 months | 23 | 150 [90, 227] | 199 ± 176 | 0.008 |
| Alive at 10 months | 802 | 95 [55, 161] | 129 ± 123 | |
| Non-ST elevation ACS | 1698 | 72 [39, 124] | 106± | |
| Dead by 30 days | 26 | 149 [84, 307] | 220 ± 200 | <0.0001 |
| Alive at 30 days | 1672 | 71 [39, 123] | 105 ± 124 | |
| Dead by 30 days | 62 | 142 [88, 320] | 239 ± 245 | <0.0001 |
| Alive at 30 days | 1636 | 70 [38, 121] | 101 ± 117 | |
| Unstable Angina | 1133 | 60 [33, 105] | 92± | |
| Dead by 30 days | 14 | 94 [69, 237] | 182 ± 195 | 0.002 |
| Alive at 30 days | 1119 | 60 [33, 105] | 90 ± 109 | |
| Dead by 10 months | 34 | 96 [70, 265] | 233 ± 292 | <0.0001 |
| Alive at 10 months | 1099 | 58 [33, 104] | 87 ± 97 | |

Association of FABP with Baseline Clinical Variables

Data were evaluated from 2287 patients. The association of FABP with baseline clinical variables was performed using a FABP cutpoint of 8 ng/mL. Higher baseline levels of FABP were associated with age, history of congestive heart failure, renal function, electrocardiographic changes, Killip Class >I, and elevated levels of CK-MB, cTnI, BNP, and CRP (Table 18). In contrast, the quartile FABP concentration was not associated with prior history of coronary artery disease, body mass index, hypertension, and diabetes. There was a significant correlation between the concentration of FABP and the cTnI concentration (R=0.21; p<0.0001). The correlations between FABP concentration and other continuous variables were modest ($R^2<0.03$) (Table 19).

TABLE 18

Baseline Clinical Characteristics According to Baseline FABP (ng/mL)

| | FABP <=8 | FABP >8 | p |
|---|---|---|---|
| Range, ng/mL | <8 | 8-434.2 | |
| n | 1955 | 332 | |
| Time to randomization (hrs) | 42 ± 19 | 33 ± 19 | <0.0001 |
| Age (years) | 60 ± 11 | 65 ± 12 | <0.0001 |
| Male | 1401 (72%) | 244 (73%) | 0.5 |
| White | 1833 (94%) | 315 (95%) | 0.4 |
| Past Medical History | | | |
| Hypertension | 820 (42%) | 140 (42%) | 1.0 |
| Congestive Heart Failure | 89 (5%) | 29 (9%) | 0.001 |

TABLE 18-continued

Baseline Clinical Characteristics According to Baseline FABP (ng/mL)

| | FABP <=8 | FABP >8 | p |
|---|---|---|---|
| Coronary artery disease* | 983 (50%) | 155 (47%) | 0.2 |
| PCI for index event | 670 (34%) | 105 (32%) | 0.3 |
| Peripheral vascular disease | 132 (7%) | 24 (7%) | 0.8 |
| Cerebrovascular disease | 57 (3%) | 10 (3%) | 0.9 |
| Diabetes | 428 (22%) | 65 (20%) | 0.3 |
| Family history of CAD | 793 (41%) | 111 (34%) | 0.02 |
| Hypercholesterolemia | 576 (30%) | 72 (22%) | 0.003 |
| ASA in 2 wks prior | 799 (41%) | 120 (36%) | 0.1 |
| Lipid rx 2 wk prior | 426 (22%) | 53 (16%) | 0.01 |
| Heparin prior to rand | 1734 (89%) | 278 (84%) | 0.009 |
| ACE management | 1577 (81%) | 248 (75%) | 0.01 |
| B-blocker prior | 538 (28%) | 86 (26%) | 0.5 |
| Smoking status: | | | 0.08 |
| Current smoker | 37% | 31% | |
| Never smoker | 31% | 36% | |
| Past smoker | 32% | 33% | |
| Index Diagnosis: | | | <0.001 |
| ST elevation MI | 29% | 52% | |
| Non ST elevation MI | 22% | 24% | |
| Unstable angina | 49% | 24% | |
| Physical findings | | | |
| BMI kg/m$^2$ | 28 ± 11 | 28 ± 5 | 0.4 |
| Systolic BP (mm Hg) | 129 ± 21 | 130 ± 22 | 0.2 |
| HR (BPM) | 72 ± 14 | 74 ± 16 | 0.03 |
| Killip Class II-IV | 150 (8%) | 56 (17%) | <0.001 |
| Diagnostic Testing | | | |
| Creatinine clearance ≦90 | 679 (36%) | 167 (53%) | <0.001 |
| ClCr (cc/min) | 106 ± 40 | 92 ± 40 | <0.0001 |
| CK-MB > ULN | 909 (71%) | 240 (91%) | <0.001 |
| CTnI >1.5 ng/ml | 232 (22%) | 194 (59%) | <0.001 |
| BNP >80 pg/ml | 908 (47%) | 240 (73%) | <0.001 |
| CRP >1.5 ng/ml | 262 (40%) | 79 (50%) | 0.03 |
| ST deviation >1 mm | 857 (44%) | 212 (64%) | <0.001 |
| T wave inversion >3 mm | 278 (24%) | 82 (25%) | 0.9 |
| Extent CAD (50% stenosis) | | | 0.3 |
| 0 vessel | 7% | 4% | |
| 1 vessel | 33% | 35% | |
| 2 vessel | 28% | 30% | |
| 3 vessel | 32% | 32% | |
| Pos ETT | 245 (37%) | 32 (37%) | 0.2 |
| EF (%) | 55 ± 12 | 49 ± 13 | <0.0001 |

TABLE 19

Correlation between FABP and Continuous variables

| Variable | R$^2$ | P value |
|---|---|---|
| Time CP to randomization | 0.02 | <0.0001 |
| Age | 0.007 | 0.0001 |
| BMI | 0.0006 | 0.25 |
| CKMB peak | 0.024 | <0.0001 |
| BIOSITE cTnI | 0.21 | <0.0001 |
| CRP | 0.0001 | 0.75 |
| Fibrinogen | 0.003 | 0.002 |
| BNP | 0.006 | 0.0002 |
| Creatinine Clearance | 0.008 | 0.008 |
| LVEF | 0.02 | <0.0001 |

Association of FABP with Clinical Outcomes

The mean concentration of FABP was significantly higher among patients who died by 30 days (p<0.0001) and 10 months (p<0.0001) vs. those who were alive at the same time points (Table 20). The mean FABP concentration was significantly higher among patients with the combined endpoints of death, non-fatal MI, or urgent revascularization by 30 days (p<0.0001) and 10 months (p<0.0001) vs. those who did not have these endpoints (Table 20). Furthermore, the mean FABP concentration was significantly higher among patients who had CHF by 30 days (p<0.0001) and 10 months (p<0.0001) vs. those who did not (Table 20). These relationships maintained statistical significance when the FABP concentration was classified either as positive (FABP>8) or negative (FABP=8 or less) (Table 21).

TABLE 20

Association between baseline FABP concentration (ng/mL) and outcomes

| Outcome | n | Mean ± SD | p value* |
|---|---|---|---|
| 30 days | | | |
| Dead | 33 | 22.8 ± 27.5 | |
| Alive | 2254 | 10.5 ± 14.7 | <0.0001 |
| Death or MI | 86 | 17.2 ± 22.0 | <0.0001 |
| No Death or MI | 2201 | 10.4 ± 14.6 | |
| D/MI/UR | 157 | 16.2 ± 37.6 | <0.0001 |
| No D/MI/UR | 2130 | 10.3 ± 11.7 | |
| CHF | 46 | 20.2 ± 21.0 | <0.0001 |
| No CHF | 2241 | 10.5 ± 14.8 | |
| 10 months | | | |
| Dead | 76 | 18.3 ± 22.7 | <0.0001 |
| Alive | 2211 | 10.5 ± 14.6 | |
| Death or MI | 169 | 14.5 ± 18.3 | <0.0001 |
| No Death or MI | 2118 | 10.4 ± 14.7 | |
| D/MI/UR | 294 | 13.7 ± 28.5 | <0.0001 |
| No D/MI/UR | 1993 | 10.3 ± 11.7 | |
| CHF | 66 | 17.5 ± 18.5 | <0.0001 |
| No CHF | 2221 | 10.5 ± 14.8 | |

*Wicoxon rank sum test

TABLE 21

Association between baseline FABP and outcomes

| Outcome | FABP Neg | FABP Pos | P value |
|---|---|---|---|
| n | 1955 | 332 | |
| 30 day | | | |
| Death | 19 (1.0%) | 14 (4.2%) | <0.001 |
| MI | 45 (2.3%) | 14 (4.2%) | 0.04 |
| UR | 58 (3.0%) | 16 (4.8%) | 0.08 |
| D/MI | 59 (3.0%) | 27 (8.1%) | <0.001 |
| D/MI/UR | 116 (5.9%) | 41 (12.4%) | <0.001 |
| CHF | 24 (1.2%) | 22 (6.3%) | <0.001 |
| 10 month (estimates) | | | |
| Death | 46 (3.1%) | 30 (12.4%) | <0.0001 |
| MI | 88 (5.6%) | 22 (9.4%) | 0.05 |
| UR | 109 (6.4%) | 22 (7.4%) | 0.34 |
| D/MI | 120 (7.8%) | 49 (21.4%) | <0.0001 |
| D/MI/UR | 226 (14.4%) | 68 (29.0%) | <0.0001 |
| CHF | 30 (2.0%) | 21 (8.1%) | <0.0001 |
| D/MI/CHF | 140 (9.3%) | 56 (23.5%) | <0.0001 |

Association of TpP with Baseline Clinical Variables

Data were evaluated from 2349 patients. Higher baseline levels of TpP were associated with age, history of coronary artery disease, renal function, history of CHF, aspirin use, and inversely associated with Caucasian race, and heparin therapy (Table 22). In contrast, the TpP concentration was not associated with heart rate, Killip Class >I, body mass index, hypertension, the extent of coronary artery disease, and diabetes.

TABLE 22

Baseline Clinical Characteristics According to Quartiles of TpP in OPUS-TIMI 16

| Endpoints | TpP Quartile | | | | p value |
| | 1st | 2nd | 3rd | 4th | global $\chi^2$ |
|---|---|---|---|---|---|
| Range | 0-4.8 | 4.9-8.9 | 9-15.9 | 16-160 | |
| N | 596 | 590 | 577 | 586 | |
| Time to randomization | 39 | 41 | 43 | 40 | 0.07 |
| Demographics | | | | | |
| Age (yrs) | 59 | 60 | 62 | 62 | 0.002 |
| Male | 76% | 70% | 71% | 69% | 0.01 |
| White | 94% | 93% | 96% | 93% | 0.1 |
| PMH | | | | | |
| Hypertension | 37% | 43% | 44% | 43% | 0.076 |
| Diabetes | 18% | 22% | 22% | 24% | 0.06 |
| Current smoker | 39% | 38% | 35% | 34% | |
| Hyperlipidemia | 25% | 30% | 28% | 31% | 0.1 |
| FHx | 39% | 40% | 39% | 42% | 0.69 |
| Prior CAD | 41% | 49% | 53% | 56% | <0.001 |
| Prior MI | | | | | |
| Prior CHF | 2.0% | 5.7% | 5.6% | 7.5% | <0.001 |
| Index Diagnosis | | | | | |
| STEMI | 44% | 28% | 30% | 29% | |
| NSTEMI | 23% | 24% | 24% | 19% | |
| UA | 33% | 48% | 47% | 52% | |
| Meds prior to random. | | | | | |
| ASA | 33% | 39% | 43% | 46% | <0.001 |
| Heparin | 93% | 88% | 88% | 83% | <0.001 |
| Physical Findings | | | | | |
| BMI (kg/m$^2$) | 27 | 29 | 28 | 29 | 0.19 |
| SBP (mm Hg) | 127 | 129 | 130 | 129 | 0.16 |
| HR (bpm) | 72 | 73 | 72 | 73 | 0.3 |
| Killip Class II-IV | 7.5% | 8.3% | 8.6% | 11.2% | 0.14 |
| Diagnostic Testing | | | | | |
| CrCl ≦90 ml/min | 35% | 37% | 44% | 40% | 0.02 |
| TnI >1.5 ng/mL | 36% | 25% | 26% | 23% | <0.001 |
| CRP >1.5 mg/dL | 42% | 46% | 38% | 46% | 0.24 |
| BNP >80 pg/mL | 52% | 49% | 56% | 46% | 0.01 |
| ST deviation >1 mm | 49% | 45% | 47% | 46% | 0.47 |
| Extent of CAD | | | | | |
| 0 VD | 7% | 8% | 5% | 7% | |
| 1 VD | 39% | 27% | 39% | 33% | |
| 2 VD | 30% | 30% | 24% | 28% | |
| 3 VD | 23% | 35% | 32% | 32% | |

Association of TpP with Clinical Outcomes

The TpP concentration was significantly higher among patients who died by 10 months (p<0.05) vs. those who were alive at the same time points (Table 23). The TpP concentration was significantly higher among patients who experienced ischemia requiring hospitalization by 10 months (p=0.0062) vs. those who did not (Table 23). The TpP concentration was significantly higher among patients with the combined endpoints of death or non-fatal MI, as well as death, non-fatal MI, or urgent revascularization by 10 months (p<0.02) vs. those who did not experience these endpoints (Table 23).

TABLE 23

Rates of Death, MI, CHF, Urgent Revasc, and Ischemia in OPUS-TIMI 16

| Endpoints | TpP Quartile | | | | p value $\chi^2$ for trend |
|---|---|---|---|---|---|
| | 1st | 2nd | 3rd | 4th | |
| Range | 0-4.8 | 4.9-8.9 | 9-15.9 | 16-160 | |
| N | 596 | 590 | 577 | 586 | |
| 10-Month Outcomes | | | | | |
| Death | 2.68 | 2.37 | 3.64 | 4.44 | 0.047 |
| MI | 4.03 | 4.75 | 5.03 | 5.46 | 0.24 |
| CHF | 2.35 | 2.37 | 3.64 | 2.90 | 0.34 |
| Urg Revasc | 4.53 | 5.08 | 7.45 | 6.31 | 0.074 |
| Ischemia → Rehosp | 4.70 | 5.93 | 8.67 | 8.02 | 0.0062 |

TABLE 23-continued

Rates of Death, MI, CHF, Urgent Revasc, and Ischemia in OPUS-TIMI 16

| Endpoints | TpP Quartile | | | | p value $\chi^2$ for trend |
|---|---|---|---|---|---|
| | 1st | 2nd | 3rd | 4th | |
| D/MI | 5.87 | 6.44 | 7.97 | 9.22 | 0.016 |
| D/MI/CHF | 7.38 | 7.97 | 9.36 | 10.24 | 0.055 |
| D/MI/UR | 10.40 | 11.36 | 14.90 | 15.19 | 0.0038 |

Association of MCP-1 with Baseline Clinical Variables

Data were evaluated from 2270 patients. Higher baseline levels of MCP-1 were associated with age, history of coronary artery disease, renal function, history of CHF, diabetes, hypertension, Killip Class >I, and aspirin use (Table 24). In contrast, the MCP-1 concentration was not associated with heart rate, body mass index, the extent of coronary artery disease, and smoking.

TABLE 24

Baseline Clinical Characteristics According to Quartiles of MCP-1 (ng/mL)

| | Quartile 1 | Quartile 2 | Quartile 3 | Quartile 4 | p trend | p Q4 vs Q1 |
|---|---|---|---|---|---|---|
| Range, ng/mL | 40-127.9 | 128.1-177.3 | 177.4-238 | 238.5-7016.3 | | |
| n | 567 | 568 | 568 | 567 | | |
| Time to randomization (hrs) | 41 ± 20 | 40 ± 19 | 42 ± 20 | 40 ± 20 | 0.45 | 0.54 |
| Age (years) | 57 ± 11 | 59 ± 12 | 62 ± 11 | 65 ± 11 | <0.0001 | <0.0001 |
| Male | 433 (76%) | 414 (73%) | 406 (72%) | 375 (66%) | 0.0001 | <0.0001 |
| White | 531 (94%) | 532 (94%) | 539 (95%) | 533 (94%) | 0.61 | 0.81 |
| Past Medical History | | | | | | |
| Hypertension | 224 (40%) | 223 (39%) | 238 (42%) | 276 (49%) | 0.001 | 0.002 |
| Congestive Heart Failure | 18 (3%) | 25 (4%) | 26 (5%) | 45 (8%) | 0.0004 | <0.0001 |
| Coronary artery disease* | 245 (43%) | 274 (48%) | 291 (51%) | 318 (56%) | <0.0001 | <0.0001 |
| PCI for index event | 201 (35%) | 186 (33%) | 186 (33%) | 199 (35%) | 0.91 | 0.90 |
| Peripheral vascular disease | 32 (6%) | 32 (6%) | 43 (8%) | 47 (8%) | 0.04 | 0.08 |
| Cerebrovascular disease | 15 (3%) | 18 (3%) | 16 (3%) | 19 (3%) | 0.58 | 0.49 |
| Diabetes | 115 (20%) | 105 (19%) | 124 (22%) | 145 (26%) | 0.01 | 0.03 |
| Family history of CAD | 242 (43%) | 231 (41%) | 214 (38%) | 211 (38%) | 0.21 | 0.08 |
| Hypercholesterolemia | 161 (28%) | 167 (29%) | 163 (29%) | 168 (26%) | 0.39 | 0.41 |
| ASA in 2 wks prior | 203 (36%) | 230 (40%) | 228 (40%) | 252 (45%) | 0.004 | 0.002 |
| Lipid rx 2 wk prior | 121 (21%) | 122 (22%) | 115 (20%) | 116 (21%) | 0.65 | 0.76 |
| Heparin prior to rand | 508 (90%) | 495 (87%) | 489 (86%) | 506 (89%) | 0.75 | 0.85 |
| Smoking status: | | | | | 0.24 | 0.06 |
| Current smoker | 215 (38%) | 216 (38%) | 204 (36%) | 177 (31%) | | |
| Never smoker | 178 (31%) | 175 (31%) | 176 (31%) | 196 (35%) | | |
| Past smoker | 173 (31%) | 175 (31%) | 188 (33%) | 192 (34%) | | |
| Index Diagnosis: | | | | | 0.01 | 0.02 |
| ST elevation MI | 176 (31%) | 187 (33%) | 178 (31%) | 196 (35%) | | |
| Non ST elevation MI | 160 (28%) | 111 (20%) | 120 (21%) | 120 (21%) | | |
| Unstable angina | 231 (41%) | 269 (47%) | 270 (48%) | 251 (44%) | | |
| Physical findings | | | | | | |
| BMI kg/m$^2$ | 28 ± 6 | 28 ± 4 | 29 ± 15 | 29 ± 13 | 0.28 | 0.96 |
| Systolic BP (mm Hg) | 127 ± 19 | 129 ± 20 | 129 ± 22 | 130 ± 22 | 0.04 | 0.004 |
| HR (BPM) | 72 ± 14 | 72 ± 13 | 73 ± 14 | 73 ± 15 | 0.66 | 0.26 |
| Killip Class II-IV | 46 (8%) | 37 (7%) | 46 (8%) | 69 (12%) | 0.02 | 0.003 |
| Diagnostic Testing | | | | | | |
| Creatinine clearance ≦90 | 143 (26%) | 191 (35%) | 229 (42%) | 280 (52%) | <0.0001 | <0.0001 |
| ClCr (cc/min) | 116 ± 42 | 107 ± 40 | 103 ± 41 | 93 ± 37 | <0.0001 | <0.0001 |
| CK-MB > ULN | 300 (79%) | 280 (72%) | 278 (72%) | 284 (75%) | 0.25 | 0.21 |
| CTnI >1.5 ng/ml | 176 (31%) | 156 (28%) | 138 (25%) | 149 (27%) | 0.04 | 0.08 |
| BNP >80 pg/ml | 265 (47%) | 260 (47%) | 276 (49%) | 334 (59%) | <0.0001 | <0.0001 |

TABLE 24-continued

Baseline Clinical Characteristics According to Quartiles of MCP-1 (ng/mL)

| | Quartile 1 | Quartile 2 | Quartile 3 | Quartile 4 | p trend | p Q4 vs Q1 |
|---|---|---|---|---|---|---|
| CRP >1.5 ng/ml | 83 (43%) | 83 (42%) | 89 (42%) | 94 (47%) | 0.51 | 0.51 |
| ST deviation >1 mm | 239 (42%) | 267 (47%) | 267 (47%) | 289 (51%) | 0.005 | 0.003 |
| Extent CAD (50% stenosis) | | | | | 0.49 | 0.07 |
| 0 vessel | 26 (8%) | 20 (7%) | 19 (7%) | 18 (6%) | | |
| 1 vessel | 120 (38%) | 91 (32%) | 90 (32%) | 90 (30%) | | |
| 2 vessel | 80 (26%) | 84 (30%) | 78 (28%) | 87 (29%) | | |
| 3 vessel | 86 (28%) | 84 (30%) | 82 (33%) | 102 (34%) | | |
| Pos ETT | 96 (46%) | 95 (54%) | 87 (44%) | 65 (44%) | 0.45 | 0.75 |
| EF (%) | 55 ± 13 | 54 ± 13 | 53 ± 13 | 53 ± 14 | 0.11 | 0.06 |

Association of MCP-1 with Clinical Outcomes

The mean MCP-1 concentration was significantly higher among patients who experienced a non-fatal MI by 30 days (p=0.01) or by 10 months (p=0.04) vs. those who did not at the same time points (Table 25). In addition, the mean MCP-1 concentration was significantly higher among patients with the combined endpoints of death, or non-fatal MI (p=0.05), as well as death, non-fatal MI, or CHF by 10 months (p=0.02) vs. those who did not experience these endpoints (Table 25). These findings also were observed in a analysis of quartile MCP-1 concentration and outcome (Table 26).

TABLE 25

Association between baseline MCP-1 concentration (ng/mL) and outcomes

| Outcome | n | Median [25, 75] | Mean ± SD | p value* |
|---|---|---|---|---|
| 30 days | | | | |
| Dead | 34 | 147 [116, 227] | 184 ± 117 | 0.19 |
| Alive | 2236 | 178 [128, 239] | 206 ± 212 | |
| MI | 59 | 209 [146, 279] | 235 ± 130 | 0.01 |
| No MI | 2211 | 177 [128, 237] | 205 ± 213 | |
| Death or MI | 88 | 197 [135, 268] | 221 ± 129 | 0.13 |
| No Death or MI | 2182 | 177 [128, 236] | 205 ± 213 | |

TABLE 25-continued

Association between baseline MCP-1 concentration (ng/mL) and outcomes

| Outcome | n | Median [25, 75] | Mean ± SD | p value* |
|---|---|---|---|---|
| D/MI/UR | 153 | 185 [140, 251] | 229 ± 284 | 0.12 |
| No D/MI/UR | 2117 | 177 [127, 237] | 204 ± 205 | |
| CHF | 44 | 182 [134, 236] | 260 ± 468 | 0.79 |
| No CHF | 2226 | 177 [128, 238] | 204 ± 203 | |
| D/MI/CHF | 114 | 197 [136, 264] | 243 ± 308 | 0.06 |
| No D/MI/CHF | 2156 | 177 [128, 236] | 203 ± 204 | |
| 10 months | | | | |
| Dead | 78 | 181 [136, 248] | 205 ± 213 | 0.41 |
| Alive | 2192 | 177 [128, 237] | 208 ± 110 | |
| MI | 110 | 202 [136, 268] | 221 ± 122 | 0.04 |
| No MI | 2160 | 177 [128, 236] | 205 ± 214 | |
| Death or MI | 172 | 192 [134, 265] | 216 ± 120 | 0.05 |
| No Death or MI | 2098 | 177 [128, 235] | 205 ± 216 | |
| D/MI/UR | 293 | 180 [133, 253] | 217 ± 225 | 0.23 |
| No D/MI/UR | 1977 | 177 [127, 235] | 204 ± 209 | |
| CHF | 65 | 192 [147, 242] | 246 ± 387 | 0.25 |
| No CHF | 2205 | 177 [128, 239] | 204 ± 203 | |
| D/MI/CHF | 203 | 196 [136, 264] | 229 ± 242 | 0.02 |
| No D/MI/CHF | 2067 | 176 [127, 235] | 203 ± 207 | |

*Wicoxon rank sum test

TABLE 26

Association between baseline MCP-1 quartiles and outcomes

| Outcome | Quartile 1 | Quartile 2 | Quartile 3 | Quartile 4 | P trend | P Q4 vs Q1 |
|---|---|---|---|---|---|---|
| Range, ng/mL | 40-127.9 | 128.1-177.3 | 177.4-238 | >238 | | |
| n | 567 | 568 | 568 | 567 | | |
| 30 day | | | | | | |
| Death | 10 (1.8%) | 12 (2.1%) | 5 (0.9%) | 7 (1.2%) | 0.22 | 0.46 |
| MI | 10 (1.8%) | 14 (2.5%) | 11 (1.9%) | 24 (4.2%) | 0.02 | 0.02 |
| UR | 8 (1.4%) | 24 (4.2%) | 19 (3.3%) | 17 (3.0%) | 0.23 | 0.07 |
| D/MI | 19 (3.4%) | 22 (3.9%) | 16 (2.8%) | 31 (5.5%) | 0.14 | 0.08 |
| D/MI/UR | 27 (4.8%) | 46 (8.1%) | 35 (6.2%) | 45 (7.9%) | 0.11 | 0.03 |
| CHF | 9 (1.6%) | 12 (2.1%) | 12 (2.1%) | 11 (1.9%) | 0.68 | 0.65 |
| D/MI/CHF | 23 (4.1%) | 27 (4.8%) | 25 (4.4%) | 39 (6.9%) | 0.048 | 0.04 |
| 10 month estimates | | | | | | |
| Death | 14 (2.7%) | 24 (5.2%) | 15 (3.1%) | 25 (7.0%) | 0.21 | 0.07 |
| MI | 23 (4.8%) | 24 (5.2%) | 23 (5.1%) | 40 (9.8%) | 0.03 | 0.03 |
| UR | 25 (5.3%) | 43 (8.3%) | 28 (6.0%) | 31 (6.2%) | 0.89 | 0.42 |
| D/MI | 36 (7.4%) | 42 (9.4%) | 33 (7.0%) | 61 (15.6%) | 0.02 | 0.008 |
| D/MI/UR | 61 (13.0%) | 84 (18.2%) | 60 (12.9%) | 88 (21.7%) | 0.11 | 0.02 |

TABLE 26-continued

Association between baseline MCP-1 quartiles and outcomes

| Outcome | Quartile 1 | Quartile 2 | Quartile 3 | Quartile 4 | P trend | P Q4 vs Q1 |
|---|---|---|---|---|---|---|
| CHF | 11 (2.2%) | 9 (1.9%) | 15 (3.9%) | 16 (3.4%) | 0.17 | 0.33 |
| D/MI/CHF | 41 (8.4%) | 46 (10.1%) | 43 (10.1%) | 68 (17.2%) | 0.009 | 0.007 |

In a multivariate model (n=2068) adjusting for other independent predictors of long-term mortality, including age, diabetes, renal function, evidence of CHF, ECG changes, and levels of cTnI and BNP, increasing concentration of MMP-9 remained associated with higher 10-month mortality. The adjusted odds ratios for death at 10 months for patients in the second, third, and fourth quartiles of MMP-9 were 4.5 (1.3-15.6), 6.4 (1.9-21.4), and 7.6 (2.3-25.5). When the model was repeated in 736 patients with complete data for all variables including CRP, MMP-9 remained significantly associated with 10-month mortality. The adjusted odds ratios were 3.1 (0.9-10.7), 3.9 (1.1-13.1), and 4.2 (1.3-14.4) in the second, third, and fourth quartiles.

TABLE 27

Multivariate models for 10-month mortality

| | Model 1 (n = 2068) | | Model 2 (n = 736) | |
|---|---|---|---|---|
| Variable | HR | 95% CI | HR | 95% CI |
| Age >75 | 2.25 | 1.03-4.92 | 1.91 | 0.83-4.40 |
| Diabetes | 1.59 | 0.69-2.43 | 1.30 | 0.73-2.31 |
| Killip class >1 | 2.98 | 1.71-5.21 | 2.37 | 1.27-4.45 |
| Left bundle branch block | 4.96 | 2.21-11.12 | 5.32 | 2.19-12.90 |
| Creatinine clearance <90 cc/min | 1.28 | 0.67-2.48 | 1.61 | 0.81-3.23 |
| cTnI >1.5 ng/mL | 2.12 | 1.15-3.93 | 2.54 | 1.29-5.02 |
| BNP >40 pg/mL | 5.70 | 1.35-24.04 | 5.58 | 1.29-24.15 |
| CRP >1.5 ng/mL | — | — | 2.18 | 1.22-3.90 |
| MMP-9 Quartile 1 (reference quartile) | 1.0 | — | 1.0 | — |
| MMP-9 Quartile 2 | 4.47 | 1.28-15.57 | 3.05 | 0.87-10.76 |
| MMP-9 Quartile 3 | 6.39 | 1.90-21.42 | 3.89 | 1.15-13.15 |
| MMP-9 Quartile 4 | 7.64 | 2.29-25.51 | 4.25 | 1.25-14.42 |

Model 1 includes patients with complete data for all variables except C reactive protein. Model 2 includes patients with complete data for all variables including C reactive protein. In addition to the variables listed, the models were adjusted for prior evidence of hypercholesterolemia, congestive heart failure, or peripheral arterial disease; prior use of heparin, nitrates, or diuretics; index diagnosis (unstable angina, non-ST elevation MI, ST elevation MI); use of nitrates or ace inhibitors for management of the index event; heart rate; blood pressure; and ST changes on the electrocardiogram.

The plasma concentration of MMP-9, measured within the first few days after presentation with an acute coronary syndrome, is predictive of the risk for mortality, nonfatal MI, and congestive heart failure. The association between MMP-9 and mortality is independent of baseline clinical variables, ECG findings, and levels of established cardiac biomarkers such as troponin I, C-reactive protein, and B-type natriuretic peptide. In multivariate analyses, elevated levels of matrix metalloproteinase-9, C-reactive protein, B-type natriuretic peptide, and troponin I were each significant independent predictors of increased 10-month mortality.

In a prior study, MMP-9 levels did not increase following exercise in patients with stable angina, despite symptomatic and electrocardiographic evidence of ischemia. Kai H et al., *Peripheral blood levels of matrix metalloproteases-2 and -9 are elevated in patients with acute coronary syndrome*, J Am Coll Cardiol 32:368-372 (1998). In the present study, no association between MMP-9 and the extent of atherosclerosis, and generally poor correlations between MMP-9 and markers of cardiac necrosis, such as CKMB and cTnI were observed. The relationship between MMP-9 and outcomes was similar between patients with unstable angina and those with myocardial infarction.

The present example demonstrates the clinical utility of the association between elevations in individual markers and outcome. Furthermore, there is a demonstrated benefit of using a multimarker strategy that incorporates different independent markers related to unique pathological processes for risk stratification. The markers chosen in this example are representative of myocardial damage (cTnI, cTnTIC, and FABP), ventricular dysfunction (BNP), matrix degradation or plaque rupture (MMP-9), inflammation (MCP-1 and CRP), and coagulation activation (TpP). One who is skilled in the art is aware that these pathological processes are independently associated with the adverse events described in this example. In this regard, alternative markers of each these various pathological processes may be substituted for the markers in this example for risk stratification of ACS patients. Furthermore, various combinations of markers for the various pathological processes may be useful in risk stratification of patients with ACS.

Example 5

Diagnostic Utility

MMP-9 is elevated in all levels of acute coronary systems, from unstable angina through ST-segment elevation myocardial infarction (STEMI). The TIMI OPUS-16 study population could be segregated into three groups, unstable angina (UA), non-ST-segment elevation myocardial infarction (NSTEMI), and STEMI. Of particular interest is the level of sensitivity (97.8-100%) at a specificity of 95% in the discrimination of unstable angina from normal healthy donors (Table 28). The most widely accepted marker of cardiac damage, TnI only achieves slightly over 50% sensitivity in this subset of acute coronary syndromes.

TABLE 28

Sensitivity and specificity of markers in patients with unstable angina

| Time from Sympton Onset | Specificity | BNP | FABP | MCP-1 | MMP-9 | TpP | cTnTIC | cTnI |
|---|---|---|---|---|---|---|---|---|
| 0-3 hr | 94.8% | 60.9% | 5.3% | 10.5% | 100.0% | 45.0% | 0.0% | 43.8% |
| 0-6 hr | 94.8% | 65.5% | 9.1% | 13.3% | 100.0% | 50.0% | 10.5% | 33.0% |
| 0-12 hr | 94.8% | 69.7% | 9.0% | 13.7% | 98.0% | 53.4% | 18.0% | 53.2% |
| 0-24 hr | 94.8% | 34.8% | 7.5% | 83.5% | 97.8% | 56.0% | 17.7% | 54.9% |

In individuals with either NSTEMI or STEMI, TnI has excellent sensitivity and specificity, particularly between 6 h and 24 h from the time of symptom onset (Tables 29 and 30). The fact that MMP-9 is elevated in unstable angina while TnI may be only slightly elevated provides a useful means of discriminating between the less serious unstable angina and the more serious myocardial infarction. Therapeutic options could be influenced if the physician had this information available.

TABLE 29

Sensitivity and specificity of markers in patients with NSTEMI

| Time from Sympton Onset | Specificity | BNP | FABP | MCP-1 | MMP-9 | TpP | cTnTIC | cTnI |
|---|---|---|---|---|---|---|---|---|
| 0-3 hr | 94.8% | 100.0% | 0.0% | 25.0% | 100.0% | 50.0% | 25.0% | 75.0% |
| 0-6 hr | 94.8% | 75.0% | 14.3% | 14.3% | 100.0% | 28.6% | 42.9% | 71.4% |
| 0-12 hr | 94.8% | 64.4% | 23.1% | 15.4% | 100.0% | 42.9% | 50.0% | 83.3% |
| 0-24 hr | 94.8% | 76.7% | 24.6% | 20.6% | 98.5% | 50.0% | 62.9% | 91.2% |

TABLE 30

Sensitivity and specificity of markers in patients with STEMI

| Time from Sympton Onset | Specificity | BNP | FABP | MCP-1 | MMP-9 | TpP | cTnTIC | cTnI |
|---|---|---|---|---|---|---|---|---|
| 0-3 hr | 94.8% | 83.3% | 25.0% | 25.0% | 100.0% | 25.0% | 0.0% | 66.7% |
| 0-6 hr | 94.8% | 61.1% | 35.7% | 14.3% | 100.0% | 46.2% | 72.7% | 90.9% |
| 0-12 hr | 94.8% | 50.0% | 48.9% | 20.0% | 97.8% | 43.5% | 86.5% | 94.6% |
| 0-24 hr | 94.8% | 68.2% | 61.5% | 22.2% | 99.3% | 49.3% | 86.1% | 97.0% |

BNP is also somewhat elevated in unstable angina but it is more indicative of myocardial infarction, particularly at early times in the event. When used in combination with MMP-9 and TnI, BNP may add useful information the diagnosis of acute coronary syndromes TpP, MCP-1, and FABP are all elevated to varying degrees at various times during acute coronary syndromes and, as a result, could add information used to form a diagnosis.

Since all of these markers serve different functions and are derived from a variety of sources, their appearance in circulation during acute coronary syndromes is likely to be independent of one another. Therefore, a diagnostic panel using two or more of the markers would be a benefit to the clinician providing information that could help guide therapy.

Example 6

Use of Markers in Patient Therapy

The observation that MMP-9, cTnI, BNP, and CRP are each independently associated with 10-month patient mortality indicates that multi-marker testing strategies in patients with suspected ACS can advantageously improve risk-prediction in comparison to measurement of individual markers. In addition to such prognostic and diagnostic applications, the markers of the present invention can also be used to assist in the delivery of therapy to ACS patients. For example, the use of such a biomarker risk "profile" may be used to target specific therapies to different underlying pathophysiologic mechanisms. This "risk profile" may be determined by various combinations of MMP-9, cTnI, BNP, and CRP, as well as by other markers used in addition to or substituted for said markers.

Additionally, markers such as MMP-9 that play a direct pathogenic role in atherosclerosis and its complications can provide novel therapeutic targets for drug discovery. For example, the MMP system might be regulated on at least four levels: gene transcription, message translation, proenzyme activation, and inhibition by tissue inhibitors of metalloproteinases (TIMPs). Modification of one or more of these steps may prevent atherosclerotic plaque rupture and modify adverse vascular and cardiac remodeling.

Therapeutic strategies can include, e.g., delivery of antisense compositions in order to disrupt the synthesis of MMP-9; delivery of receptor-based therapeutics (e.g., an antibody composition directed to MMP-9 or a fragment thereof); and/or delivery of small molecule thrapeutics (e.g., heparin can decrease MMP-9 synthesis, tetracycline antibiotics can inactivate MMPs by chelating zinc, and HMG Co-A Reductase inhibitors and activators of Peroxisomal Proliferator-Activator Receptor (PPAR)-gamma can decrease MMP-9 expression from macrophages. Such strategies may be directed at the target molecule itself (in this example, MMP-9), or, alternatively, at an upstream molecule necessary for target activation or activity (e.g., proteases such as plasmin, which cleaves the MMP-9 zymogen to its active form).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of diagnosing myocardial ischemia due to stable or unstable angina in a patient, the method comprising:
   performing a cardiac stress test on said patient;
   performing an assay that detects one or more of BNP, NT-proBNP, or proBNP in a sample obtained from said patient;
   performing an assay that detects one or more of cardiac troponin I or cardiac troponin T in a sample obtained from said patient; and
   correlating the assay results obtained from the assays performed to the presence or absence of myocardial ischemia due to stable or unstable angina in said patient.

2. A method according to claim 1, wherein said sample is selected from the group consisting of a blood sample, a serum sample, and a plasma sample.

3. A method according to claim 1, wherein said method further comprises performing one or more additional assays that detect one or more additional diagnostic indicators in said patient to provide one or more additional assay results, wherein one or more of said additional diagnostic indicators is selected from the group consisting of annexin V, B-type natriuretic peptide, β-enolase, cardiac troponin I (free and/or complexed), cardiac troponin T (free and/or complexed), creatine kinase-MB, glycogen phosphorylase-BB, heart-type fatty acid binding protein, phosphoglyceric acid mutase-MB, and S-100ao.

4. A method according to claim 1, wherein said method further comprises performing one or more additional assays that detect one or more additional diagnostic indicators in said patient to provide one or more additional assay results, wherein one or more of said additional diagnostic indicators is selected from the group consisting of β-thromboglobulin, D-dimer, fibrinopeptide A, platelet-derived growth factor, plasmin-α-2-antiplasmin complex, platelet factor 4, prothrombin fragment 1+2, P-selectin, thrombin-antithrombin III complex, thrombus precursor protein, tissue factor, and von Willebrand factor.

5. A method according to claim 1, wherein said method further comprises performing one or more additional assays that detect one or more additional diagnostic indicators in said patient to provide one or more additional assay results, wherein one or more of said additional diagnostic indicators is selected from the group consisting of C-reactive protein, ceruloplasmin, fibrinogen, α1-acid glycoprotein, α1-antitrypsin, and haptoglobin, insulin-like growth factor-1, interleukin-1β, interleukin-1 receptor antagonist, interleukin-6, interleukin-8, transforming growth factor β, monocyte chemotactic protein-1, and tumor necrosis factor α.

6. A method according to claim 1, wherein said method further comprises performing one or more additional assays that detect one or more additional diagnostic indicators in said patient to provide one or more additional assay results, wherein one or more of said additional diagnostic indicators is selected from the group consisting of human neutrophil elastase, inducible nitric oxide synthase, lysophosphatidic acid, malondialdehyde-modified low-density lipoprotein, matrix metalloproteinase-1, matrix metalloproteinase-2, matrix metalloproteinase-3, matrix metalloproteinase-9, caspase-3, hemoglobin α2, soluble intercellular adhesion molecule-1 and soluble vascular cell adhesion molecule-1.

7. A method according to claim 1, wherein said method further comprises performing one or more additional assays that detect one or more additional diagnostic indicators in said patient to provide one or more additional assay results, wherein one or more of said additional diagnostic indicator(s) are selected from the group consisting of MMP-9, TpP, MCP-1, H-FABP, CRP, creatine kinase, creatine kinase-MB, cardiac troponin I, cardiac troponin T, and complexes comprising cardiac troponin I and cardiac troponin T.

8. A method according to claim 1, wherein said method distinguishes between myocardial necrosis and myocardial ischemia due to stable or unstable angina in said patient.

9. A method according to claim 1, wherein said one or more additional diagnostic indicators is other than a natriuretic peptide.

10. A method according to claim 1, wherein said assay results are obtained following cardiac stress testing.

* * * * *

```
                       SEQUENCE LISTING

<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 1
aggtgtcgta agcttgaatt cagacacctc tgccgccacc atgag                45

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 2
gggctggctt acctgcggcc ttagtgatgg tgatggtgat ggtcctcagg gcactgcagg    60
atg                                                                  63

<210> SEQ ID NO 3
<211> LENGTH: 20
<212> TYPE: DNA
```

-continued

```
<213> ORGANISM: Artificial Sequence
<220> FEATURE:
<223> OTHER INFORMATION: Description of Artificial Sequence: Primer

<400> SEQUENCE: 3
ttctcaagcc tcagacagtg                                               20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
cctggatgca ggctactcta g                                             21
```